US011104953B2

(12) United States Patent
Wong et al.

(10) Patent No.: US 11,104,953 B2
(45) Date of Patent: *Aug. 31, 2021

(54) SEPTIC SHOCK ENDOTYPING STRATEGY AND MORTALITY RISK FOR CLINICAL APPLICATION

(71) Applicants: Children's Hospital Medical Center, Cincinnati, OH (US); University of Cincinnati, Cincinnati, OH (US)

(72) Inventors: Hector R. Wong, Cincinnati, OH (US); Christopher John Lindsell, Cincinnati, OH (US)

(73) Assignees: CHILDREN'S HOSPITAL MEDICAL CENTER, Cincinnati, OH (US); UNIVERSITY OF CINCINNATI, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/998,427

(22) Filed: Aug. 15, 2018

(65) Prior Publication Data

US 2019/0065666 A1    Feb. 28, 2019

Related U.S. Application Data

(63) Continuation-in-part of application No. PCT/US2017/032538, filed on May 12, 2017.

(60) Provisional application No. 62/446,216, filed on Jan. 13, 2017, provisional application No. 62/428,451, filed on Nov. 30, 2016, provisional application No. 62/427,778, filed on Nov. 29, 2016, provisional application No. 62/335,803, filed on May 13, 2016, provisional application No. 62/616,646, filed on Jan. 12, 2018.

(51) Int. Cl.
    *C12Q 1/6883*    (2018.01)

(52) U.S. Cl.
    CPC ..... *C12Q 1/6883* (2013.01); *C12Q 2600/106* (2013.01); *C12Q 2600/112* (2013.01); *C12Q 2600/118* (2013.01); *C12Q 2600/158* (2013.01)

(58) Field of Classification Search
    None
    See application file for complete search history.

(56) References Cited

U.S. PATENT DOCUMENTS

| 9,238,841 | B2 | 1/2016 | Wong et al. |
| 9,267,175 | B2 | 2/2016 | Wong et al. |
| 2009/0312194 | A1 | 12/2009 | Tyner et al. |
| 2013/0209473 | A1 | 8/2013 | de Sauvage et al. |
| 2014/0314865 | A1 | 10/2014 | von Andrian et al. |
| 2014/0323391 | A1 | 10/2014 | Tsalik et al. |
| 2014/0349890 | A1 | 11/2014 | Namsaraev |
| 2015/0018238 | A1 | 1/2015 | Wong et al. |

FOREIGN PATENT DOCUMENTS

WO    2015077781 A1    5/2015

OTHER PUBLICATIONS

Wong et al. (BMC Medicine. Jul. 2009. 7:34, p. 1-12 (Year: 2009).*
Cazalis et al Intensive Care Medicine Experimental. 2014. 2: 20, p. 1-17 and Supplementary table 1 (Year: 2014).*
Wong et al. Am J Respir Crit Care Med. Feb. 1, 2015. 191(3): 309-315 (Year: 2015).*
Wong et al Online Data Supplement, Supplemental Tables 1 and 2, 5 pages; Am J Respir Critical Care Medicine. Feb. 1, 2015. 191(3). (Year: 2015).*
International Search Report and Written Opinion, dated Aug. 16, 2017, received in International Application No. PCT/US17/32538.
Alder et al., "The pediatric sepsis biomarker risk model: Potential implications for sepsis therapy and biology," Expert Review of Anti-Infective Therapy 12(7):809-816, Jul. 1, 2014.
Annane et al., "Effect of treatment with low doses of hydrocortisone and fludrocortisone on mortality in patients with septic shock," JAMA 288(7):862-871, Aug. 21, 2002.
Atkinson et al., "Corticosteroids and pediatric septic shock outcomes: a risk stratified analysis," PloS One 9(11):e112702, Nov. 11, 2014.
Atkinson et al., "Identifying critically ill patients who may benefit from adjunctive corticosteroids: not as easy as we thought," Pediatric Critical Care Medicine: A Journal of the Society of Critical Care Medicine and the World Federation of Pediatric Intensive and Critical Care Societies 15(8):769-771, Oct. 2014.
Britto et al., "REDD1 deletion prevents dexamethasone-induced skeletal muscle atrophy," American Journal of Physiology-Endocrinology and Metabolism 307(11):E983-93, Dec. 1, 2014.
Che et al., "Decision tree and ensemble learning algorithms with their applications in bioinformatics," Advances in Experimental Medicine and Biology 696:191-199, Mar. 15, 2011.
Cohen et al., "Sepsis: a roadmap for future research," The Lancet Infectious Diseases 15(5):581-614, May 1, 2015.
Cooks et al., "Caught in the cross tire: P53 in inflammation," Carcinogenesis 35(8):1680-1690, Aug. 1, 2014.
Dellinger et al., "Surviving Sepsis Campaign: international guidelines for management of severe sepsis and septic shock: 2008," Critical Care Medicine 36(1):296-327, Jan. 2008.

(Continued)

*Primary Examiner* — Carla J Myers
(74) *Attorney, Agent, or Firm* — Davis Wright Tremaine LLP

(57) ABSTRACT

Methods and compositions disclosed herein generally relate to methods of identifying, validating, and measuring clinically relevant, quantifiable biomarkers of diagnostic and therapeutic responses for blood, vascular, cardiac, and respiratory tract dysfunction, particularly as those responses relate to septic shock in pediatric patients. In particular, the invention relates to identifying two or more biomarkers associated with septic shock in pediatric patients, obtaining a sample from a pediatric patient having at least one indication of septic shock, then quantifying from the sample an amount of two or more of said biomarkers, wherein the level of said biomarker correlates with a predicted outcome.

13 Claims, 15 Drawing Sheets

(56) References Cited

OTHER PUBLICATIONS

Dombrovskiy et al., "Rapid increase in hospitalization and mortality rates for severe sepsis in the United States: A trend analysis from 1993 to 2003," Critical Care Medicine 35(5):1244-50, May 2007.

Fan et al., "Endothelial progenitor cells and a stromal cell-derived factor-1alpha analogue synergistically improve survival in sepsis," American Journal of Respiratory and Critical Care Medicine 189(12):1509-1519, Jun. 15, 2014.

Geiss et al.,"Direct multiplexed measurement of gene expression with color-coded probe pairs," Nature Biotechnology 26(3):317-325, Mar. 1, 2008.

Goldstein et al., "International Pediatric Sepsis Consensus Conference: Definitions for sepsis and organ dysfunction in pediatrics," Pediatric Critical Care Medicine 6(1):2-8, Jan. 2005.

Gordon et al., "Emerging role for regulated in development and DNA damage 1 (REDD1) in the regulation of skeletal muscle metabolism," American Journal of Physiology-Endocrinology and Metabolism 311(1):E157-74, Jul. 1, 2016.

Guo et al., "A Stromal Cell-derived Factor 1 alpha Analogue Improves Endothelial Cell Function in Lipopolysaccharide-induced Acute Respiratory Distress Syndrome," Molecular Medicine 22(1):115-123, Jan. 2016.

Hanley et al., "A method of comparing the areas under receiver operating characteristic curves derived from the same cases," Radiology 148(3):839-843, Sep. 1983.

Hofseth et al., "Nitric oxide-induced cellular stress and p53 activation in chronic inflammation," Proceedings of the National Academy of Sciences 100(1):143-148, Jan. 7, 2003.

Hotchkiss et al., "P53-dependent and -independent pathways of apoptotic cell death in sepsis," The Journal of Immunology 164(7):3675-3680, Apr. 1, 2000.

Hutchins et al., "The new normal: immunomodulatory agents against sepsis immune suppression," Trends in Molecular Medicine 20(4):224-233, Apr. 1, 2014.

Jiang et al., "PRC1: A human mitotic spindle-associated cdk substrate protein required for cytokinesis," Molecular Cell 2(6):877-85, Dec. 1, 1998.

Johnson et al., "Nuclear factor-kappaB, p53, and mitochondria: Regulation of cellular metabolism and the Warburg effect," Trends in Biochemical Sciences 37(8):317-324, Aug. 1, 2012.

Kplan et al., "Biomarker discovery and development in pediatric critical care medicine," Pediatric Critical Care Medicine: a journal of the Society of Critical Care Medicine and the World Federation of Pediatric Intensive and Critical Care Societies 12(2): 165-173, Mar. 2011.

Kasuboski et al., "Zwint-1 is a novel aurora b substrate required for the assembly of a dynein-binding platform on kinetochores," Molecular Biology of the Cell 22(18):3318-3330, Sep. 15, 2011.

Komarova et al., "P53 is a suppressor of inflammatory response in mice," The FASEB Journal 19(8):1030-2, Apr. 5, 2005.

Kops et al., "ZW10 links mitotic checkpoint signaling to the structural kinetochore," The Journal of Cell Biology 169(1):49-60, Apr. 11, 2005.

Laudanski et al., "Cell-specific expression and pathway analyses reveal alterations in trauma-related human t cell and monocyte pathways," Proceedings of the National Academy of Sciences 103(42):15564-9, Oct. 17, 2006.

Li et al., "Identification of PRC1 as the p53 target gene uncovers a novel function of p53 in the regulation of cytokinesis," Oncogene 23(58):9336-47, Dec. 2004.

Lipina et al., "Is REDD1 a Metabolic Éminence Grise?" Trends in Endocrinology and Metabolism 27(12):868-80, Dec. 1, 2016.

Liu et al., "P53 attenuates lipopolysaccharideinduced nf-kappaB activation and acute lung injury," The Journal of Immunology 182(8):5063-71, Apr. 15, 2009.

Maiuri et al., "Autophagy regulation by p53," Current Opinion in Cell Biology 22(2):181-185, Apr. 1, 2010.

Manukyan et al., "The phosphoinositide-3 kinase survival signaling mechanism in sepsis," Shock 34(5):442-449, Nov. 1, 2010.

Marlow et al., "A randomised trial of granulocyte-macrophage colony-stimulating factor for neonatal sepsis: childhood outcomes at 5 years," Archives of Disease in Childhood Fetal and Neonatal Edition 100(4):F320-326, Jul. 1, 2015.

Marshall, "Sepsis: rethinking the approach to clinical research," Journal of Leukocyte Biology 83(3):471-82, Mar. 2008.

Maslove et al., "Gene expression profiling in sepsis: timing, tissue, and translational considerations," Trends in Molecular Medicine 20(4):204-213, Apr. 1, 2014.

Mathias et al., "A Review of GM-CSF Therapy in Sepsis," Medicine 94(50):e2044, Dec. 2015.

Mickiewicz et al., "Metabolomics as a novel approach for early diagnosis of pediatric septic shock and its mortality," American Journal of Respiratory and Critical Care Medicine 187(9):967-76, May 1, 2013.

Muller et al., "Logistic regression and CART in the analysis of multimarker studies," Clinica Chimica Acta 394(1-2):1-6, Aug. 1, 2008.

Murphy et al., "Tumor suppressor protein (p)53, is a regulator of nf-kappaB repression by the glucocorticoid receptor," Proceedings of the National Academy of Sciences 108(41):17117-22, Oct. 11, 2011.

Patel et al., "Systemic steroids in severe sepsis and septic shock," American Journal of Respiratory and Critical Care Medicine 185(2):133-139, Jan. 15, 2012.

Pollack et al., "The Pediatric Risk of Mortality III—Acute Physiology Score (PRISM III-APS): a method of assessing physiologic instability for pediatric intensive care unit patients," The Journal of Pediatrics 131(4):575-581, Oct. 1, 1997.

Prescott et al., "Toward smarter lumping and smarter splitting: Rethinking strategies for sepsis and acute respiratory distress syndrome clinical trial design," American Journal of Respiratory and Critical Care Medicine 194(2):147-155, Jul. 15, 2016.

Sabio et al., "TNF and MAP kinase signalling pathways," Seminars in Immunology 26(3):237-245, Jun. 1, 2014.

Sengupta et al., "Negative cross-talk between p53 and the glucocorticoid receptor and its role in neuroblastoma cells," The EMBO Journal 19(22):6051-64, Nov. 15, 2000.

Shanley et al., "Genome-level longitudinal expression of signaling pathways and gene networks in pediatric septic shock," Molecular Medicine 13(9-10):495-508, Sep. 1, 2007.

Shrestha et al., "PRC1 controls spindle polarization and recruitment of cytokinetic factors during monopolar cytokinesis," Molecular Biology of the Cell 23(7):1196-1207, Apr. 1, 2012.

Simon, "Clinical trial designs for evaluating the medical utility of prognostic and predictive biomarkers in oncology," Personalized Medicine 7(1):33-47, Jan. 2010.

Sprung et al., "Hydrocortisone therapy for patients with septic shock," The New England Journal of Medicine 358(2):111-124, Jan. 10, 2008.

Standage et al., "Biomarkers for pediatric sepsis and septic shock," Expert Review of Anti-Infective Therapy, 9(1):71-79, Jan. 1, 2011.

Steiner et al., "Disruption of REDD1 gene ameliorates sepsis-induced decrease in mTORC1 signaling but has divergent effects on proteolytic signaling in skeletal muscle," American Journal of Physiology-Endocrinology and Metabolism 309(12):E981-94, Dec. 15, 2015.

Subramanian et al., "Insights into antiparallel microtubule crosslinking by PRC1, a conserved nonmotor microtubule binding protein," Cell 142(3):433-443, Aug. 6, 2010.

Tan et al., "Transcriptional activation of the human glutathione peroxidase promoter by p53," Journal of Biological Chemistry 274(17):12061-6, Apr. 23, 1999.

Watson et al., "The epidemiology of severe sepsis in children in the United States," American Journal of Respiratory and Critical Care Medicine 167(5):695-701, Mar. 1, 2003.

Weiss et al., "Differential expression of the nuclear-encoded mitochondrial transcriptome in pediatric septic shock," Critical Care 18(6):623, Dec. 2014.

Wong et al., "Combining prognostic and predictive enrichment strategies to identify children with septic shock responsive to corticosteroids," Critical Care Medicine 44(10):e1000, Oct. 2016.

(56) References Cited

OTHER PUBLICATIONS

Wong et al., "Correspondence: Simplification of a Septic Shock Endotyping Strategy for Clinical Application," American Journal of Respiratory and Critical Care Medicine 195(2):263-265, Jan. 15, 2017.
Wong et al., "Corticosteroids are associated with repression of adaptive immunity gene programs in pediatric septic shock," American Journal of Respiratory and Critical Care Medicine 189(8):940-6, Apr. 15, 2014.
Wong et al., "Developing a Clinically Feasible Personalized Medicine Approach to Pediatric Septic Shock," American Journal of Respiratory and Critical Care Medicine 191(3):309-315, Feb. 1, 2015.
Wong et al., "Endotype Transitions During the Acute Phase of Pediatric Septic Shock Reflect Changing Risk and Treatment Response," Critical Care Medicine 46(3):e242-e249, Mar. 2018.
Wong et al., "Gene Expression Omnibus Accession No. GSE66099," NCBI, May 12, 2015 (last updated Oct. 24, 2019) [retrieved Feb. 25, 2020], https://www.ncbi.nlm.nih.gov/geo/query/acc.cgi?acc=GSE66099, 2 pages.
Wong et al., "Genome-level expression profiles in pediatric septic shock indicate a role for altered zinc homeostasis in poor outcome," Physiological Genomics 30(2):146-155, Jul. 2007.
Wong et al., "Identification of pediatric septic shock subclasses based on genome-wide expression profiling," BMC Medicine 7(1):34, Jul. 22, 2009, 12 pages.
Wong et al., "Persevere II: Redefining the pediatric sepsis biomarker risk model with septic shock phenotype," Critical Care Medicine 44(11):2010-2017, Nov. 2016.
Wong et al., "Testing the prognostic accuracy of the updated pediatric sepsis biomarker risk model," PLoS One 9(1):e86242, Jan. 29, 2014.
Wong et al., "The pediatric sepsis biomarker risk model," Critical Care 16(5):R174, Oct. 1, 2012.
Wong et al., "Toward a clinically feasible gene expression-based subclassification strategy for septic shock: proof of concept," Critical Care Medicine 38(10): 1955-1961, Oct. 2010.
Wong et al., "Validation of a gene expression-based subclassification strategy for pediatric septic shock," Critical Care Medicine 39(11):2511-2517, Nov. 2011.
Wynn et al., "The influence of developmental age on the early transcriptomic response of children with septic shock," Molecular Medicine 17(11-12): 1146-1156, Nov. 1, 2011.
Yoon et al., "Identification of ALDH4 as a p53-inducible gene and its protective role in cellular stresses," Journal of Human Genetics 49(3):134-140, Mar. 2004.
Zhang et al., "What's the relative risk? A method of correcting the odds ratio in cohort studies of common outcomes," JAMA 280(19):1690-1691, Nov. 18, 1998.

* cited by examiner

SEPTIC SHOCK ENDOTYPING STRATEGY AND MORTALITY RISK FOR CLINICAL APPLICATION

CROSS REFERENCE TO RELATED APPLICATIONS

The present application is a continuation-in-part of International Application No. PCT/US2017/032538, SIMPLIFICATION OF A SEPTIC SHOCK ENDOTYPING STRATEGY FOR CLINICAL APPLICATIONS, filed on May 12, 2017, which claims the claims the benefit of priority under 35 U.S.C. § 119(e) to U.S. Provisional Application No. 62/335,803, SIMPLIFICATION OF A SEPTIC SHOCK ENDOTYPING STRATEGY FOR CLINICAL APPLICATIONS, filed on May 13, 2016; U.S. Provisional Application No. 62/427,778, SIMPLIFICATION OF A SEPTIC SHOCK ENDOTYPING STRATEGY FOR CLINICAL APPLICATIONS, filed on Nov. 29, 2016; U.S. Provisional Application No. 62/428,451, SIMPLIFICATION OF A SEPTIC SHOCK ENDOTYPING STRATEGY FOR CLINICAL APPLICATIONS, filed on Nov. 30, 2016; U.S. Provisional Application No. 62/446,216, SIMPLIFICATION OF A SEPTIC SHOCK. ENDOTYPING STRATEGY FOR CLINICAL APPLICATIONS, filed on Jan. 13, 2017, each of which is incorporated by reference in its entirety. The present application also claims the benefit of priority under 35 U.S.C. § 119(e) to U.S. Provisional Application No. 62/616,646, TEMPORAL ENDOTYPE TRANSITIONS REFLECT CHANGING RISK AND TREATMENT RESPONSE IN PEDIATRIC SEPTIC SHOCK, filed on Jan. 12, 2018, which is currently herewith and which is incorporated by reference in its entirety.

STATEMENT REGARDING FEDERALLY-SPONSORED RESEARCH

This invention was made with government support under GM064619, GM099773, GM108025, HL100474, GM096994, and TR000077 awarded by the National Institutes of Health (NIH). The government has certain rights in the invention.

FIELD OF THE INVENTION

The invention disclosed herein generally relates to the identification and validation of clinically relevant, quantifiable biomarkers of diagnostic and therapeutic responses for blood, vascular, cardiac, and respiratory tract dysfunction.

BACKGROUND

Septic shock and severe sepsis represent a major public health problem in the United States, despite the development of increasingly powerful antibiotics and advanced forms of intensive care unit-based support modalities (see, e.g., Shanley, T. et al. Sepsis, $3^{rd}$ Ed., St. Louis, Mo., Mosby (2006)). Worldwide, septic shock affects millions of adults, killing approximately one in four (see, e.g., Dellinger, R. et al. Crit. Care Med. 36:296-327 (2008)). One study suggests that the incidence and the mortality rates of septic shock in adults are increasing in the United States (Dombrovskiy, V. et al. Crit. Care Med. 35:1244-50 (2007)).

Septic shock is also a major problem in the pediatric age group, as there are ~42,000 cases of pediatric septic shock per year in the United States alone, with a mortality rate of ~10% (see, e.g., Watson, R. et al. Am. J. Respir. Crit. Care Med. 167:695-701 (2003)). While the pediatric mortality rate is lower than that of adults, it nonetheless translates to more than 4,000 childhood deaths per year and countless years of lost productivity due to death at a young age. While this high number of pediatric deaths per year from septic shock indicates that more children die per year in the United States from septic shock as the primary cause than those children who die from cancer, funding specifically targeted toward pediatric septic shock is substantially lower than that for pediatric cancer.

Septic shock is a clinical syndrome with substantial clinical and biological heterogeneity. Reliable risk stratification of patients with septic shock has numerous clinical applications, but is a challenging task due to the significant patient heterogeneity. As such, reliable stratification of outcome risk is fundamental to effective clinical practice and clinical research (Marshall J. Leukoc. Biol. 83:471-82 (2008)), as is the ability to differentiate between subclasses of septic shock that have different biology. For example, septic shock endotypes can have differences with respect to adaptive immunity and glucocorticoid receptor signaling, as well as different responses to steroid treatment. Risk stratification tools specific for septic shock in pediatric patients would be beneficial at several levels, including stratification for interventional clinical trials, better-informed decision making for individual patients (i.e. prognostication), and as a metric for quality improvement efforts. A recent Lancet Infectious Diseases Commission by Cohen et al. has outlined a roadmap for future research in the field of sepsis, including the identification of sepsis subclasses as a means of resolving heterogeneity and improving patient outcomes (1).

SUMMARY OF THE INVENTION

Certain embodiments of the invention relate to methods of classifying a pediatric patient with septic shock as high risk or low risk, wherein the methods include analyzing a sample from a pediatric patient with septic shock to determine the expression levels of two or more biomarkers selected from the biomarkers listed in Table 1, wherein the biomarkers include two or more selected from JAK2, LYN, PRKCB, and SOS2; determining whether the expression levels of the two or more biomarkers are elevated above a cut-off level; and classifying the patient as endotype A/high risk or other than endotype A/high risk, wherein a classification of endotype A/high risk includes: a) a non-elevated level of JAK2 and a non-elevated level of PRKCB; or b) a non-elevated level of JAK2, an elevated level of PRKCB, and a non-elevated level of LYN; and wherein a classification other than endotype A/high risk includes: c) a non-elevated level of JAK2, an elevated level of PRKCB, and an elevated level of LYN; or d) an elevated level of JAK2, a non-elevated level of SOS2, and a highly elevated level of LYN; or e) elevated levels of JAK2 and SOS2; or f) an elevated level of JAK2, a non-elevated level of SOS2, and a non-highly elevated level of LYN.

In certain embodiments of the methods, biomarker expression levels can be determined by mRNA quantification. In some embodiments, biomarker expression levels can be determined by normalized mRNA counts and/or by cycle threshold (CT) values.

In certain embodiments of the methods, the biomarkers include a pair of biomarkers selected from JAK2 and LYN; JAK2 and PRKCB; JAK2 and SOS2; LYN and PRKCB; LYN and SOS2; and PRKCB and SOS2. In some embodiments, the biomarkers include three or more selected from JAK2, LYN, PRKCB, and SOS2. In some embodiments, the biomarkers include a trio of biomarkers selected from JAK2, LYN, and PRKCB; JAK2, LYN, and SOS2; JAK2, PRKCB, and SOS2; LYN, PRKCB, and SOS2. In some embodiments, the biomarkers include all of JAK2, LYN, PRKCB, and SOS2.

In certain embodiments of the methods, biomarker levels can be determined by normalized mRNA counts, wherein: a) an elevated level of JAK2 corresponds to a serum JAK2 mRNA count greater than 1780; b) an elevated level of PRKCB corresponds to a serum PRKCB mRNA count greater than 990; c) an elevated level of SOS2 corresponds to a serum SOS2 mRNA count greater than 480; d) an elevated level of LYN corresponds to a serum LYN mRNA count greater than 870; and e) a highly elevated level of LYN corresponds to a serum LYN mRNA count greater than 940.

In certain embodiments of the methods, biomarker levels can be determined by normalized mRNA counts, wherein: a) an elevated level of JAK2 corresponds to a serum JAK2 mRNA count greater than 1784; b) an elevated level of PRKCB corresponds to a serum PRKCB mRNA count greater than 986; c) an elevated level of SOS2 corresponds to a serum SOS2 mRNA count greater than 480; d) an elevated level of LYN corresponds to a serum LYN mRNA count greater than 873; and e) a highly elevated level of LYN corresponds to a serum LYN mRNA count greater than 938.

In certain embodiments of the methods, the determination of whether the levels of the two or more biomarkers are non-elevated above a cut-off level includes applying the biomarker expression level data to a decision tree including the two or more biomarkers. Some embodiments of the methods include application of the decision tree of FIG. 1. Some embodiments of the methods include application of the decision tree of FIG. 4.

In certain embodiments of the methods, a classification other than endotype A/high risk includes a classification of endotype B/low risk or endotype C/moderate risk.

In certain embodiments of the methods, the determination of whether the levels of the two or more biomarkers are non-elevated can be combined with one or more patient demographic data and/or clinical characteristics and/or results from other tests or indicia of septic shock. In some embodiments, the patient demographic data and/or clinical characteristics and/or results from other tests or indicia of septic shock include at least one of the septic shock causative organism, the presence or absence or chronic disease, and/or the age, gender, race, and/or co-morbidities of the patient. In some embodiments, the determination of whether the levels of the two or more biomarkers are non-elevated above a cut-off level can be combined with one or more additional population-based risk scores. In some embodiments, the one or more population-based risk scores includes at least one of Pediatric Risk of Mortality (PRISM), Pediatric Index of Mortality (PIM), and/or Pediatric Logistic Organ Dysfunction (PELOD).

In some embodiments, the sample can be obtained within the first hour of presentation with septic shock. In some embodiments, the sample can be obtained within the first 48 hours of presentation with septic shock.

Certain embodiments of the methods further include administering a treatment including one or more corticosteroid to a patient that is not endotype A/high risk, or administering a treatment including one or more therapy excluding a corticosteroid to a patient that is classified as endotype A/high risk, to provide a method of treating a pediatric patient with septic shock. In some embodiments, one or more high risk therapy can be administered to a patient classified as endotype A/high risk. In some embodiments, the one or more high risk therapy includes at least one of immune enhancing therapy, extracorporeal membrane oxygenation/life support, plasmapheresis, pulmonary artery catheterization, and/or high volume continuous hemofiltration. In some embodiments, the immune enhancing therapy includes administration of GMCSF, interleukin-7, and/or anti-PD-1. Some embodiments of the methods include improving an outcome in a pediatric patient with septic shock.

Certain embodiments of the methods further include obtaining a sample from the patient at a later time point, analyzing the subsequent sample to determine the expression levels of the two or more biomarkers selected from the biomarkers listed in Table 1, and determining whether the expression levels of the two or more biomarkers are non-elevated above a cut-off level, thereby determining a change to the patient's endotype classification; and maintaining the treatment being administered if the patient's endotype classification has not changed, or changing the treatment being administered if the patient's endotype classification has changed.

Certain embodiments of the invention relate to methods of classifying a pediatric patient with septic shock, wherein the methods include analyzing a sample from a pediatric patient with septic shock to determine the expression levels of biomarkers including three or more members of a quartet selected from GNAI3, PIK3C3, TLR1, and TYROBP; CD247, ITGAX, RHOT1, and TLR1; ARPC5, CSNK1A1, FCGR2C, and PPP2R5C; ASAH1, FCGR2C, TRA, and TYROBP; BTK, FAS, MAP3K3, and PPP2R2A; CASP4, CD247, EP300, and MAP3K3; and CREB5, CSNK1A1, PRKCB, and TLR2; and determining whether the expression levels of the three or more biomarkers are elevated above a cut-off level.

In certain embodiments of the methods, a classification of endotype A includes: a) a non-highly elevated level of TLR1 and a non-elevated level of PIK3C3; or b) a non-elevated level of TLR1, and an elevated level of PIK3C3; or c) a highly elevated level of TLR1, a non-elevated level of GNAI3, and a non-elevated level of TYROBP; and a classification other than endotype A/high risk includes: d) an elevated level of TLR1, and an elevated level of PIK3C3; or e) a highly elevated level of TLR1, a non-elevated level of GNAI3, and an elevated level of TYROBP; or f) a highly elevated level of TLR1, and an elevated level of GNAI3. In some embodiments, biomarker levels can be determined by normalized mRNA counts, wherein: a) an elevated level of TLR1 corresponds to a serum TLR1 mRNA count greater than 1926; b) a highly elevated level of TLR1 corresponds to a serum TLR1 mRNA count greater than 3980; c) an elevated level of PIK3C3 corresponds to a serum PIK3C3 mRNA count greater than 366; d) an elevated level of GNAI3 corresponds to a serum GNAI3 mRNA count greater than 669; and e) an elevated level of TYROBP corresponds to a serum TYROBP mRNA count greater than 17190. Some embodiments of the methods include application of the decision tree of FIG. 3a.

In certain embodiments of the methods, a classification of endotype A/high risk includes: a) a non-elevated level of TLR1, a non-elevated level of RHOT1, and a non-elevated level of ITGAX; or b) a non-elevated level of TLR1, and an elevated level of RHOT1; or c) an elevated level of TLR1, a non-highly elevated level of RHOT1, and a non-highly elevated level of ITGAX; and a classification other than endotype A/high risk includes: d) a non-elevated level of TLR1, a non-elevated level of RHOT1, and an elevated level of ITGAX; or e) an elevated level of TLR1, a non-highly elevated level of RHOT1, and a highly elevated level of ITGAX; or f) an elevated level of TLR1, and a highly elevated level of RHOT1. In some embodiments, biomarker levels can be determined by normalized mRNA counts, wherein: a) an elevated level of TLR1 corresponds to a serum TLR1 mRNA count greater than 3980; b) an elevated level of RHOT1 corresponds to a serum RHOT1 mRNA count greater than 118; c) a highly elevated level of RHOT1 corresponds to a serum RHOT1 mRNA count greater than 739; d) an elevated level of ITGAX corresponds to a serum ITGAX mRNA count greater than 1511; and e) a highly elevated level of ITGAX corresponds to a serum ITGAX mRNA count greater than 3712. Some embodiments of the methods include application of the decision tree of FIG. 3b.

In certain embodiments of the methods, a classification of endotype A/high risk includes: a) a non-elevated level of CSNK1A1 and a non-highly elevated level of ARPC5; or b) a non-elevated level of CSNK1A1, a highly elevated level of ARPC5, and a non-elevated level of PPP2R5C; or c) an elevated level of CSNK1A1, a non-elevated level of ARPC5, and a non-elevated level of FCGR2C; and a classification other than endotype A/high risk includes: d) a non-elevated level of CSNK1A1, a highly elevated level of ARPC5, and an elevated level of PPP2R5C; or e) an elevated level of CSNK1A1, a non-elevated level of ARPC5, and an elevated level of FCGR2C; or f) an elevated level of CSNK1A1, and an elevated level of ARPC5. In some embodiments, biomarker levels can be determined by normalized mRNA counts, wherein: a) an elevated level of CSNK1A1 corresponds to a serum CSNK1A1 mRNA count greater than 258; b) an elevated level of ARPC5 corresponds to a serum ARPC5 mRNA count greater than 2184; c) a highly elevated level of ARPC5 corresponds to a serum ARPC5 mRNA count greater than 3648; d) an elevated level of PPP2R5C corresponds to a serum PPP2R5C mRNA count greater than 683; and e) an elevated level of FCGR2C corresponds to a serum FCGR2C mRNA count greater than 1261. Some embodiments of the methods include application of the decision tree of FIG. 3c.

In certain embodiments of the methods, a classification of endotype A/high risk includes: a) a non-elevated level of ASAH1 and a non-highly elevated level of TYROBP; or b) an elevated level of ASAH1, a non-elevated level of TYROBP, and a non-elevated level of FCGR2C; and a classification other than endotype A/high risk includes: c) a non-elevated level of ASAH1 and a highly elevated level of TYROBP; or d) an elevated level of ASAH1, a non-elevated level of TYROBP, and an elevated level of FCGR2C; or e) an elevated level of ASAH1, and an elevated level of TYROBP. In some embodiments, biomarker levels can be determined by normalized mRNA counts, wherein: a) an elevated level of ASAH1 corresponds to a serum ASAH1mRNA count greater than 2757; b) an elevated level of TYROBP corresponds to a serum TYROBP mRNA count greater than 9167; c) a highly elevated level of TYROBP corresponds to a serum TYROBP mRNA count greater than 12540; and d) an elevated level of FCGR2C corresponds to a serum FCGR2C mRNA count greater than 1261. Some embodiments of the methods include application of the decision tree of FIG. 3d.

In certain embodiments of the methods, a classification of endotype A/high risk includes: a) a non-elevated level of MAP3K3, a non-elevated level of PPP2R2A, and a non-highly elevated level of FAS; or b) an elevated level of MAP3K3 which is not a highly elevated level of MAP3K3, and a non-elevated level of FAS; and a classification other than endotype A/high risk includes: c) a non-elevated level of MAP3K3, a non-elevated level of PPP2R2A, and a highly elevated level of FAS; or d) a non-elevated level of MAP3K3, and an elevated level of PPP2R2A; or e) a highly elevated level of MAP3K3, and a non-elevated level of FAS; or f) an elevated level of MAP3K3, and an elevated level of FAS. In some embodiments, biomarker levels can be determined by normalized mRNA counts, wherein: a) an elevated level of MAP3K3 corresponds to a serum MAP3K3 mRNA count greater than 1063; b) a highly elevated level of MAP3K3 corresponds to a serum MAP3K3 mRNA count greater than 1251; c) an elevated level of PPP2R2A corresponds to a serum PPP2R2A mRNA count greater than 2866; d) an elevated level of FAS corresponds to a serum FAS mRNA count greater than 422; and e) a highly elevated level of FAS corresponds to a serum FAS mRNA count greater than 919. Some embodiments of the methods include application of the decision tree of FIG. 3e.

In certain embodiments of the methods, a classification of endotype A/high risk includes: a) a non-elevated level of MAP3K3, a non-highly elevated level of EP300, and a non-highly elevated level of CASP4; or b) an elevated level of MAP3K3, a non-elevated level of CASP4, and a non-elevated level of EP300; and a classification other than endotype A/high risk includes: c) a non-elevated level of MAP3K3, a non-highly elevated level of EP300, and a highly elevated level of CASP4; or d) a non-elevated level of MAP3K3, and a highly elevated level of EP300; or e) an elevated level of MAP3K3, a non-elevated level of CASP4, and a non-elevated level of EP300; or f) an elevated level of MAP3K3, and an elevated level of CASP4. In some embodiments, biomarker levels can be determined by normalized mRNA counts, wherein: a) an elevated level of MAP3K3 corresponds to a serum MAP3K3 mRNA count greater than 1063; b) an elevated level of EP300 corresponds to a serum EP300 mRNA count greater than 741; c) a highly elevated level of EP300 corresponds to a serum EP300 mRNA count greater than 4395; d) an elevated level of CASP4 corresponds to a serum CASP4 mRNA count greater than 988; and e) a highly elevated level of CASP4 corresponds to a serum CASP4 mRNA count greater than 1491. Some embodiments of the methods include application of the decision tree of FIG. 3f.

In certain embodiments of the methods, a classification of endotype A/high risk includes: a) a non-elevated level of CRES5, and a non-highly elevated level of TLR2; or b) a non-elevated level of CREB5, a highly elevated level of TLR2, and a non-highly elevated level of CSNK1A1; or c) an elevated level of CREB5, a non-elevated level of TLR2, and a non-elevated level of CSNK1A1; and a classification other than endotype A/high risk includes: d) a non-elevated level of CREB5, a highly elevated level of TLR2, and a highly elevated level of CSNK1A1; or e) an elevated level of CREB5, a non-elevated level of TLR2, and an elevated level of CSNK1A1; or f) an elevated level of CREB5, and an elevated level of TLR2. In some embodiments, biomarker levels can be determined by normalized mRNA counts, wherein: a) an elevated level of CREB5 corresponds to a serum CREB5 mRNA count greater than 950; b) an elevated level of TLR2 corresponds to a serum TLR2 mRNA count greater than 1634; c) a highly elevated level of TLR2 corresponds to a serum TLR2 mRNA count greater than 1751; d) an elevated level of CSNK1A1 corresponds to a serum CSNK1A1 mRNA count greater than 254; and e) a highly elevated level of CSNK1A1 corresponds to a serum CSNK1A1 mRNA count greater than 259. Some embodiments of the methods include application of the decision tree of FIG. 3g.

Certain embodiments of the invention relate to diagnostic kits, tests, or arrays including a reporter hybridization probe, and a capture hybridization probe specific for each of two or more mRNA markers selected from the biomarkers listed in Table 1. In certain embodiments, the mRNA markers include three or more selected from ARPC5, ASAH1, BTK, CASP4, CD247, CREB5, CSNK1A1, EP300, FAS, FCGR2C, GNAI3, ITGAX, JAK2, LYN, MAP3K3, PIK3C3, PPP2R2A, PPP2R5C, PRKCB, RHOT1, SOS2, TLR1, TLR2, TRA, and TYROBP. In certain embodiments, the mRNA markers include JAK2, LYN, PRKCB, and SOS2. Certain embodiments further include a collection cartridge for immobilization of the hybridization probes. In some embodiments, the reporter and the capture hybridization probes include signal and barcode elements, respectively.

Certain embodiments of the invention relate to apparatuses or processing devices suitable for detecting two or more biomarkers selected from the biomarkers listed in Table 1. In certain embodiments, the biomarkers include three or more selected from ARPC5, ASAH1, BTK, CASP4, CD247, CREB5, CSNK1A1, EP300, FAS, FCGR2C, GNAI3, ITGAX, JAK2, LYN, MAP3K3, PIK3C3, PPP2R2A, PPP2R5C, PRKCB, RHOT1, SOS2, TLR1, TLR2, TRA, and TYROBP. In certain embodiments, the biomarkers include JAK2, LYN, PRKCB, and SOS2.

Certain embodiments of the invention relate to compositions including a reporter hybridization probe, and a capture hybridization probe specific for each of two or more mRNA markers selected from the biomarkers listed in Table 1. In certain embodiments, the mRNA markers include three or more selected from ARPC5, ASAH1, BTK, CASP4, CD247, CREB5, CSNK1A1, EP300, FAS, FCGR2C, GNAI3, ITGAX, JAK2, LYN, MAP3K3, PIK3C3, PPP2R2A, PPP2R5C, PRKCB, RHOT1, SOS2, TLR1, TLR2, TRA, and TYROBP. In certain embodiments, the mRNA markers include JAK2, LYN, PRKCB, and SOS2.

Certain embodiments of the invention relate to methods of classifying a pediatric patient with septic shock as having high mortality risk or low mortality risk, wherein the methods include analyzing a sample from a pediatric patient with septic shock to determine the expression levels of two or more protein biomarkers selected from CCL3, IL8, HSPA1B, GZMB, and MMP8, to determine the patient's PERSEVERE mortality probability; analyzing the sample to determine the expression levels of two or more mRNA biomarkers selected from DDIT4, HAL, PRCI, and ZWINT; determining whether the expression levels of the two or more mRNA biomarkers are elevated above a cut-off level; and classifying the patient as high mortality risk or low mortality risk, wherein a classification of high mortality risk includes: a) a non-elevated PERSEVERE mortality probability, an elevated level of PRCI, and a non-highly elevated level of HAL; or b) an elevated PERSEVERE mortality probability, and non-elevated levels of DDIT4, ZWINT, and HAL; or c) an elevated PERSEVERE mortality probability, a non-elevated level of DDIT4, and an elevated level of ZWINT; or d) an elevated PERSEVERE mortality probability, and an elevated level of DDIT4; and wherein a classification other than high mortality risk includes: e) a non-elevated PERSEVERE mortality probability, and a non-elevated level of PRCI; or f) a non-elevated PERSEVERE mortality probability, an elevated level of PRCI, and a highly elevated level of HAL; or g) an elevated PERSEVERE mortality probability, non-elevated levels of DDIT4 and ZWINT, and an elevated level of HAL.

In certain embodiments of the methods, mRNA biomarker expression levels for DDIT4, HAL, PRCI, and ZWINT are determined by mRNA quantification, and protein biomarker expression levels for CCL3, IL8, HSPA1B, GZMB, and MMP8 are determined by serum protein concentration. In some embodiments, mRNA biomarker expression levels for DDIT4, HAL, PRCI, and ZWINT are determined by normalized mRNA counts and/or by cycle threshold (CT) values, and protein biomarker expression levels for CCL3, IL8, HSPA1B, GZMB, and MMP8 are determined using a multi-plex magnetic bead platform.

In some embodiments, the mRNA biomarkers include a pair of biomarkers selected from: PRCI and HAL; DDIT4 and ZWINT; ZWINT and HAL; DDIT4 and HAL; PRCI and DDIT4; and PRCI and ZWINT. In some embodiments, the mRNA biomarkers include three or more selected from DDIT4, HAL, PRCI, and ZWINT. In some embodiments, the mRNA biomarkers include all of DDIT4, HAL, PRCI, and ZWINT.

In certain embodiments of the methods, an elevated PERSEVERE mortality probability corresponds to a PERSEVERE mortality probability greater than 0.025, and mRNA biomarker levels are determined by normalized mRNA counts, wherein: a) an elevated level of PRCI corresponds to a serum PRCI mRNA count greater than 37; b) an elevated level of HAL corresponds to a serum HAL mRNA count greater than 58; c) a highly elevated level of HAL corresponds to a serum HAL mRNA count greater than 124; d) an elevated level of DDIT4 corresponds to a serum DDIT4 mRNA count greater than 105; and e) an elevated level of ZWINT corresponds to a serum ZWINT mRNA count greater than 28.

In some embodiments, an elevated PERSEVERE mortality probability includes: a) a non-elevated level of CCL3, and an elevated level of HSPA1B; or b) non-elevated levels of CCL3 and HSPA1B, and a highly elevated level of IL8; or c) elevated levels of CCL3 and MMP8, and a non-elevated level of IL8; or d) elevated levels of CCL3 and IL8, a non-elevated level of GZMB, and a patient age at or below 0.5 years; or e) elevated levels of CCL3, IL8, and GZMB; and a non-elevated PERSEVERE mortality probability includes: f) non-elevated levels of CCL3 and HSPA1B, and a non-highly elevated level of IL8; or g) an elevated level of CCL3, and non-elevated levels of IL8 and MMP8; or h) elevated levels of CCL3 and IL8, a non-elevated level of GZMB, and a patient age greater than 0.5 years. In some embodiments involving determining an elevated PERSEVERE mortality probability, a) an elevated level of CCL3 corresponds to a serum CCL3 concentration greater than 160 pg/ml; b) an elevated level of HSPA1B corresponds to a serum HSPAIB concentration greater than 3.3 µg/ml; c) an elevated level of IL8 corresponds to a serum IL8 concentration greater than 507 pg/ml; d) a highly elevated level of IL8 corresponds to a serum IL8 concentration greater than 829 pg/ml; e) an elevated level of GZMB corresponds to a serum GZMB concentration greater than 55 pg/ml; and f) an elevated level of MMP8 corresponds to a serum MMP8 concentration greater than 47.5 ng/ml.

In some embodiments, the determination of whether the levels of the two or more mRNA biomarkers are non-elevated above a cut-off level includes applying the biomarker expression level data to a decision tree including the two or more biomarkers. In some embodiments, the methods include application of the decision tree of FIG. 6.

In some embodiments, the determination of whether the levels of the two or more mRNA biomarkers are non-elevated can be combined with one or more patient demographic data and/or clinical characteristics and/or results from other tests or indicia of septic shock. In some embodiments, the patient demographic data and/or clinical characteristics and/or results from other tests or indicia of septic shock include at least one selected from the septic shock causative organism, the presence or absence or chronic disease, and/or the age, gender, race, and/or co-morbidities of the patient. In some embodiments, the determination of whether the levels of the two or more mRNA biomarkers are non-elevated above a cut-off level can be combined with one or more additional population-based risk scores. In some embodiments, the one or more population-based risk scores includes at least one selected from Pediatric Risk of Mortality (PRISM), Pediatric Index of Mortality (PIM), and/or Pediatric Logistic Organ Dysfunction (PELOD).

In some embodiments, the sample can be obtained within the first hour of presentation with septic shock, or the sample can be obtained within the first 48 hours of presentation with septic shock.

In some embodiments of the methods, the determination of whether the levels of the two or more mRNA biomarkers are non-elevated can be combined with a method of classifying a pediatric patient with septic shock as high risk or low risk according to patient endotype. In some embodiments, the determination of whether the levels of the two or more mRNA biomarkers are non-elevated can be combined with a method of classifying a pediatric patient with septic shock as high risk or low risk, including analyzing a sample from a pediatric patient with septic shock to determine the expression levels of two or more biomarkers selected from the biomarkers listed in Table 1, wherein the biomarkers include two or more selected from JAK2, LYN, PRKCB, and SOS2; determining whether the expression levels of the two or more biomarkers are elevated above a cut-off level; and classifying the patient as endotype A/high risk or other than endotype A/high risk, wherein a classification of endotype A/high risk includes: a) a non-elevated level of JAK2 and a non-elevated level of PRKCB; or b) a non-elevated level of JAK2, an elevated level of PRKCB, and a non-elevated level of LYN; and wherein a classification other than endotype A/high risk includes: c) a non-elevated level of JAK2, an elevated level of PRKCB, and an elevated level of LYN; or d) an elevated level of JAK2, a non-elevated level of SOS2, and a highly elevated level of LYN; or e) elevated levels of JAK2 and SOS2; or f) an elevated level of JAK2, a non-elevated level of SOS2, and a non-highly elevated level of LYN.

Some embodiments of the methods further include administering a treatment including one or more corticosteroid to a patient classified as other than endotype A/high risk wherein the patient is also classified as high mortality risk, or administering a treatment including one or more therapy excluding a corticosteroid to a patient that is classified as endotype A/high risk. Some embodiments further include administering a treatment including one or more corticosteroid to a patient that is not high mortality risk, or administering a treatment including one or more therapy excluding a corticosteroid to a patient that is classified as high mortality risk, to provide a method of treating a pediatric patient with septic shock. In some embodiments, one or more high risk therapy can be administered to a patient classified as high mortality risk. In some embodiments, the one or more high risk therapy includes at least one selected from immune enhancing therapy, extracorporeal membrane oxygenation/life support, plasmapheresis, pulmonary artery catheterization, and/or high volume continuous hemofiltration. In some embodiments, the immune enhancing therapy includes administration of GMCSF, interleukin-7, and/or anti-PD-1.

Embodiments of the invention also encompass improving an outcome in a pediatric patient with septic shock. In some embodiments, the methods further include
obtaining a sample from the patient at a later time point, analyzing the subsequent sample to determine the expression levels of the two or more biomarkers selected from the biomarkers listed in Table 1, and determining whether the expression levels of the two or more biomarkers are non-elevated above a cut-off level, thereby determining a change to the patient's endotype classification; and maintaining the treatment being administered if the patient's endotype classification has not changed, or changing the treatment being administered if the patient's endotype classification has changed.

Certain embodiments of the invention relate to diagnostic kits, tests, or arrays including a reporter hybridization probe, and a capture hybridization probe specific for each of two or more mRNA markers selected from the biomarkers listed in Table 12. In some embodiments, the mRNA markers include three or more selected from DDIT4, HAL, PRC1, and ZWINT, and further include three or more selected from ARPC5, ASAH1, BTK, CASP4, CD247, CREB5, CSNK1A1, EP300, FAS, FCGR2C, GNAI3, ITGAX, JAK2, LYN, MAP3K3, PIK3C3, PPP2R2A, PPP2R5C, PRKCB, RHOT1, SOS2, TLR1, TLR2, TRA, and TYROBP. In some embodiments, the mRNA markers include DDIT4, HAL, PRC1, and ZWINT. Certain embodiments further include a collection cartridge for immobilization of the hybridization probes. In some embodiments, the reporter and the capture hybridization probes include signal and barcode elements, respectively.

Certain embodiments of the invention relate to apparatuses or processing device suitable for detecting two or more biomarkers selected from the biomarkers listed in Table 12. In certain embodiments, the biomarkers include three or more selected from DDIT4, HAL, PRC1, and ZWINT, and further include three or more selected from CCL3, IL8, HSPA1B, GZMB, MMP8, ARPC5, ASAH1, BTK, CASP4, CD247, CREB5, CSNK1A1, EP300, FAS, FCGR2C, GNAI3, ITGAX, JAK2, LYN, MAP3K3, PIK3C3, PPP2R2A, PPP2R5C, PRKCB, RHOT1, SOS2, TLR1, TLR2, TRA, and TYROBP. In certain embodiments, the biomarkers include DDIT4, HAL, PRC1, ZWINT, CCL3, IL8, HSPAIB, GZMB, and MMP8.

Certain embodiments of the invention relate to compositions including a reporter hybridization probe, and a capture hybridization probe specific for each of two or more mRNA markers selected from the biomarkers listed in Table 12. In certain embodiments, the mRNA markers include three or more selected from DDIT4, HAL, PRC1, and ZWINT, and further include three or more selected from ARPC5, ASAH1, BTK, CASP4, CD247, CREB5, CSNK1A1, EP300, FAS, FCGR2C, GNAI3, ITGAX, JAK2, LYN, MAP3K3, PIK3C3, PPP2R2A, PPP2R5C, PRKCB, RHOT1, SOS2, TLR1, TLR2, TRA, and TYROBP. In certain embodiments, the mRNA markers include DDIT4, HAL, PRC1, and ZWINT.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
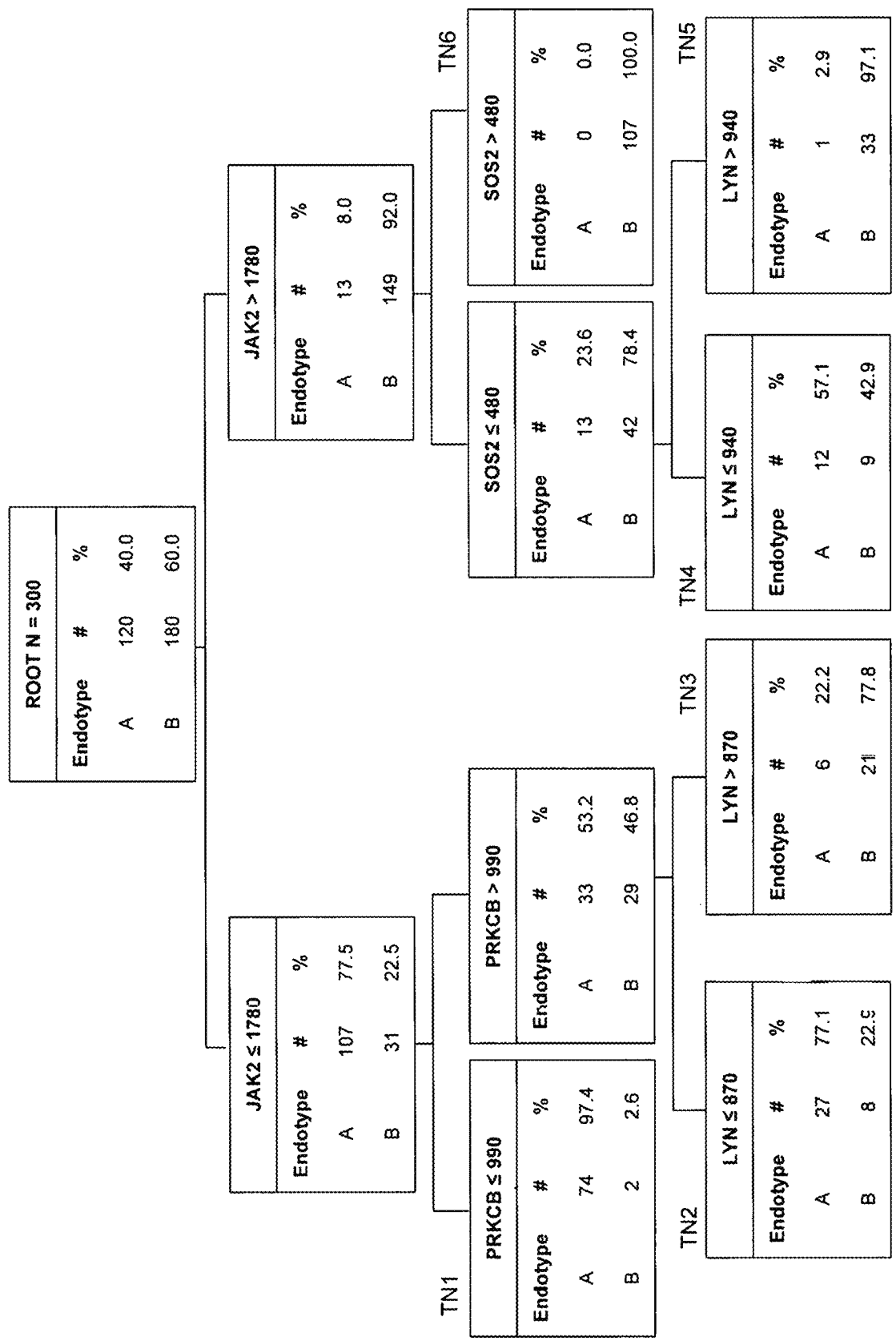
FIG. 1 depicts decision tree #1, derived from model #1, including the genes JAK1, PRKCB, SOS2, and LYN. The gene expression values are provided in arbitrary units of mRNA counts, as generated by the NanoString nCounter platform and normalized to four housekeeping genes.

All references cited herein are incorporated by reference in their entirety. Also incorporated herein by reference in their entirety include: United States Patent Application No. 61/595,996, BIOMARKERS OF SEPTIC SHOCK, filed on Feb. 7, 2012; U.S. Provisional Application No. 61/721,705, A MULTI-BIOMARKER-BASED OUTCOME RISK STRATIFICATION MODEL FOR ADULT SEPTIC SHOCK, filed on Nov. 2, 2012; International Patent Application No. PCT/US13/25223, A MULTI-BIOMARKER-BASED OUTCOME RISK STRATIFICATION MODEL FOR PEDIATRIC SEPTIC SHOCK, filed on Feb. 7, 2013; International Patent Application No. PCT/US13/25221, A MULTI-BIOMARKER-BASED OUTCOME RISK STRATIFICATION MODEL FOR ADULT SEPTIC SHOCK, filed on Feb. 7, 2013; U.S. Provisional Application No. 61/908,613, TEMPORAL PEDIATRIC SEPSIS BIOMARKER RISK MODEL, filed on Nov. 25, 2013; and International Patent Application No. PCT/US14/067438, TEMPORAL PEDIATRIC SEPSIS BIOMARKER RISK MODEL, filed on Nov. 25, 2014.

Unless otherwise noted, terms are to be understood according to conventional usage by those of ordinary skill in the relevant art.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "monitoring" with reference to septic shock refers to a method or process of determining the severity or degree of septic shock or stratifying septic shock based on risk and/or probability of mortality. In some embodiments, monitoring relates to a method or process of determining the therapeutic efficacy of a treatment being administered to a patient.

As used herein, "outcome" can refer to an outcome studied. In some embodiments, "outcome" can refer to 28-day survival/mortality. The importance of survival/mortality in the context of pediatric septic shock is readily evident. The common choice of 28 days was based on the fact that 28-day mortality is a standard primary endpoint for interventional clinical trials involving critically ill patients. In some embodiments, an increased risk for a poor outcome indicates that a therapy has had a poor efficacy, and a reduced risk for a poor outcome indicates that a therapy has had a good efficacy.

As used herein, "outcome" can also refer to resolution of organ failure after 14 days or 28 days or limb loss. Although mortality/survival is obviously an important outcome, survivors have clinically relevant short- and long-term morbidities that impact quality of life, which are not captured by the dichotomy of "alive" or "dead." In the absence of a formal, validated quality of life measurement tool for survivors of pediatric septic shock, resolution of organ failure can be used as a secondary outcome measure. For example, the presence or absence of new organ failure over one or more timeframes can be tracked. Patients having organ failure beyond 28 days are likely to survive with significant morbidities having negative consequences for quality of life. Organ failure is generally defined based on published and well-accepted criteria for the pediatric population (Goldstein, B. et al. *Pediatr. Crit. Care Med.* 6:2-8 (2005)). Specifically, cardiovascular, respiratory, renal, hepatic, hematologic, and neurological failure can be tracked. In addition, limb loss can be tracked as a secondary outcome. Although limb loss is not a true "organ failure," it is an important consequence of pediatric septic shock with obvious impact on quality of life.

As used herein, "outcome" can also refer to complicated course. Complicated course as defined herein relates to persistence of two or more organ failures at day seven of septic shock or 28-day mortality.

As used herein, the terms "predicting outcome" and "outcome risk stratification" with reference to septic shock refers to a method or process of prognosticating a patient's risk of a certain outcome. In some embodiments, predicting an outcome relates to monitoring the therapeutic efficacy of a treatment being administered to a patient. In some embodiments, predicting an outcome relates to determining a relative risk of an adverse outcome (e.g. complicated course) and/or mortality. In some embodiments, the predicted outcome is associated with administration of a particular treatment or treatment regimen. Such adverse outcome risk can be high risk, moderate risk, moderate-high risk, moderate-low risk, or low risk. Alternatively, such adverse outcome risk can be described simply as high risk or low risk, corresponding to high risk of adverse outcome (e.g. complicated course) and/or mortality probability, or high likelihood of therapeutic effectiveness, respectively. In some embodiments of the present invention, adverse outcome risk can be determined via the biomarker-based endotyping strategy described herein. In some embodiments, predicting an outcome relates to determining a relative risk of mortality. Such mortality risk can be high risk, moderate risk, moderate-high risk, moderate-low risk, or low risk. Alternatively, such mortality risk can be described simply as high risk or low risk, corresponding to high risk of death or high likelihood of survival, respectively. As related to the terminal nodes of the decision trees described herein, a "high risk terminal node" corresponds to an increased probability of adverse outcome (e.g. complicated course) and/or mortality according to a particular treatment or treatment regimen, whereas a "low risk terminal node" corresponds to a decreased probability of adverse outcome (e.g. complicated course) and/or mortality according to a particular treatment or treatment regimen.

As used herein, the term "high risk clinical trial" refers to one in which the test agent has "more than minimal risk" (as defined by the terminology used by institutional review boards, or IRBs). In some embodiments, a high risk clinical trial is a drug trial.

As used herein, the term "low risk clinical trial" refers to one in which the test agent has "minimal risk" (as defined by the terminology used by IRBs). In some embodiments, a low risk clinical trial is one that is not a drug trial. In some embodiments, a low risk clinical trial is one that that involves the use of a monitor or clinical practice process. In some embodiments, a low risk clinical trial is an observational clinical trial.

As used herein, the terms "modulated" or "modulation," or "regulated" or "regulation" and "differentially regulated" can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "subject" refers to any member of the animal kingdom. In some embodiments, a subject is a human patient. In some embodiments, a subject is a pediatric patient. In some embodiments, a pediatric patient is a patient under 18 years of age, while an adult patient is 18 or older.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c)

relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, the term "expression levels" refers, for example, to a determined level of biomarker expression. The term "pattern of expression levels" refers to a determined level of biomarker expression compared either to a reference (e.g. a housekeeping gene or inversely regulated genes, or other reference biomarker) or to a computed average expression value (e.g. in DNA-chip analyses). A pattern is not limited to the comparison of two biomarkers but is more related to multiple comparisons of biomarkers to reference biomarkers or samples. A certain "pattern of expression levels" can also result and be determined by comparison and measurement of several biomarkers as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

As used herein, the term "decision tree" refers to a standard machine learning technique for multivariate data analysis and classification. Decision trees can be used to derive easily interpretable and intuitive rules for decision support systems.

As used herein, the term "normalized mRNA counts" refers to NanoString-derived expression data normalized against the four housekeeping genes: 3-2-microglobulin, folylpolyglutamate synthase, 2,4-dienoyl coenzyme A reductase 1, and peptidylprolyl isomerase B, based on the geometric mean of the housekeeping genes (see Wong et al., Am J Respir Crit Care Med 2015, 191(3):309-315).

Determining Patient Endotype

The intrinsic heterogeneity of septic shock implies the existence of distinct subgroups that can be classified by pathobiological mechanism or treatment response. Such subgroups are known as endotypes.

The researchers of the present invention have previously identified two subclasses of pediatric septic shock based on genome-wide expression profiling [2]. Subsequently, a classification system was derived based on computer-assisted image analysis of gene expression mosaics representing 100 genes [3-5]. The 100-gene signature is provided in Table 1 below.

TABLE 1

List of 100 septic shock subclass-defining genes.

| Gene Symbol | Genbank | Description |
| --- | --- | --- |
| APAF1 | NM_013229 | apoptotic peptidase activating factor 1 |
| ARPC5 | AL516350 | actin related protein 2/3 complex, subunit 5, 16 kDa |
| ASAH1 | BC016828 | N-acylsphingosine amidohydrolase (acid ceramidase) 1 |
| ATP2B2 | U15688 | ATPase, Ca++ transporting, plasma membrane 2 |
| BCL6 | NM_001706 | B-cell CLL/lymphoma 6 |
| BMPR2 | AL046696 | bone morphogenetic protein receptor, type II (serine/threonine kinase) |
| BTK | NM_000061 | Bruton agammaglobulinemia tyrosine kinase |
| CAMK2D | AA777512 | calcium/calmodulin-dependent protein kinase (CaM kinase) II delta |
| CAMK2G | AA284757 | calcium/calmodulin-dependent protein kinase (CaM kinase) II gamma |
| CAMK4 | AL529104 | calcium/calmodulin-dependent protein kinase IV |
| CASP1 | AI719655 | caspase 1, apoptosis-related cysteine peptidase (interleukin 1, beta, convertase) |
| CASP2 | AU153405 | caspase 2, apoptosis-related cysteine peptidase |
| CASP4 | U25804 | caspase 4, apoptosis-related cysteine peptidase |
| CASP8 | BF439983 | caspase 8, apoptosis-related cysteine peptidase |
| CD247 | J04132 | CD247 molecule |
| CD3E | NM_000733 | CD3e molecule, epsilon (CD3-TCR complex) |
| CD3G | NM_000073 | CD3g molecule, gamma (CD3-TCR complex) |
| CD79A | M74721 | CD79a molecule, immunoglobulin-associated alpha |
| CREB1 | NM_004379 | cAMP responsive element binding protein 1 |
| CREB5 | NM_004904 | cAMP responsive element binding protein 5 |
| CSNK1A1 | AV704610 | Casein kinase 1, alpha 1 |
| CTNNB1 | AF130085 | catenin (cadherin-associated protein), beta 1, 88 kDa |
| DAPP1 | NM_014395 | dual adaptor of phosphotyrosine and 3-phosphoinositides |
| DBT | AI632010 | dihydrolipoamide branched chain transacylase E2 |
| EP300 | AI459462 | E1A binding protein p300 |
| FAS | X83493 | Fas (TNF receptor superfamily, member 6) |
| FCGR2A | NM_021642 | Fc fragment of IgG, low affinity IIa, receptor (CD32) |
| FCGR2C | U90939 | Fc fragment of IgG, low affinity IIc, receptor for (CD32) |
| FYN | S74774 | FYN oncogene related to SRC, FGR, YES |
| GK | NM_000167 | glycerol kinase |
| GNAI3 | J03005 | guanine nucleotide binding protein (G protein), alpha inhibiting activity polypeptide 3 |
| HDAC4 | NM_006037 | histone deacetylase 4 |
| HLA-DMA | X76775 | major histocompatibility complex, class II, DM alpha |
| HLA-DOA | AL581873 | major histocompatibility complex, class II, DO alpha |
| ICAM3 | NM_002162 | intercellular adhesion molecule 3 |

TABLE 1-continued

List of 100 septic shock subclass-defining genes.

| Gene Symbol | Genbank | Description |
|---|---|---|
| IL1A | NM_000575 | interleukin 1, alpha |
| INPP5D | BC027960 | inositol polyphosphate-5-phosphatase, 145 kDa |
| ITGAM | NM_000632 | integrin, alpha M (complement component 3 receptor 3 subunit) |
| ITGAV | AI093579 | integrin, alpha V (vitronectin receptor, alpha polypeptide, antigen CD51) |
| ITGAX | M81695 | integrin, alpha X (complement component 3 receptor 4 subunit) |
| JAK1 | AL039831 | Janus kinase 1 (a protein tyrosine kinase) |
| JAK2 | NM_004972 | Janus kinase 2 (a protein tyrosine kinase) |
| KAT2B | AV735100 | K(lysine) acetyltransferase 2B |
| LAT2 | AF257135 | linker for activation of T cells family, member 2 |
| LYN | AI356412 | v-yes-1 Yamaguchi sarcoma viral related oncogene homolog |
| MAP2K4 | NM_003010 | mitogen-activated protein kinase kinase 4 |
| MAP3K1 | AA541479 | mitogen-activated protein kinase kinase 1 |
| MAP3K3 | BG231756 | mitogen-activated protein kinase kinase 3 |
| MAP3K5 | NM_005923 | mitogen-activated protein kinase kinase 5 |
| MAP3K7 | NM_003188 | mitogen-activated protein kinase kinase 7 |
| MAP4K1 | BE646618 | mitogen-activated protein kinase kinase kinase kinase 1 |
| MAP4K4 | AL561281 | mitogen-activated protein kinase kinase kinase kinase 4 |
| MAPK1 | AA129773 | mitogen-activated protein kinase 1 |
| MAPK14 | AF100544 | mitogen-activated protein kinase 14 |
| MDH1 | AW952547 | Malate dehydrogenase 1, NAD (soluble) |
| MKNK1 | BC002755 | MAP kinase interacting serine/threonine kinase 1 |
| NCOA2 | AU145806 | Nuclear receptor coactivator 2 |
| NCR3 | AF031136 | natural cytotoxicity triggering receptor 3 |
| NFATC1 | NM_006162 | nuclear factor of activated T-cells, cytoplasmic, calcineurin-dependent 1 |
| PAK2 | AA287921 | p21 protein (Cdc42/Rac)-activated kinase 2 |
| PDPR | BE644918 | pyruvate dehydrogenase phosphatase regulatory subunit |
| PIAS1 | NM_016166 | protein inhibitor of activated STAT, 1 |
| PIK3C2A | AA579047 | Phosphoinositide-3-kinase, class 2, alpha polypeptide |
| PIK3C3 | NM_002647 | phosphoinositide-3-kinase, class 3 |
| PIK3CA | AA767763 | Phosphoinositide-3-kinase, catalytic, alpha polypeptide |
| PIK3CD | U86453 | phosphoinositide-3-kinase, catalytic, delta polypeptide |
| PIK3R1 | AI679268 | phosphoinositide-3-kinase, regulatory subunit 1 (alpha) |
| PLCG1 | AL022394 | phospholipase C, gamma 1 |
| POU2F2 | AA805754 | POU class 2 homeobox 2 |
| PPP1R12A | AI817061 | protein phosphatase 1, regulatory (inhibitor) subunit 12A |
| PPP2R2A | AI934447 | protein phosphatase 2 (formerly 2A), regulatory subunit B, alpha isoform |
| PPP2R5C | AL834350 | protein phosphatase 2, regulatory subunit B', gamma isoform |
| PRKAR1A | AI682905 | protein kinase, cAMP-dependent, regulatory, type I, alpha (tissue specific extinguisher 1) |
| PRKCB | M13975 | protein kinase C, beta |
| PSMB7 | AI248671 | Proteasome (prosome, macropain) subunit, beta type, 7 |
| PTEN | BC005821 | phosphatase and tensin homolog |
| PTPRC | NM_002838 | protein tyrosine phosphatase, receptor type, C |
| RAF1 | BI496583 | V-raf-1 murine leukemia viral oncogene homolog 1 |
| RHOT1 | NM_018307 | ras homolog gene family, member T1 |
| ROCK1 | N22548 | Rho-associated, coiled-coil containing protein kinase 1 |
| SEMA4F | AF119878 | sema domain, immunoglobulin domain (Ig), transmembrane domain (TM) and short cytoplasmic domain, (semaphorin) 4F |
| SEMA6B | NM_020241 | sema domain, transmembrane domain (TM), and cytoplasmic domain, (semaphorin) 6B |
| SMAD4 | AL832789 | SMAD family member 4 |
| SOS1 | AW241962 | son of sevenless homolog 1 (*Drosophila*) |
| SOS2 | L20686 | son of sevenless homolog 2 (*Drosophila*) |
| SP1 | BG431266 | Sp1 transcription factor |
| TAF11 | BQ709323 | TAF11 RNA polymerase II, TATA box binding protein (TBP)-associated factor, 28 kDa |
| TBK1 | NM_013254 | TANK-binding kinase 1 |
| TGFBR1 | AV700621 | Transforming growth factor, beta receptor 1 |
| TLE4 | AL358975 | transducin-like enhancer of split 4 (E(sp1) homolog, *Drosophila*) |
| TLR1 | AL050262 | toll-like receptor 1 |
| TLR2 | NM_003264 | toll-like receptor 2 |
| TLR8 | AW872374 | toll-like receptor 8 |
| TNFSF10 | AW474434 | tumor necrosis factor (ligand) superfamily, member 10 |
| TRA@ | L34703 | T cell receptor alpha locus |
| TYROBP | NM_003332 | TYRO protein tyrosine kinase binding protein |
| UBE3A | AF037219 | Ubiquitin protein ligase E3A |
| USP48 | NM_018391 | ubiquitin specific peptidase 48 |
| ZAP70 | AI817942 | zeta-chain (TCR) associated protein kinase 70 kDa |
| ZDHHC17 | AI621223 | zinc finger, DHHC-type containing 17 |

The subclasses have important differences with respect to mortality, organ failure burden, and treatment response [5, 6]. Given these differences, and because the classifier genes reflect adaptive immunity and the glucocorticoid receptor signaling pathway, these subclasses can represent endotypes of pediatric septic shock which differ with respect to outcome and treatment response. Assigning patients to an endotype can therefore enable precision critical care medicine.

Identification of these endotypes can identify patients who are more likely to respond and/or who are candidates for to a certain type of treatment, such as, for example, immune enhancing therapies or corticosteroids, and the like. As described herein, the present researchers have demonstrated that prescription of corticosteroids was independently associated with increased odds of mortality in one of the two endotypes [5]. In a separate analysis, endotype assignment was combined with risk stratification to identify a subgroup of patients in whom prescription of corticosteroids was associated with improved outcomes [6].

Endotype assignment based on computer-assisted image analysis of a 100-gene expression signature is theoretically achievable, but is currently impractical and cannot be used in the context of critically ill patients with septic shock for whom decision-making is highly time-sensitive [7]. There is therefore a need for an effective endotyping strategy based on a much smaller number of genes, which can readily translate into a clinical test amenable to decision making in this patient population. In order to accomplish such an effective endotyping strategy, the existing 100 endotype-defining genes need to be reduced into a much smaller subset needed to accurately differentiate endotypes, with the subset preferably containing a minimum number of genes needed to accurately differentiate endotypes. However, such an endotyping strategy based on a smaller number of genes does not currently exist and has heretofore not been readily elucidated, given the high level of biological complexity.

As described herein, Classification and Regression Tree (CART) methodology was used to reduce the existing 100 endotype-defining genes into very small subsets of four genes, which can accurately differentiate endotypes in order to derive a simplified and clinically applicable biomarker-based endotyping strategy. Ten-fold cross validation was used to assess model fit. Via this CART-based approach, the septic shock endotyping strategy was successfully reduced to decision trees consisting of just four genes.

For example, decision tree #1, derived from model #1 (consisting of the four genes JAK, LYN, PRKCB, and SOS2) as described herein and shown in FIG. 1, had an area under the receiver operating curve (AUROC) of 0.97 (95% CI: 0.95 to 0.99). The diagnostic test characteristics of decision tree #1 included a positive likelihood ratio of 8.9 (95% CI: 5.8 to 13.7) and a negative likelihood ratio of 0.07 (95% CI: 0.03 to 0.13) for identifying endotype A, leading to excellent test characteristics for distinguishing endotype A from endotype B. Allocation to endotype A was associated with increased odds of poor outcome, and corticosteroid prescription was associated with increased odds of mortality among endotype A subjects, but not endotype B subjects. These associations were evident after adjusting for illness severity and age, and are consistent with previous observations [5]. The four genes in decision tree #1 correspond to signaling pathways and a gene network relevant to septic shock biology.

While the four-gene model in decision tree #1 leads to reclassification of some patients, the identical phenotypes listed above were observed when the derivation and test cohort subjects were combined, despite the reclassifications. Accordingly, the four-gene decision tree #1, consisting of JAK, LYN, PRKCB, and SOS2, fully reproduces the three phenotypic features seen when classifying patients using all 100 genes. This result is biologically important and fundamental for the concept of endotyping.

These data indicate that the septic shock endotyping strategy was successfully reduced to a decision tree consisting of just four genes. The decision tree has excellent test characteristics for distinguishing endotype A from endotype B in both the derivation and test cohorts, although there were some reclassifications of subjects relative to the original, reference criterion endotyping strategy. Despite these reclassifications, allocation to endotype A remained independently associated with increased odds of poor outcome, and corticosteroid prescription remained independently associated with increased odds of mortality among endotype A subjects.

A subsequent analysis was conducted to determine if alternative 4 gene models can also reproduce these three phenotypic features after reclassification. Alternative models #2-8 were used to generate alternative decision trees #2-8. However, none of the alternative models was able to replicate the mortality phenotype, i.e. after reclassification, an independent association between allocation to endotype A and increased odds of mortality was not observed. This in contrast to the result provided by decision tree #1, which was able to replicate the mortality phenotype.

In combination, these results indicate that the presently described simplified decision tree/biomarker-based endotyping strategy is reliable, particularly when model #1 is used. Its relative simplicity makes it amenable for robust and rapid identification of septic shock endotypes and therefore translatable to the critical care environment. This presents a tremendous advantage over the previous 100-gene expression signature, which cannot allow for robust and rapid identification of septic shock endotypes and is not applicable to the critical care environment.

As different subclasses of septic shock have been identified to have different biological activity, with respect to adaptive immunity and glucocorticoid receptor signaling, and differential response to corticosteroid administration, patients classified into the subgroup of patients with increased risk of adverse outcome when prescribed corticosteroids, i.e. endotype A patients as defined herein, can have improved outcomes when treated with non-corticosteroid therapies. Such non-corticosteroid therapies can include alternative therapies and/or high risk therapies. In particular, endotype A patients can be treated with immune enhancing therapies, such as, for example, GMCSF, interleukin-7, anti-PD-1, and the like.

The four genes in decision tree #1, derived from model #1, consist of two protein tyrosine kinases (JAK2 and LYIV), one serine- and threonine-specific protein kinase (PRKCB), and a guanine nucleotide exchange factor (SOS2). All four genes contribute to the GM-CSF signaling pathway. This is important because GM-CSF therapy is under consideration as an adjunctive therapy to prevent or treat sepsis [16-18]. The present data demonstrate that endotype A and B subjects are likely to have different responses to such an approach. Endotyping can therefore play an important role in predictive enrichment for any study of GM-CSF therapy.

Two of the genes (JAK2 and SOS2) correspond to the glucocorticoid receptor signaling pathway, in keeping with previous observations [2, 5]. The biological significance of this is indicated by an independent association between corticosteroid prescription and poor outcome among endotype A subjects, in whom the glucocorticoid receptor signaling pathway genes are repressed relative to the endotype B subjects. After decades of study, the role of adjunctive corticosteroids in septic shock remains controversial [19, 20]. It has heretofore been relatively unclear which patients stand to gain the most benefit from adjunctive corticosteroids [21]. The septic shock endotypes can identify patients with septic shock who are more likely to respond to adjunctive corticosteroids; this can be used to estimate corticosteroid responsiveness and therefore inform clinical trial design and even clinical care. In another recent post hoc analysis, it has been demonstrated that combining mortality risk stratification with endotype assignment can be used to identify a subgroup of patients most likely to benefit from corticosteroids (26).

The four genes also correspond to a gene network involved in cell-to-cell signaling and interaction, cellular development, and cellular growth and proliferation. The network contains highly connected nodes corresponding to the pleotropic protein kinases AKT, ERK1/2, and JNK. All three protein kinases have been linked to sepsis-related biology and inflammation [22, 23]. The network is also subject to regulation by miRNA 126a-5p. In a recent report, Fan and colleagues demonstrated in an experimental model of sepsis that endothelial progenitor cells improved vascular function in a manner partially dependent on miRNA 126-5p [24]. These investigators also reported a similar role for miRNA 126-5p in a lipopolysaccharide model of acute lung injury [25].

There is a group of patients in whom differentiation between endotype A and endotype B remains challenging, classified as terminal node four in decision tree #1 described herein. This can be indicative of a septic shock subgroup belonging to third endotype, endotype C. The secondary analysis is limited by the small number of patients allocated to the putative endotype C.

Accordingly, a simplified strategy for identifying septic shock endotypes has been derived. In particular, decision tree #1, derived from model #1 based on a panel of four biomarkers, namely JAK2, LYN, PRKCB, and SOS2, has been demonstrated to be the most effective of the gene combinations evaluated herein. This simplified strategy is amenable to translation to the bedside of critically ill patients, which heretofore has not been possible given the complexity of the previously identified 100-gene signature.

In a subsequent study, the 100 endotyping genes were measured at day 1 and day 3 of illness in 375 patients to determine if endotype assignment changes over time, and whether changing endotype is associated with corticosteroid response and outcomes. Multivariable logistic regression was used to adjust for illness severity, age, and comorbidity burden. Among the 132 subjects assigned to endotype A on day 1, 56 (42%) transitioned to endotype B by day 3. Among 243 subjects assigned to endotype B on day 1, 77 (32%) transitioned to endotype A by day 3. Assignment to endotype A on day 1 was associated with increased odds of mortality. This risk was modified by the subsequent day 3 endotype assignment. Corticosteroids were associated with increased risk of mortality among subjects who persisted as endotype A. Therefore, a substantial proportion of children with septic shock were found to transition endotypes during the acute phase of illness. The risk of poor outcome and the response to corticosteroids change with changes in endotype assignment. Patients persisting as endotype A are at highest risk of poor outcomes. This subsequent study is described in Wong et al., *Crit Care Med*, 46:e242-e249, March 2018; this document is incorporated by reference herein in its entirety, and for all purposes.

In conclusion, a biomarker-based endotyping strategy has been derived, tested, and validated. This biomarker-based endotyping strategy can be used to stratify patients, to determine an appropriate therapy, or to monitor the therapeutic efficacy of a treatment being administered to a patient with septic shock. This biomarker-based endotyping strategy can be used as an adjunct to physiological assessment for selecting an appropriate therapeutic intervention or monitoring the efficacy of a therapeutic intervention in children with septic shock, where risk of adverse outcome is minimized, or to serve as a surrogate outcome variable in clinical trials.

Determining Mortality Risk

Reliable risk stratification has numerous clinical applications. These include better-informed allocation of critical care resources, appropriate selection of patients for higher risk and more costly therapies, and for benchmarking outcomes. Additionally, risk stratification can serve as a prognostic enrichment tool to greatly enhance efficiency of clinical trials (27). Reliable risk stratification of patients with septic shock can be a challenging task due to significant patient heterogeneity (1).

The Pediatric Sepsis Biomarker Risk Model (PERSEVERE) for estimating baseline mortality risk in children with septic shock was previously derived and validated (28-30). PERSEVERE is based on a panel of 12 serum protein biomarkers measured from blood samples obtained during the first 24 hours of a septic shock diagnosis, selected from among 80 genes having an association with mortality risk in pediatric septic shock.

The PERSEVERE biomarkers were initially identified through discovery-oriented transcriptomic studies searching for genes having an association with mortality in pediatric septic shock (38, 32). From among the 80 genes identified in these studies, the biomarkers to be considered for inclusion in PERSEVERE were selected using two simultaneous criteria. First, the gene should have a biologically plausible link to septic shock pathophysiology. Second, the protein transcribed from the gene can be readily measured in the blood compartment. While pragmatic, the selection criteria were limited by existing knowledge and paradigms of septic shock pathophysiology, and by technical considerations, leaving just 12 potential biomarkers for consideration. Consequently, 68 genes were left unconsidered, some of which might have the ability to improve upon the ability of PERSEVERE to estimate baseline mortality risk, and some of which might provide information about biological mechanisms and pathophysiology associated with mortality in septic shock.

As described herein, a study was conducted to determine whether the previously unconsidered 68 mortality risk assessment genes have the potential to improve the accuracy of PERSEVERE for estimating baseline mortality risk, as well as explore whether there are previously unconsidered mechanistic pathways of importance in septic shock outcomes, to provide biological information regarding the pathophysiology of septic shock. The resulting risk stratification mode is called PERSEVERE-XP, reflecting the integration of PERSEVERE with gene expression data.

In this analysis, the number of variables was reduced by determining the biological linkage of the 68 previously unconsidered genes. The genes identified through variable reduction were combined with the PERSEVERE-based mortality probability/mortality risk to derive a risk stratification model for 28-day mortality using Classification and Regression Tree methodology (n=307). The derived tree, PERSEVERE-XP, was then tested in a separate cohort (n=77).

Variable reduction revealed a network consisting of 18 mortality risk assessment genes related to tumor protein 53 (TP53). In the derivation cohort, PERSEVERE-XP had an area under the receiver operating characteristic curve (AUC) of 0.90 (95% CI.: 0.85 to 0.95) for differentiating between survivors and non-survivors. In the test cohort, the AUC was 0.96 (95% C.I.: 0.91 to 1.0). The AUC of PERSEVERE-XP was superior to that of PERSEVERE and the Pediatric Risk of Mortality-III (PRISM-III) score.

In summary, PERSEVERE was combined with previously unconsidered genes having predictive capacity for mortality to provide an improved risk stratification tool for pediatric septic shock. PERSEVERE-XP combines protein and mRNA biomarkers to provide clinically useful risk stratification. PERSEVERE-XP significantly improves upon PERSEVERE and shows a role for TP53-related cellular division, repair, and metabolism in the pathophysiology of septic shock.

PERSEVERE-XP demonstrates clinically relevant levels of performance upon testing. Direct comparisons of PERSEVERE-XP and PERSEVERE showed unambiguous improvements in the ability to accurately estimate baseline mortality risk. Notably, both the positive and the negative likelihood ratios of PERSEVERE-XP have clinical utility for identifying children with septic shock at both high and low risk for mortality, respectively. Even when PERSEVERE-XP incorrectly classified a subject as a non-survivor, it nonetheless identified subjects with greater illness severity based on PRISM-III score, organ failure burden, and duration of intensive care unit admission. This likely reflects, in part, subjects who were indeed at higher risk of mortality but in whom the risk was modified by clinical interventions.

The biological approach to variable reduction led consideration of a group of TP53-related genes for the derivation of PERSEVERE-XP. TP 53l is a pleiotropic transcription factor, best known to function as a tumor suppressor because it is induced by DNA damage and subsequently orchestrates cell cycle arrest, thus enabling cells with the opportunity to repair the damage (37). Alternatively, when the damage is irreparable, TP53 can drive a cell toward apoptosis. The result in either scenario is preventing the generation and persistence of cells with genomic damage. It is now apparent that TP53 modulates cellular fate and function well beyond oncogenesis and cell cycle arrest. For example, TP53 can modulate cellular metabolism (38), autophagy (39), redox homeostasis (40-42), cross-talk with the NF-КB pathway (37, 38, 43), inflammation (37, 44), and lymphocyte apoptosis during experimental sepsis (45). In a murine model of lipopolysaccharide-induced lung injury, administration of a pharmacologic inducer of TP53 stabilization reduced the severity of lung injury (46). TP53 also interacts directly with the glucocorticoid receptor (47). All of these biological processes are relevant to sepsis pathophysiology. While TP53 itself does not appear to be differentially expressed between survivors and non-survivors of pediatric septic shock, it does appear to be generally repressed in septic shock relative to healthy controls, supporting its putative role in sepsis.

PERSEVERE-XP contains four genes directly related to TP53: DDIT4, HAL, PRCJ, and ZWINT. PRC1 has an important role in organizing the central spindle essential for cytokinesis (48, 49). PRC1 expression is directly regulated by TP53 (50), and it serves as a substrate for cyclin dependent kinases (51). Cyclin B and cyclin dependent kinase 1 are among the 68 mortality risk assessment genes shown in Table 12. In a functionally related manner, ZWINT plays a role in mitosis and the mitotic checkpoint through its interactions with the kinetochore (52, 53). ZWINT is linked to TP53 via its direct interactions with NDC80, which is also included among the 68 mortality risk assessment genes.

HAL catalyzes the first step in histidine metabolism and mutations of HAL lead to the metabolic disease, histidemia, characterized by high systemic levels of histidine (54). Its expression is directly regulated by forkhead box O1 (FOXO1), which is in turn regulated by TP53. In contrast to the other three genes contributing to PERSEVERE-XP, HAL expression is decreased in the non-survivors relative to the survivors. Consistent with this observation, histidine has been shown to be one of the metabolites significantly increased in the serum compartment of children with septic shock relative to healthy controls and critically ill children without sepsis (55).

DDIT4, also known as REDD1 (regulated in development and DNA damage 1), plays an important role in energy homeostasis by serving as a modulator of insulin action (56) and of skeletal muscle metabolism (57). DDIT4 is directly regulated by TP53 and has been shown to regulate skeletal muscle protein synthesis and autophagy during experimental murine sepsis via the mechanistic target of rapamycin complex 1 (mTORC1) (58). In addition, DDIT4/REDD1 appears to play a direct role in corticosteroid-induced skeletal muscle atrophy (59). This is relevant when considering the ongoing controversies surrounding the role of corticosteroids in septic shock (60).

The PERSEVERE biomarkers are generally associated with inflammation and cellular injury. These associations are well aligned with existing paradigms of poor outcome from septic shock (31). However, therapies based on these paradigms have not led to clear improvements in patient outcomes, highlighting the need to expand the knowledge of septic shock pathophysiology (1). Accordingly, PERSEVERE-XP illuminates the biological pathways that drive poor outcome from septic shock. PERSEVERE-XP indicates that dysfunctional, TP53-related cellular division, repair, and metabolism can also contribute to the pathophysiology of septic shock, in conjunction with dysfunctional inflammation. These concepts are biologically plausible and experimentally testable.

While current assay platforms are analytically reliable, they are not amenable to rapid data generation. The ideal risk stratification tool for septic shock should generate reliable biomarker data within a few hours to meet the time sensitive demands of decision making in this patient population. Thus, clinical application of PERSEVERE-XP will require the development of rapid analytical platforms for both protein and mRNA biomarkers. The necessary technologies for developing such platforms are available.

In summary, a pediatric septic shock risk stratification tool based a combination of protein and mRNA biomarkers was derived and successfully tested. PERSEVERE-XP adds significant predictive information to PERSEVERE and has clinical utility for identifying children with septic shock at both low and high risk of mortality. PERSEVERE-XP also indicates the link for TP53 and related genes to the biology of poor outcome in septic shock.

Combining Prognostic and Predictive Enrichment

The role of corticosteroids in septic shock remains controversial despite decades of study. The importance of identifying subgroups of children with septic shock who may benefit from corticosteroids is highlighted by the suggestion of harm associated with corticosteroids (5, 10, 63). In 2002, a landmark study was published (20) indicating that a corticotropin stimulation test could identify a subgroup of patients who benefit from corticosteroids. This approach embodied the concept of predictive enrichment but could not be replicated in a subsequent trial (19). This indicates that patient selection may be more complex than the information provided by corticotropin stimulation alone (21).

Prognostic and predictive enrichment strategies are fundamental tools for enhancing clinical trials and embracing precision medicine (61). Enrichment uses patient characteristics to select a study population in which a drug or intervention effect is more likely to be detected than in an unselected population. Prognostic enrichment strategies select patients with a greater likelihood of having a disease-related event. Predictive enrichment strategies select patients who are more likely to respond to an intervention or drug based on a biological or physiologic mechanism. Enrichment strategies are particularly effective when selecting patients for treatment trials in highly heterogeneous syndromes, such as septic shock.

Identifying children with septic shock who may benefit from corticosteroids remains a challenge. A prognostic and predictive enrichment strategy for pediatric septic shock has been developed to identify a pediatric septic shock subgroup responsive to corticosteroids (Wong et al., Crit Care Med 2016, 44:e1000-3). The prognostic enrichment strategy involves PERSEVERE, which uses a panel of protein biomarkers to estimate baseline mortality probability/mortality risk in children with septic shock (28); alternatively, the prognostic enrichment strategy can combine the protein biomarker panel of PERSEVERE with mRNA biomarkers to estimate baseline mortality probability in children with septic shock, as with PERSEVERE-XP, described herein. The predictive enrichment strategy is based on endotypes of pediatric septic shock which, based on the mRNA expression profiles of 100 genes, reflect adaptive immune function and the glucocorticoid receptor signaling pathway (5).

These putative enrichment strategies have been previously applied independently in children with septic shock. Using PERSEVERE as a prognostic enrichment variable, the hypothesis that the beneficial effects of corticosteroids are dependent on baseline mortality risk was tested (10). A beneficial effect of corticosteroids was not detected in any PERSEVERE-based mortality risk strata. In the examination of the predictive enrichment strategy based on septic shock endotypes, corticosteroids were found to be independently associated with a four-fold increased mortality risk in endotype A patients; endotype A is characterized by decreased expression of genes corresponding to the glucocorticoid receptor signaling pathway relative to endotype B (5). The prognostic and predictive enrichment strategies have been combined to determine whether there exists an identifiable group of children with septic shock who are more likely to benefit from corticosteroids.

In the current study, prognostic and predictive enrichment strategies were combined to identify a subgroup of children with septic shock having a higher likelihood of benefitting from corticosteroids. Among endotype B patients with an intermediate to high baseline PERSEVERE risk, corticosteroid exposure was associated with reduced risk of complicated course. Because intermediate to high risk patients have a greater event rate, it becomes more feasible to detect an effect of corticosteroids; this is the concept of prognostic enrichment. Second, because endotype B patients have higher expression of genes corresponding to the glucocorticoid receptor signaling pathway than endotype A patients, they can be more likely to respond to corticosteroids. This is the concept of predictive enrichment.

In this analysis, among the 300 subjects (described in (5)) included in the derivation and validation of the septic shock endotypes, 288 (96%) had PERSEVERE data and were included in the analysis. For prognostic enrichment, each study subject was assigned a baseline mortality probability using the pediatric sepsis biomarker risk model. For predictive enrichment, each study subject was allocated to one of two septic shock endotypes, based on a 100-gene signature reflecting adaptive immunity and glucocorticoid receptor signaling.

Among the 112 endotype A subjects, 49 subjects (44%) had a complicated course. Among the 176 endotype B subjects, 37 subjects (21%) had a complicated course. Fifty-one endotype A subjects (46%) and 101 endotype B subjects (57%) were exposed to corticosteroids. Among endotype A subjects, only the PERSEVERE risk category was associated with increased risk of complicated course although there was a trend toward increased risk of complicated course with increased PRISM score. Among endotype B subjects, PRISM and PERSEVERE risk category were independently associated with increased risk of complicated course. Corticosteroid exposure was not associated with decreased risk of complicated course in endotype B subjects at low PERSEVERE risk, but in those at intermediate to high PERSEVERE risk, corticosteroids were associated with more than a 10-fold reduction in the risk of a complicated course.

In conclusion, a combination of prognostic and predictive strategies based on serum protein and mRNA biomarkers can be used to identify a subgroup of children with septic shock who may be more likely to benefit from corticosteroids.

Additional Patient Information

The demographic data, clinical characteristics, and/or results from other tests or indicia of septic shock specific to a pediatric patient with septic shock can affect the patient's outcome risk. Accordingly, such demographic data, clinical characteristics, and/or results from other tests or indicia of septic shock can be incorporated into the methods described herein which allow for stratification of individual pediatric patients in order to determine the patient's outcome risk. Such demographic data, clinical characteristics, and/or results from other tests or indicia of septic shock can also be used in combination with the methods described herein which allow for stratification of individual pediatric patients in order to determine the patient's outcome risk.

Such pediatric patient demographic data can include, for example, the patient's age, race, gender, and the like. In some embodiments, the biomarker-based endotyping strategy and/or the mortality probability stratification strategy described herein can incorporate or be used in combination with the patient's age, race, and/or gender to determine an outcome risk.

Such patient clinical characteristics and/or results from other tests or indicia of septic shock can include, for example, the patient's co-morbidities and/or septic shock causative organism, and the like.

Patient co-morbidities can include, for example, acute lymphocytic leukemia, acute myeloid leukemia, aplastic anemia, atrial and ventricular septal defects, bone marrow transplantation, caustic ingestion, chronic granulomatous disease, chronic hepatic failure, chronic lung disease, chronic lymphopenia, chronic obstructive pulmonary disease (COPD), congestive heart failure (NYHA Class IV CHF), Cri du Chat syndrome, cyclic neutropenia, developmental delay, diabetes, DiGeorge syndrome, Down syndrome, drowning, end stage renal disease, glycogen storage disease type 1, hematologic or metastatic solid organ malignancy, hemophagocytic lymphohistiocytosis, hepatoblastoma, heterotaxy, hydrocephalus, hypoplastic left heart syndrome, IPEX Syndrome, kidney transplant, Langerhans cell histiocytosis, liver and bowel transplant, liver failure, liver transplant, medulloblastoma, metaleukodystrophy, mitochondrial disorder, multiple congenital anomalies, multi-visceral transplant, nephrotic syndrome, neuroblastoma, neuromuscular disorder, obstructed pulmonary veins, Pallister Killian syndrome, Prader-Willi syndrome, requirement for chronic dialysis, requirement for chronic steroids, retinoblastoma, rhabdomyosarcoma, rhabdosarcoma, sarcoma, seizure disorder, severe combined immune deficiency, short gut syndrome, sickle cell disease, sleep apnea, small bowel transplant, subglottic stenosis, tracheal stenosis, traumatic brain injury, trisomy 18, type 1 diabetes mellitus, unspecified brain tumor, unspecified congenital heart disease, unspecified leukemia, VATER Syndrome, Wilms tumor, and the like. Any one or more of the above patient co-morbidities can be indicative of the presence or absence of chronic disease in the patient.

Septic shock causative organisms can include, for example, *Acinetobacter baumannii*, Adenovirus, *Bacteroides* species, *Candida* species, *Capnotyophaga jenuni*, *Cytomegalovirus*, *Enterobacter cloacae*, *Enterococcus faecalis*, *Escherichia coli*, Herpes simplex virus, Human metapneumovirus, Influenza A, *Klebsiella pneumonia*, *Micrococcus* species, mixed bacterial infection, *Moraxella catarrhalis*, *Neisseria meningitides*, Parainfluenza, *Pseudomonas* species, *Serratia marcescens*, *Staphylococcus aureus*, *Streptococcus agalactiae*, *Streptococcus milleri*, *Streptococcus pneumonia*, *Streptococcus pyogenes*, unspecified gram negative rods, unspecified gram positive cocci, and the like.

In some embodiments, the biomarker-based endotyping strategy and/or the mortality probability stratification strategy described herein can incorporate the patient's co-morbidities to determine an outcome risk and/or mortality probability. In some embodiments, the biomarker-based endotyping strategy and/or the mortality probability stratification strategy described herein can incorporate the patient's septic shock causative organism to determine an outcome risk and/or mortality probability.

In some embodiments, the biomarker-based endotyping strategy and/or the mortality probability stratification strategy described herein can be used in combination with the patient's co-morbidities to determine an outcome risk and/or mortality probability. In some embodiments, the biomarker-based endotyping strategy and/or the mortality probability stratification strategy described herein can be used in combination with the patient's septic shock causative organism to determine an outcome risk and/or mortality probability.

PERSEVERE and Other Population-Based Risk Scores

As mentioned previously, the PERSEVERE model for estimating baseline mortality risk in children with septic shock was previously derived and validated (28-30). PERSEVERE is based on a panel of 12 serum protein biomarkers measured from blood samples obtained during the first 24 hours of a septic shock diagnosis, selected from among 80 genes having an association with mortality risk in pediatric septic shock. Of those 12 serum biomarkers, the derived and validated PERSEVERE model is based on 5 specific biomarkers, namely CCL3, HSPA1B, IL8, GZMB, and MMP8. PERSEVERE additional takes patient age into account.

The PERSEVERE decision tree has 8 terminal nodes. Of these, 3 terminal nodes of the PERSEVERE decision tree are determined to be low risk/low mortality probability (terminal nodes 2, 4, and 7), while 5 terminal nodes of the PERSEVERE decision tree are determined to be intermediate to high risk/high mortality probability (terminal nodes 1, 3, 5, 6, and 8) (28-30). In some embodiments, the low risk/low mortality probability terminal nodes have a mortality probability between 0.000 and 0.025, while the intermediate to high risk/high mortality probability terminal nodes have a mortality probability greater than 0.025.

The low mortality probability terminal nodes are associated with: non-elevated levels of CCL3 and HSPA1B, and a non-highly elevated level of IL8; or an elevated level of CCL3, and non-elevated levels of IL8 and MMP8; or elevated levels of CCL3 and IL8, a non-elevated level of GZMB, and a patient age greater than 0.5 years. The intermediate and high mortality probability terminal nodes are associated with: non-elevated levels of CCL3 and HSPA1B, and a non-highly elevated level of IL8; or an elevated level of CCL3, and non-elevated levels of IL8 and MMP8; or elevated levels of CCL3 and IL8, a non-elevated level of GZMB, and a patient age greater than 0.5 years. In some embodiments, an elevated level of CCL3 corresponds to a serum CCL3 concentration greater than 160 pg/ml; an elevated level of HSPA1B corresponds to a serum HSPA1B concentration greater than 3.3 µg/ml; an elevated level of IL8 corresponds to a serum IL8 concentration greater than 507 pg/ml; a highly elevated level of IL8 corresponds to a serum IL8 concentration greater than 829 pg/ml; an elevated level of GZMB corresponds to a serum GZMB concentration greater than 55 pg/ml; and an elevated level of MMP8 corresponds to a serum MMP8 concentration greater than 47.5 ng/ml.

In some embodiments of the present invention, a patient sample is analyzed for the PERSEVERE serum protein biomarkers, as well as for the TP53 mRNA biomarkers, as described herein.

In some embodiments of the present invention, the PERSEVERE mortality probability stratification can be used in combination with a patient endotyping strategy, such as the endotyping strategy described herein involving two or more selected from the group consisting of JAK2, LYN, PRKCB, and SOS2, and the like. In some embodiments, the PERSEVERE-XP mortality probability stratification based on the PERSEVERE serum protein biomarkers and the TP53 mRNA biomarkers, as described herein, can be used in combination with a patient endotyping strategy, such as the endotyping strategy described herein involving two or more selected from the group consisting of JAK2, LYN, PRKCB, and SOS2, and the like. In some embodiments, the combination of a mortality probability stratification, such as PERSEVERE or PERSEVERE-XP, as described herein, with an endotyping strategy, such as the endotyping strategy described herein involving two or more selected from the group consisting of JAK2, LYN, PRKCB, and SOS2, can be used to determine an appropriate treatment regimen for a patient. For example, such combinations can be used to identify which patients are more likely to benefit from corticosteroids.

A number of additional models that generate mortality prediction scores based on physiological variables have been developed to date. These can include the PRISM, Pediatric Index of Mortality (PIM), and/pediatric logistic organ dysfunction (PELOD) models, and the like.

Such models can be very effective for estimating population-based outcome risks but are not intended for stratification of individual patients. The methods described herein which allow for stratification of individual patients can be used alone or in combination with one or more existing population-based risk scores.

In some embodiments, the biomarker-based endotyping strategy and/or the mortality probability stratification strategy described herein can be used with one or more additional population-based risk scores. In some embodiments, the biomarker-based endotyping strategy and/or the mortality probability stratification strategy described herein can be used in combination with PRISM. In some embodiments, the biomarker-based endotyping strategy and/or the mortality probability stratification strategy described herein can be used in combination with PIM. In some embodiments, the biomarker-based endotyping strategy and/or the mortality probability stratification strategy described herein can be used in combination with PELOD. In some embodiments, the biomarker-based endotyping strategy and/or the mortality probability stratification strategy described herein can be used in combination with a population-based risk score other than PRISM, PIM, and PELOD.

High Risk Therapies

High risk, invasive therapeutic and support modalities can be used to treat septic shock. The methods described herein which allow for the patient's outcome risk to be determined can help inform clinical decisions regarding the application of high risk therapies to specific pediatric patients, based on the patient's outcome risk.

High risk therapies include, for example, extracorporeal membrane oxygenation/life support, plasmapheresis, pulmonary artery catheterization, high volume continuous hemofiltration, and the like. High risk therapies can also include non-corticosteroid therapies, e.g. alternative therapies and/or high risk therapies. In particular, endotype A patients can be treated with immune enhancing therapies, such as, for example, GMCSF, interleukin-7, anti-PD-1, and the like.

In some embodiments, individualized treatment can be provided to a pediatric patient by selecting a pediatric patient classified as high risk by the methods described herein for one or more high risk therapies. In some embodiments, individualized treatment can be provided to a pediatric patient by excluding a pediatric patient classified as low risk from one or more high risk therapies.

Certain embodiments of the invention include using quantification data from a gene-expression analysis and/or from a mRNA analysis, from a sample of blood, urine, saliva, broncho-alveolar lavage fluid, or the like. Embodiments of the invention include not only methods of conducting and interpreting such tests but also include reagents, compositions, kits, tests, arrays, apparatuses, processing devices, assays, and the like, for conducting the tests. The compositions and kits of the present invention can include one or more components which enable detection of the biomarkers disclosed herein and combinations thereof (e.g. the combination of the four biomarkers JAK2, LYN, PRKCB, and SOS2) and can include, but are not limited to, primers, probes, cDNA, enzymes, covalently attached reporter molecules, and the like.

Diagnostic-testing procedure performance is commonly described by evaluating control groups to obtain four critical test characteristics, namely positive predictive value (PPV), negative predictive value (NPV), sensitivity, and specificity, which provide information regarding the effectiveness of the test. The PPV of a particular diagnostic test represents the proportion of positive tests in subjects with the condition of interest (i.e. proportion of true positives); for tests with a high PPV, a positive test indicates the presence of the condition in question. The NPV of a particular diagnostic test represents the proportion of negative tests in subjects without the condition of interest (i.e. proportion of true negatives); for tests with a high NPV, a negative test indicates the absence of the condition. Sensitivity represents the proportion of subjects with the condition of interest who will have a positive test; for tests with high sensitivity, a positive test indicates the presence of the condition in question. Specificity represents the proportion of subjects without the condition of interest who will have a negative test; for tests with high specificity, a negative test indicates the absence of the condition.

The threshold for the disease state can alternatively be defined as a 1-D quantitative score, or diagnostic cutoff, based upon receiver operating characteristic (ROC) analysis. The quantitative score based upon ROC analysis can be used to determine the specificity and/or the sensitivity of a given diagnosis based upon subjecting a patient to a decision tree described herein in order to predict an outcome for a pediatric patient with septic shock.

The correlations disclosed herein, between pediatric patient septic shock biomarker levels and/or mRNA levels and/or gene expression levels, provide a basis for conducting a diagnosis of septic shock, or for conducting a stratification of patients with septic shock, or for enhancing the reliability of a diagnosis of septic shock by combining the results of a quantification of a septic shock biomarker with results from other tests or indicia of septic shock, or for determining an appropriate treatment regimen for a pediatric patient with septic shock. For example, the results of a quantification of one biomarker could be combined with the results of a quantification of one or more additional biomarker, cytokine, mRNA, or the like. Thus, even in situations in which a given biomarker correlates only moderately or weakly with septic shock, providing only a relatively small PPV, NPV, specificity, and/or sensitivity, the correlation can be one indicium, combinable with one or more others that, in combination, provide an enhanced clarity and certainty of diagnosis. Accordingly, the methods and materials of the invention are expressly contemplated to be used both alone and in combination with other tests and indicia, whether quantitative or qualitative in nature.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Methods—Patient Endotyping Strategy

The methods used in examples 1-7 are summarized below:

Study Subjects.

A secondary analysis of previously published data [5] was conducted. The Institutional Review Boards of each of the 18 participating institutions approved the protocol for collection and use of biological specimens and clinical data.

Children ≤10 years of age admitted to a pediatric intensive care unit (PICU) and meeting pediatric-specific consensus criteria for septic shock were eligible for enrollment [8]. There were no exclusion criteria, other than the inability to obtain informed consent, which was obtained from parents or legal guardians. The consent allows for secondary analyses.

Blood samples were obtained within 24 hours of meeting criteria for septic shock. Clinical and laboratory data were collected daily while in the PICU. Organ failure data were tracked up to day seven of septic shock using previously published criteria [8]. Mortality was tracked for 28 days after enrollment. Illness severity was estimated using the Pediatric Risk of Mortality (PRISM) score [9]. Complicated course was defined as persistence of two or more organ failures at day seven of septic shock or 28-day mortality [5].

Corticosteroid prescription was at the discretion the clinical team caring for the study subjects. Corticosteroid exposure was treated as a binary variable, as previously described [10]. The medication fields of the clinical database were surveyed to determine if the study subjects received systemic corticosteroids. Subjects receiving any formulation of systemic corticosteroids during the first 7 days of meeting criteria for septic shock were classified as being exposed to corticosteroids. The one exception was subjects who received dexamethasone for less than 48 hours for airway edema. These subjects were classified as not being exposed to corticosteroids. All other subjects were classified as not being exposed to corticosteroids. It was not possible to consistently determine dosages or the clinical indications for corticosteroids in all subjects.

Multiplex mRNA Quantification.

The 100 endotype-defining genes and the 4 housekeeping genes were previously published, along with the gene expression quantification procedures [5]. Gene expression was measured using whole blood-derived RNA obtained within 24 hours of meeting criteria for septic shock. The NanoString nCounter™ (NanoString Technologies, Seattle, Wash.) and a custom-made code set were used. The technology is based on standard hybridization between the target gene, and target-specific capture and reporter probes [11]. All NanoString-based measurements were conducted at the University of Minnesota Genomics Center Core Facility.

Pathway Analysis.

The genes contributing to the derived decision tree were analyzed using the Ingenuity Pathway Analysis (IPA) platform (Ingenuity Systems, Redwood City, Calif.) [12, 13]. IPA is a database generated from peer-reviewed literature that provides a tool for discovery of signaling pathways and gene networks represented among uploaded gene lists.

CART Procedure and Statistical Analysis.

Salford Predictive Modeler v7.0 (Salford Systems, San Diego, Calif.) was used for the CART procedure [14, 15] to develop a decision tree to accurately predict assignment to endotype A or endotype B, using the smallest possible subset of genes from among the original 100. The primary outcome variable for the modeling procedures was allocation to endotype A as opposed to endotype B. For the purpose of this analysis, the criterion standard for endotype allocation was based on the original strategy using computer assisted image analysis of the 100 endotype defining genes [5]. The modeling procedure considered all 100 genes as candidate predictor variables and used the class probability method. Terminal nodes having less than 5% of the subjects in the root node and terminal nodes that did not improve classification were pruned. Weighting of cases and costs for misclassification were not used in the modeling procedures.

Ten-fold cross validation was used to estimate model performance. The code and data used to generate the model is available from the authors.

Other statistical procedures used SigmaStat Software (Systat Software, Inc., San Jose, Calif.). Initially, data are described using medians, interquartile ranges, frequencies, and percentages. Comparisons between groups used the Mann-Whitney U-test, Chisquare, or Fisher's Exact tests as appropriate. The performance of the decision tree for distinguishing endotypes was measured by constructing receiver operating characteristics curves and calculating diagnostic test characteristics. The association between subclass allocation, outcome, and corticosteroid prescription was modeled using multivariable logistic regression.

Example 2

Decision Tree #1

The clinical characteristics and demographics of the 300 subjects in the study cohort have been previously published [5]. There were 120 endotype A subjects (40%) and 180 endotype B subjects. FIG. 1 shows decision tree #1, derived from model #1, consisting of four genes: JAK2, PRKCB, SOS2, and LYN. Table 2 provides the annotations for the four genes in decision tree #1. The gene expression values are provided in arbitrary units of mRNA counts, as generated by the NanoString nCounter platform and normalized to four housekeeping genes. The root node provides the total number of subjects originally allocated to endotypes A and B, and their respective rates. Each daughter node provides the respective decision rule criterion based on a gene expression level, and the number of endotype A and B subjects, with the respective rates. Terminal nodes (TN) TN1, TN2, and TN4 contained subjects having a higher probability of being an endotype A (57.1 to 97.4%), whereas TN3, TN5, and TN6 contained subjects having a higher probability of being an endotype B (77.8 to 100%). The 10-fold cross validation procedure yielded an area under the receiver operating curve (AUROC) of 0.90.

TABLE 2

Annotations for the four genes in decision tree #1.

| Gene Symbol | Description | Entrez Gene ID |
|---|---|---|
| JAK2 | Janus kinase 2 | 3717 |
| LYN | LYN proto-oncogene, Src family tyrosine kinase | 4067 |
| PRKCB | Protein kinase C, beta | 5579 |
| SOS2 | SOS Ras/Rho guanine nucleotide exchange factor 2 | 6655 |

Using the original endotype classification strategy as the reference/criterion standard, the area under the receiver operating characteristic curve of decision tree #1 was 0.97 (95% CI: 0.95 to 0.99) for differentiating between endotypes A and B. Subjects allocated to terminal nodes 1, 2, and 4 had a higher probability (57.1 to 97.4%) of being an endotype A, whereas subjects allocated to terminal nodes 3, 5, and 6 had a lower probability (0.0 to 22.2%) of being an endotype A. Accordingly, for calculating the diagnostic test characteristics of decision tree #1, subjects in terminal nodes 1, 2, and 4 were classified as endotype A, and subjects in terminal nodes 3, 5, and 6 were classified as endotype B. Table 3 shows the diagnostic test characteristics of decision tree #1 for identifying endotype A subjects, using the original endotype classification strategy as the reference standard.

TABLE 3

Diagnostic test characteristics of decision tree #1 for identifying endotype A.

| Variable | Value | 95% C.I. |
|---|---|---|
| True positives (n) | 113 | — |
| False positives (n) | 19 | — |
| True negatives (n) | 161 | — |
| False negatives (n) | 7 | — |
| Sensitivity | 94% | 88 to 97 |
| Specificity | 89% | 84 to 93 |
| Positive predictive value | 86% | 78 to 91 |
| Negative predictive value | 96% | 91 to 98 |
| Positive likelihood ratio | 8.9 | 5.8 to 13.7 |
| Negative likelihood ratio | 0.07 | 0.03 to 0.13 |

After deriving decision tree #1 using data from the previously enrolled 300 subjects, as described above, decision tree #1 was tested in 43 newly enrolled subjects. Using the original endotyping strategy, there were 14 endotype A subjects and 29 endotype B subjects in the test cohort. When these subjects were classified according to the derived four-gene decision tree #1, the AUROC was 0.97 (95% CI, 0.93-1.00). The sensitivity and specificity for identifying endotype A were 100% (95% CI, 73-100%) and 79% (95% CI, 60-91%), respectively.

Example 3

Clinical Characteristics of the Endotypes After Reclassification

Although decision tree #1 correctly classified 91% of the subjects of the original 300 subjects, 19 subjects allocated to endotype A were originally endotype B, and seven subjects allocated to endotype B were originally endotype A. In previous studies using the 100-gene mosaics, endotype A subjects had worse outcomes compared to endotype B subjects, and prescription of corticosteroids was associated with increased risk of mortality among endotype A subjects [5]. Accordingly, it was determined if the classification based on decision tree #1 changed the previously observed differences between endotypes A and B, by combining the derivation and test cohorts (n=343), and the clinical characteristics of the endotype A and B subjects, as defined by decision tree #1, were compared. Consistent with the previous reports, endotype A subjects were younger, had a higher mortality rate, and had a higher rate of complicated course, compared to endotype B subjects, as shown in Table 4.

TABLE 4

Clinical and demographic data for endotypes A and B, as classified by decision tree #1.

| Variable | Endotype A | Endotype B | P value |
|---|---|---|---|
| N | 152 | 191 | — |
| # of males (%) | 77 (58%) | 96 (57%) | 0.929 |
| Median age, years (IQR) | 1.6 (0.6-4.7) | 3.2 (1.4-6.6) | <0.001 |
| Median PRISM score (IQR) | 13 (8-20) | 11 (8-17) | 0.163 |
| Mortality, n (%) | 27 (18) | 15 (8) | 0.009 |
| Complicated course,* n (%) | 60 (39) | 41 (21) | <0.001 |

Definition of abbreviations:
IQR = interquartile range;
PRISM = Pediatric Risk of Mortality.
*Defined as persistence of two or more organ failures on Day 7 of septic shock or 28-day mortality.

Table 5 shows the results of logistic regression models evaluating the association between endotype allocation and outcome. After accounting for illness severity (Pediatric Risk of Mortality score) and age, allocation to endotype A was independently associated with increased odds of mortality and complicated course, which represents a composite variable capturing both mortality and organ failure burden.

TABLE 5

Logistic regression to test for an association between allocation to endotype A and outcome.

| Outcome | Variable | O.R. (95% C.I.) | P value |
|---|---|---|---|
| Mortality | Allocation to endotype A | 2.3 (1.1-4.9) | 0.022 |
| | PRISM score | 1.1 (1.1-1.1) | <0.001 |
| | Age | 1.0 (0.9-1.2) | 0.562 |
| Complicated course | Allocation to endotype A | 2.1 (1.3-3.6) | 0.004 |
| | PRISM score | 1.1 (1.1-1.1) | <0.001 |
| | Age | 1.0 (0.9-1.1) | 0.514 |

Table 6 shows that prescription of corticosteroids was independently associated with increased odds of mortality among endotype A subjects, but not among endotype B subjects.

TABLE 6

Logistic regression to test for an association between corticosteroid prescription and mortality, within endotype.

| Endotype | Variable | O.R. (95% CI) | P value |
|---|---|---|---|
| A | Corticosteroids | 3.7 (1.4-9.8) | 0.008 |
| | PRISM score | 1.1 (1.0-1.2) | <0.001 |
| | Age | 1.1 (0.9-1.2) | 0.449 |
| B | Corticosteroids | 1.3 (0.4-4.9) | 0.656 |
| | PRISM score | 1.1 (1.1-1.2) | <0.001 |
| | Age | 1.0 (0.9-1.2) | 0.743 |

Example 4

Secondary Considerations

To determine the biological links among the four endotype-defining genes of decision tree #1, these genes were uploaded to the IPA platform. The top scoring canonical pathway represented by these four genes was granulocyte macrophage colony-stimulating factor signaling (p=7.1E-11). The glucocorticoid receptor signaling pathway was also represented among these four genes (p=0.001).

Figure 2:
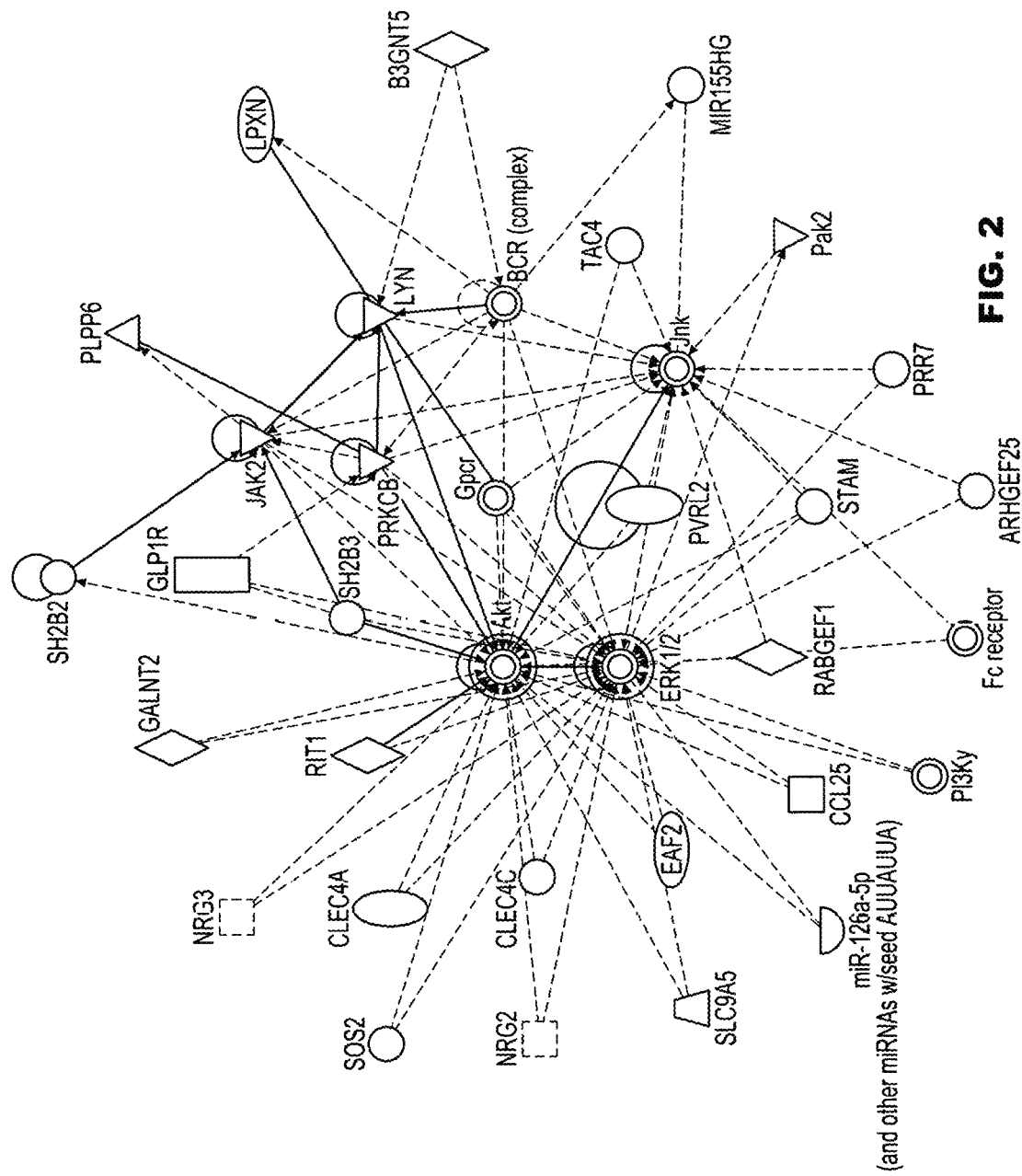
FIG. 2 depicts the gene network involving the four classifier genes of model #1 generated by uploading the four classifier genes to the IPA platform. Gray shading highlights the network nodes corresponding to the four classifier genes, JAK1, PRKCB, SOS2, and LYN.
Figure 3A:
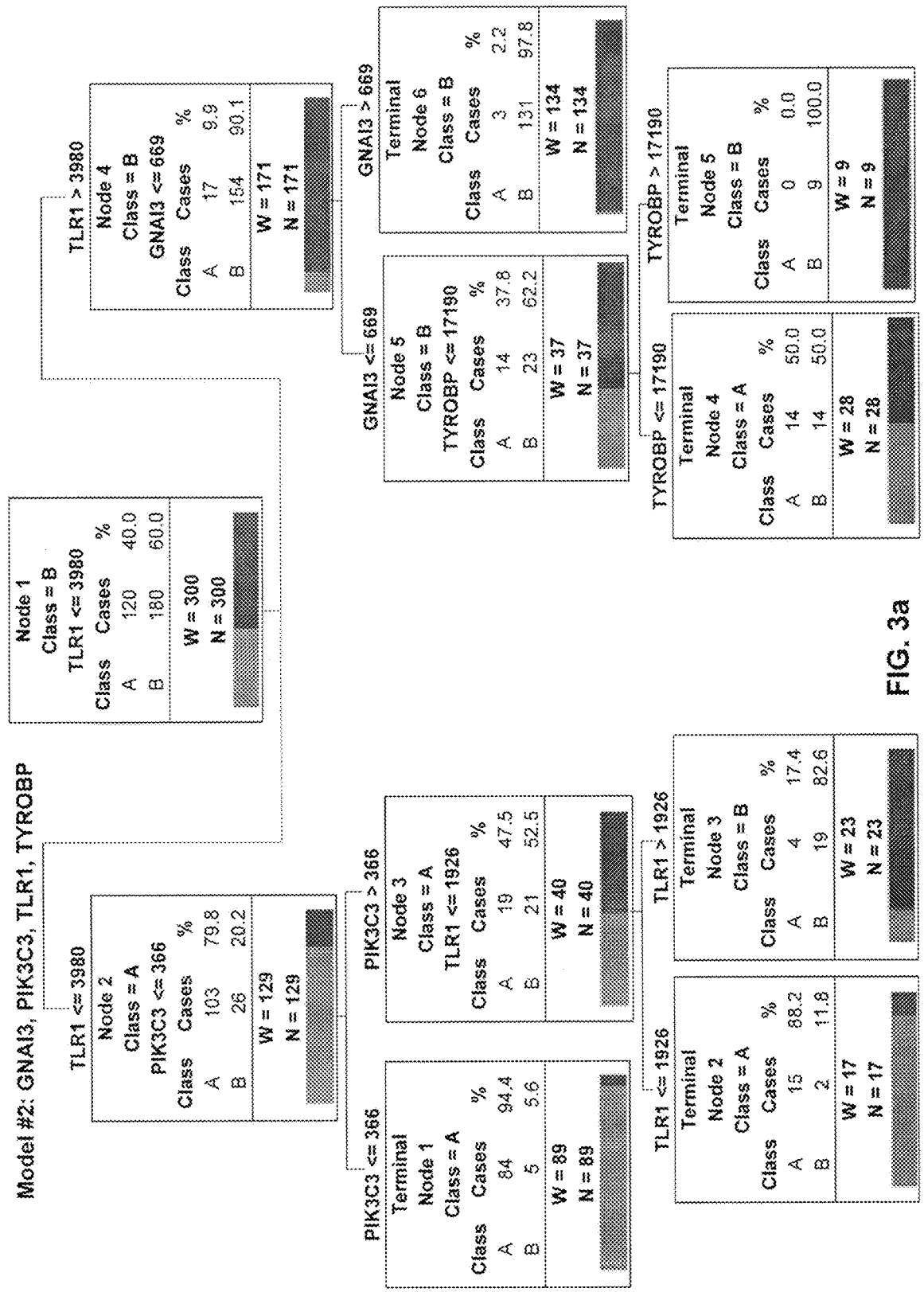
FIG. 3 depicts decision trees #2-8, derived from models #2-8. Decision tree #2 (FIG. 3a), derived from model #2, includes the genes GNAI3, PIK3C3, TLR1, and TYROBP; decision tree #3 (FIG. 3b), derived from model #3, includes the genes CD247, ITGAX, RHOT1, and TLR1; decision tree #4 (FIG. 3c), derived from model #4. includes the genes ARPC5, CSNK1A1, FCGR2C, and PPP2R5C; decision tree #5 (FIG. 3d), derived from model #5, includes the genes ASAH1, FCGR2C, TRA, and TYROBP; decision tree #6 (FIG. 3e), derived from model #6, includes the genes BTK, FAS, MAP3K3, and PPP2R2A; decision tree #7 (FIG. 3D, derived from model #7, includes the genes CASP4, CD247, EP300, and MAP3K3; and decision tree #8 (FIG. 3g), derived from model #8, includes the genes CREB5, CSNK1A1, and TLR2.
Figure 3B:
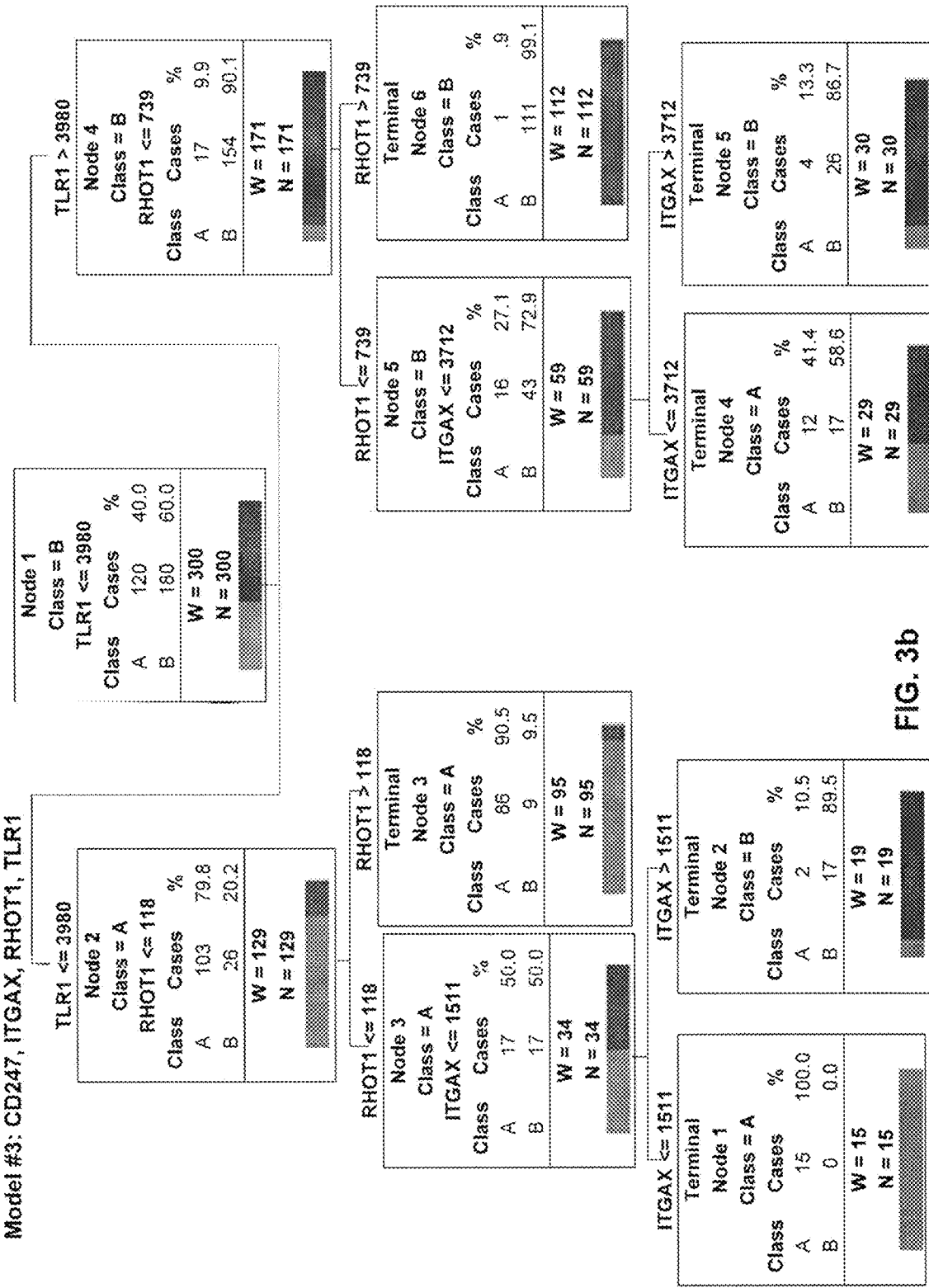
Figure 3C:
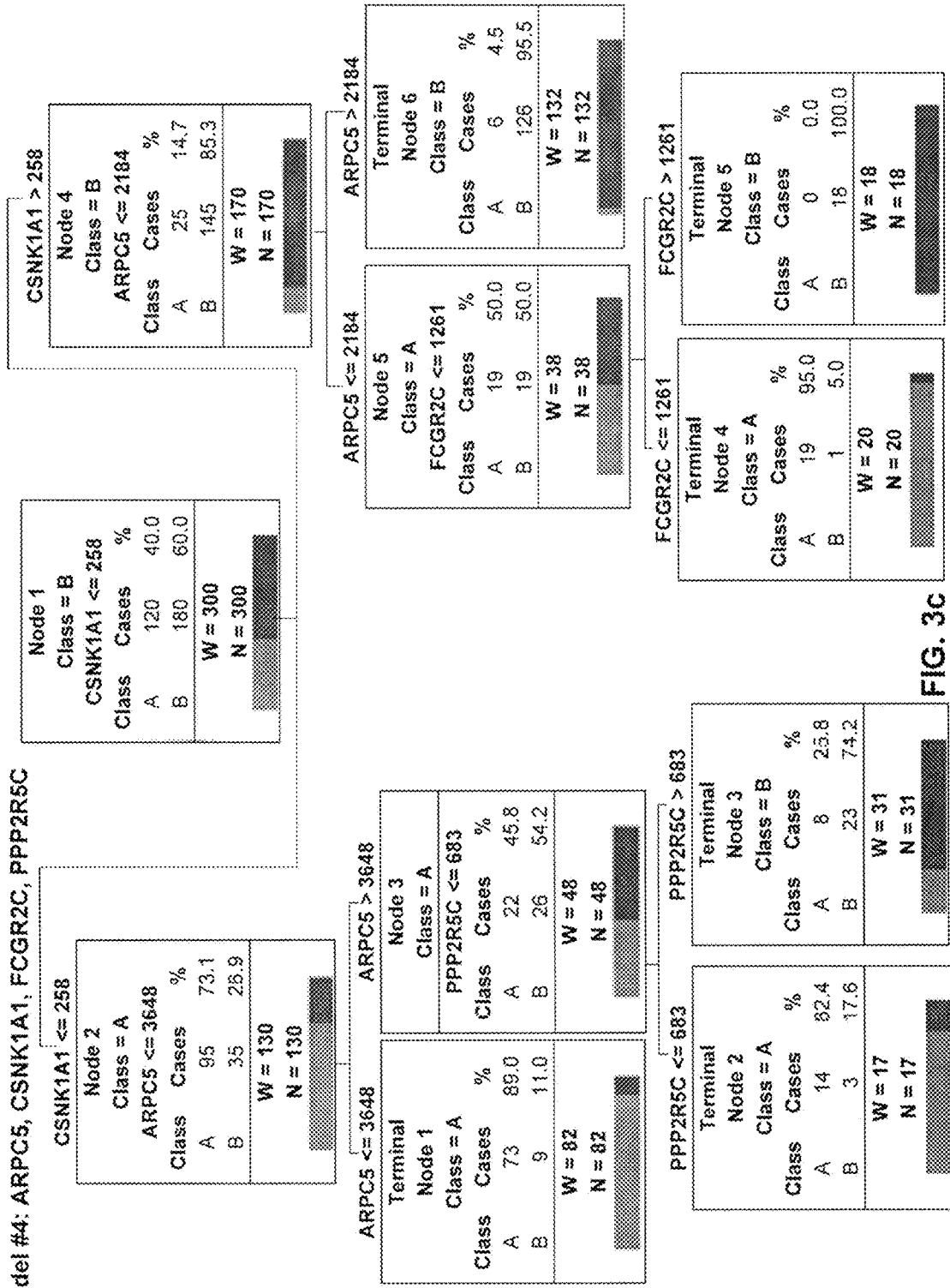
Figure 3D:
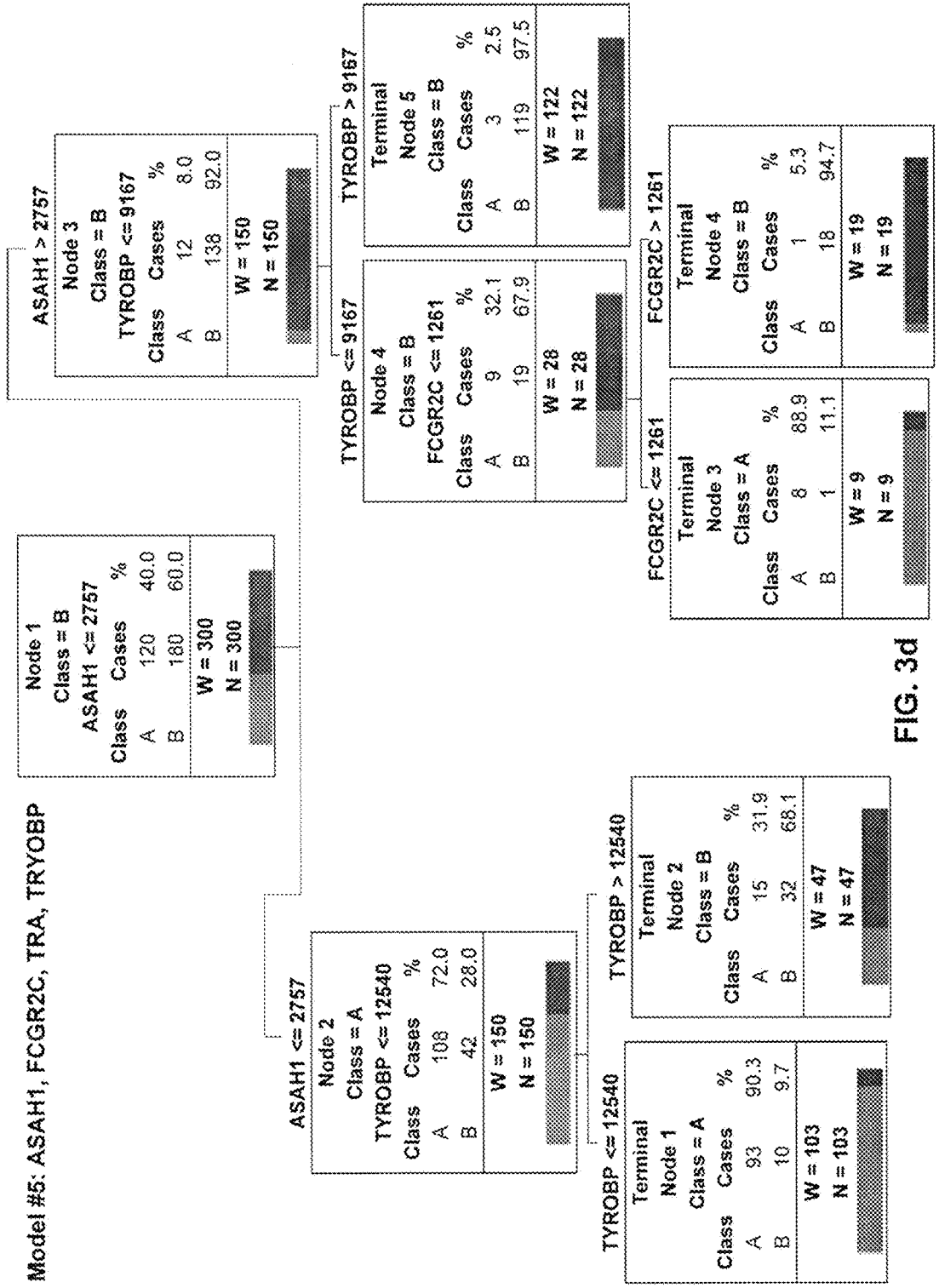
Figure 3E:
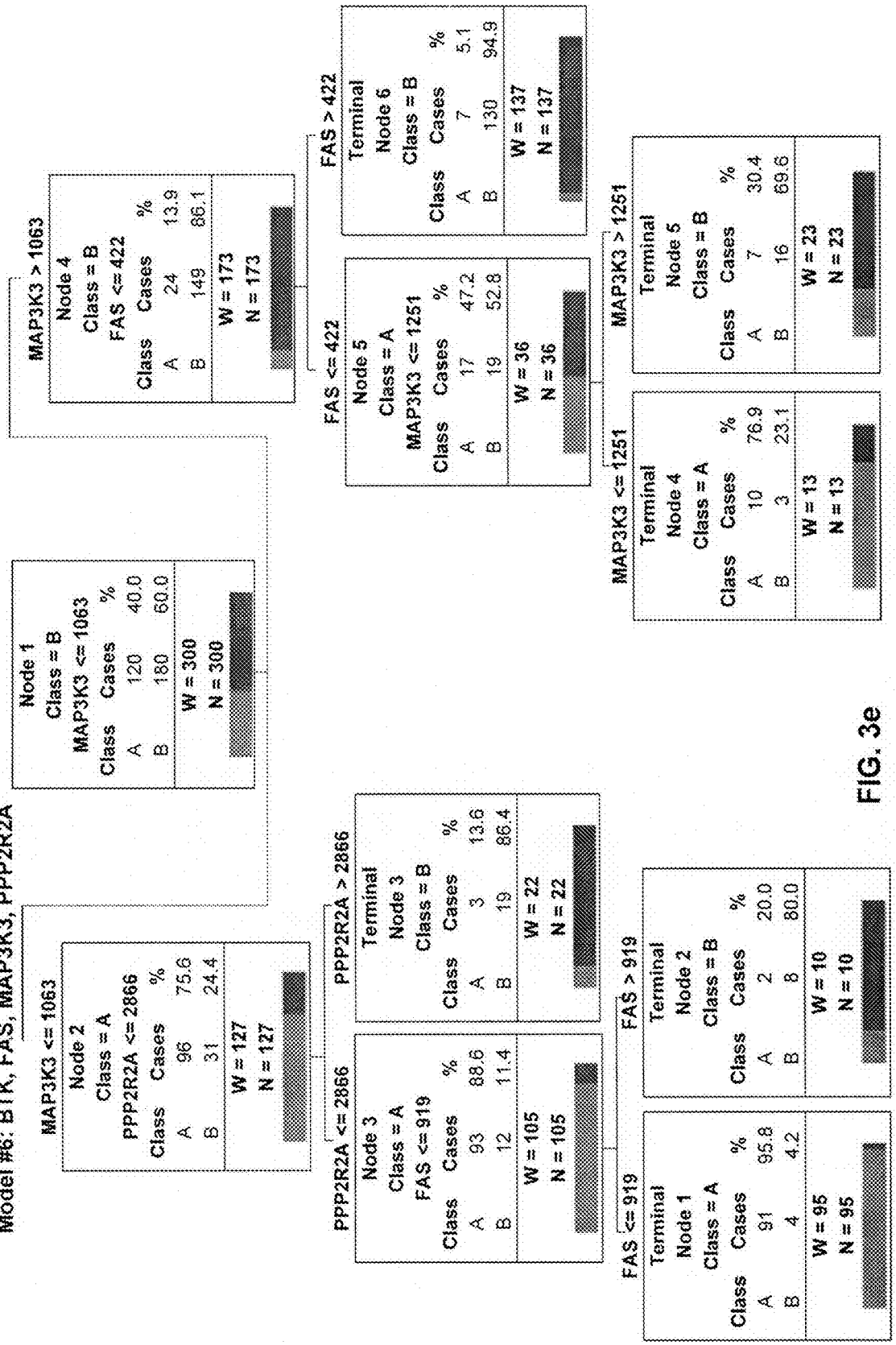
Figure 3F:
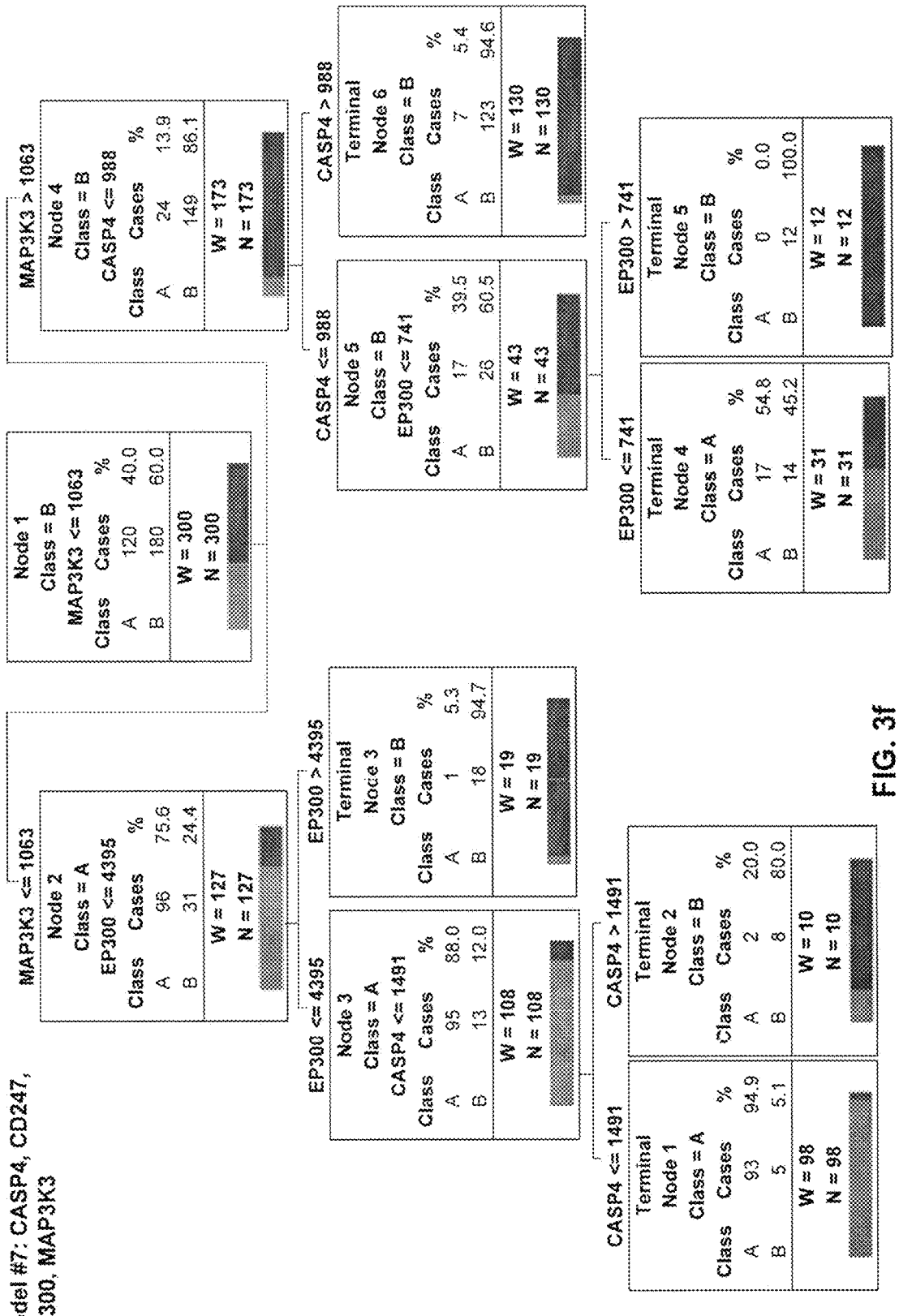
Figure 3G:
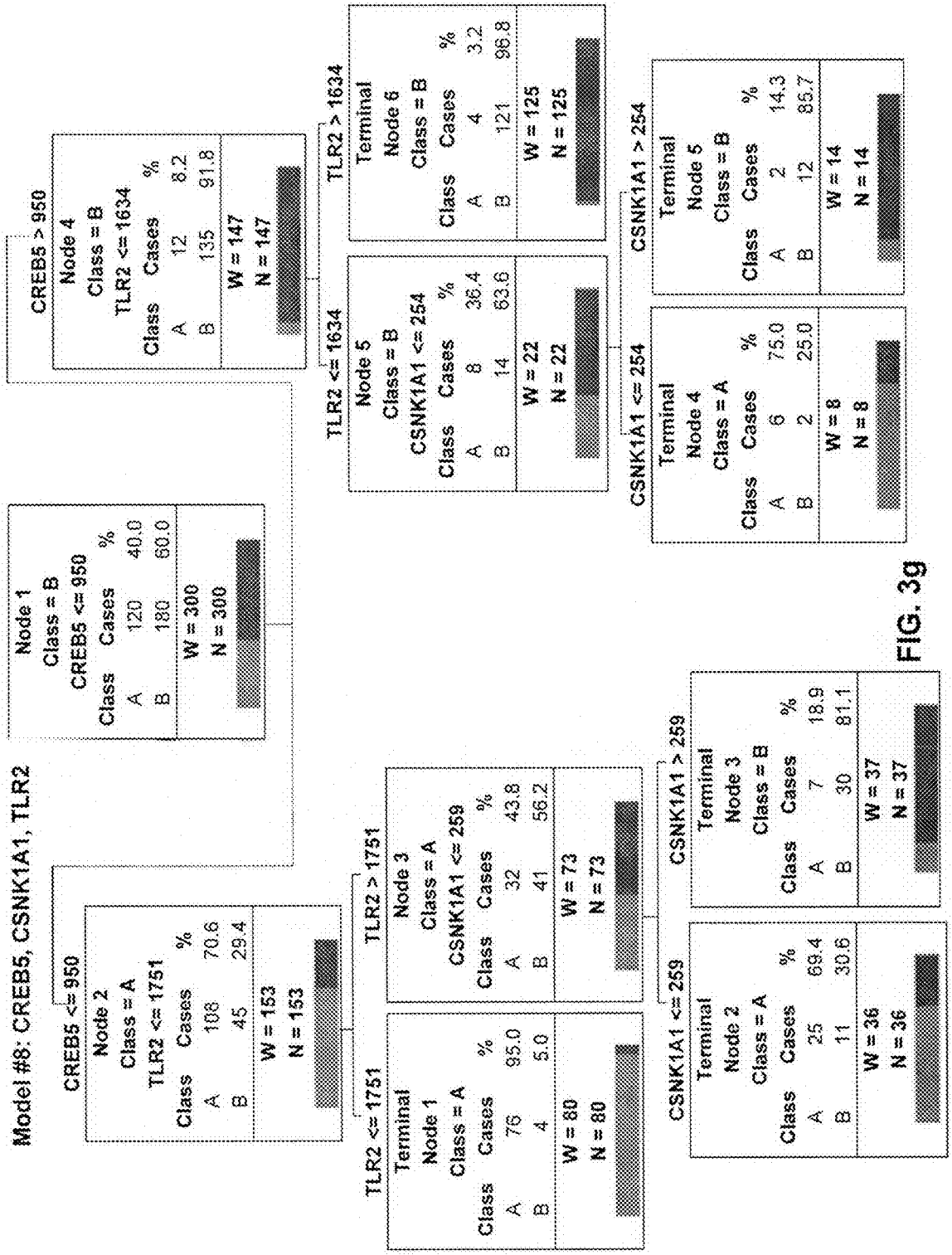

FIG. 2 provides the top gene network corresponding to the four endotype-defining genes of decision tree #1. Gray shading highlights the network nodes corresponding to the four classifier genes, JAK1, PRKCB, SOS2, and LYN. Table 7 provides the annotations for the nodes in the gene network, which contains the protein kinases AKT, ERK1/2, and JNK as highly connected nodes. The network corresponds to cell-to cell signaling and interaction, cellular development, and cellular growth and proliferation, and is subject to regulation by miRNA 126a-5p.

TABLE 7

Annotations for the remaining network nodes.

| Node ID | Description | Entrez Gene ID for Human |
|---|---|---|
| Akt | AKT1/2/3, B/Akt, Pkb, RAC-PK | |
| ARHGEF25 | Rho guanine nucleotide exchange factor 25 | 115557 |
| B3GNT5 | UDP-GlcNAc:betaGal beta-1,3-N-acetylglucosaminyltransferase 5 | 84002 |
| BCR (complex) | B Cell Receptor, Bcr (B-cell receptor complex) | |
| CCL25 | chemokine (C-C motif) ligand 25 | 6370 |
| CLEC4A | C-type lectin domain family 4 member A | 50856 |
| CLEC4C | C-type lectin domain family 4 member C | 170482 |
| EAF2 | ELL associated factor 2 | 55840 |
| ERK1/2 | p44/p42 MAPK | |
| Fc receptor | FCR | |
| GALNT2 | polypeptide N-acetylgalactosaminyltransferase 2 | 2590 |
| GLP1R | glucagon like peptide 1 receptor | 2740 |
| Gper | G-protein-coupled receptor | |
| JAK2 | Janus kinase 2 | 3717 |
| Jnk | JUN Kinase | |
| LPXN | leupaxin | 9404 |
| LYN | LYN proto-oncogene, Src family tyrosine kinase | 4067 |
| miR-126a-5p (and other miRNAs w/seed AUUAUUA) | miR-126-5p | |
| MIR155HG | MIR155 host gene | 114614 |
| NRG2 | neuregulin 2 | 9542 |
| NRG3 | neuregulin 3 | 10718 |
| Pak2 | p21 protein (Cdc42/Rac)-activated kinase 2 | |
| PI3Ky | P13K gamma | |
| PLPP6 | phospholipid phosphatase 6 | 403313 |
| PRKCB | protein kinase C, beta | 5579 |
| PRR7 | proline rich 7 (synaptic) | 80758 |
| PVRL2 | poliovirus receptor-related 2 (herpesvirus entry mediator B) | 5819 |
| RABGEF1 | RAB guanine nucleotide exchange factor (GEF) 1 | 27342 |
| RIT1 | Ras-like without CAAX 1 | 6016 |
| SH2B2 | SH2B adaptor protein 2 | 10603 |
| SH2B3 | SH2B adaptor protein 3 | 10019 |
| SLC9A5 | solute carrier family 9, subfamily A (NHES, cation proton antiporter | 6553 |
| SOS2 | SOS Ras/Rho guanine nucleotide exchange factor 2 | 6655 |
| STAM | signal transducing adaptor molecule | 8027 |
| TAC4 | tachykinin 4 (hemokinin) | 255061 |

Although terminal node 4 of decision tree #1 assigned subjects to endotype A, 43% of these subjects were originally classified as endotype B. Accordingly, some subjects allocated to terminal node 4 of decision tree #1 appear not to be easily defined as endotype A or B. These 21 subjects were grouped as "endotype C", and their clinical phenotype was compared with the remaining endotype A and B subjects. Table 8 shows the results. Endotype A subjects continued to have a higher mortality rate and a higher rate of complicated course, compared to endotype B subjects. Endotype C subjects tended to have an intermediate mortality rate and an intermediate rate of complicated course, relative to both endotypes A and B. Endotype C can therefore be considered an intermediate between the extremes of endotype A and B, or can be considered as a third endotype.

TABLE 8

Clinical and demographic data for the endotypes A, B, and C.

| | Endotype A | Endotype B | Endotype C | P value |
|---|---|---|---|---|
| N | 111 | 168 | 21 | — |
| # of males (%) | 69 (62) | 96 (57) | 8 (38) | 0.120 |
| Median age, years (IQR) | 1.4 (0.3-4.2) | 3.0 (1.3-6.6) | 3.0 (0.9-4.7) | <0.001 |
| Median PRISM score (IQR) | 14 (9-21) | 12 (8-18) | 15 (9-22) | 0.328 |
| Mortality, n (%) | 22 (20) | 13 (8) | 3 (14) | 0.012 |
| Complicated course, n (%) | 47 (42) | 34 (20) | 7 (33) | <0.001 |

Example 5

Secondary Analysis of Four-Gene Decision Tree #1 for Identifying Septic Shock Endotypes Septic shock endotypes A and B have been determined based on a 100-gene expression signature, as described above. The 100 endotyping genes reflect adaptive immune function and glucocorticoid receptor signaling, both of which are highly relevant to the pathobiology of septic shock. Importantly, the endotypes differ with respect to outcome, organ failure burden, and treatment responsiveness to corticosteroids. They can also differ with respect to other immune modulating therapies. The clinical utility of endotyping is to enable precision medicine among critically ill patients with septic shock.

CART methodology was applied to reduce the endotype defining gene signature to a decision tree consisting of just four genes, namely decision tree #1, thereby providing for a robust and rapid test for clinical application. A secondary analysis has now been conducted to assess the "uniqueness" of the four-gene decision tree #1 and to consider alternative four-gene combinations.

From the 100 endotyping gene list, four-gene biomarker panels were randomly selected, and a decision tree was derived to differentiate between endotypes A (n=120) and B (n=180). The same CART methodology and pruning parameters were applied as used to derive the original four-gene decision tree #1. One hundred iterations of this procedure were performed to generate alternative endotyping models.

Table 9 lists the selected four-gene biomarker panels of the one hundred iterations. These four-gene biomarker panels can be used in classifying a pediatric patient with septic shock as high risk, low risk, or moderate risk, wherein the risk classification can be used to determine, and subsequently administer, an appropriate treatment to the patient.

TABLE 9

Table of alternative endotyping models based on alternative four-gene biomarker panels, listed in order of decreasing AUROC for the listed model; the original four-gene decision tree #1, based on model #1, is indicated in italics.

| MODEL # | GENES | | | |
|---|---|---|---|---|
| 1 | *JAK2* | *LYN* | *PRKCB* | *SOS2* |
| 2 | GNAI3 | PIK3C3 | TLR1 | TYROBP |
| 3 | CD247 | ITGAX | RHOT1 | TLR1 |
| 4 | ARPC5 | CSNK1A1 | FCGR2C | PPP2R5C |
| 5 | ASAH1 | FCGR2C | TRA | TYROBP |
| 6 | BTK | FAS | MAP3K3 | PPP2R2A |
| 7 | CASP4 | CD247 | EP300 | MAP3K3 |
| 8 | CREB5 | CSNK1A1 | PRKCB | TLR2 |
| 9 | BCL6 | CASP8 | ITGAM | NCOA2 |
| 10 | CSNK1A1 | ITGAV | MAP3K5 | TBK1 |
| 11 | LAT2 | LYN | PPP2R2A | PRKCB |
| 12 | MAPK1 | PRKAR1A | TLE4 | TLR2 |
| 13 | ARPC5 | CAMK2G | CASP4 | ICAM3 |
| 14 | BCL6 | CAMK2D | PIK3C3 | SOS1 |
| 15 | BCL6 | LAT2 | PIK3CA | RAF1 |
| 16 | CAMK2D | IL1A | PRKCB | TLR8 |
| 17 | CREB5 | MAP3K7 | MKNK1 | PIK3R1 |
| 18 | JAK2 | PRKCB | PSMB7 | PTPRC |
| 19 | MKNK1 | RAF1 | TBK1 | UBE3A |
| 20 | ASAH1 | BCL6 | PIK3C2A | PIK3R1 |
| 21 | ASAH1 | KAT2B | MDH1 | PPP1R12A |
| 22 | CASP2 | CD79A | FAS | MAP4K4 |
| 23 | CASP4 | GK | MAP3K3 | SOS2 |
| 24 | CASP8 | CD3E | EP300 | PPP2R2A |
| 25 | CD3G | EP300 | LAT2 | TGFBR1 |
| 26 | CREB5 | DBT | MAP2K4 | RHOT1 |
| 27 | CTNNB1 | DAPP1 | LYN | PDPR |
| 28 | HDAC4 | MAP4K1 | PIK3CA | PLCG1 |
| 29 | ICAM3 | LYN | TAF11 | TLR8 |
| 30 | MAP2K4 | PRKCB | TLR1 | TNFSF10 |
| 31 | ARPC5 | CTNNB1 | MAP2K4 | PIK3CA |
| 32 | ATP2B2 | HDAC4 | PLCG1 | TBK1 |
| 33 | BCL6 | CASP8 | FCGR2C | TLR1 |
| 34 | BTK | CREB5 | RHOT1 | ZAP70 |
| 35 | CAMK2D | CREB5 | FCGR2A | PDPR |
| 36 | CAMK2G | INPP5D | MAP2K4 | TBK1 |
| 37 | CD3G | CTNNB1 | MAP3K7 | TLR1 |
| 38 | FCGR2A | MAPK1 | PIK3C2A | SMAD4 |
| 39 | FCGR2C | IL1A | PIK3CD | TLR1 |
| 40 | MAP4K4 | NCOA2 | ROCK1 | TLR1 |

TABLE 9-continued

Table of alternative endotyping models based on alternative four-gene biomarker panels, listed in order of decreasing AUROC for the listed model; the original four-gene decision tree #1, based on model #1, is indicated in italics.

| MODEL # | GENES | | | |
|---|---|---|---|---|
| 41 | BMPR2 | CAMK2G | CASP1 | MAP4K4 |
| 42 | BMPR2 | INPP5D | PDPR | SP1 |
| 43 | CAMK2D | CREB5 | NFATC1 | ZDHHC17 |
| 44 | CAMK2G | MKNK1 | NCOA2 | ZAP70 |
| 45 | ITGAV | MAPK1 | PPP2R2A | PTEN |
| 46 | CAMK4 | DBT | KAT2B | MAP4K4 |
| 47 | CASP1 | MAP2K4 | PPP2R2A | PRKAR1A |
| 48 | CASP4 | JAK1 | MAP3K5 | TLR1 |
| 49 | CD3E | MAP4K4 | MAPK1 | ZAP70 |
| 50 | BTK | CAMK2D | CAMK2G | ROCK1 |
| 51 | CAMK2G | PIK3CA | PTPRC | TRA |
| 52 | MAP4K4 | PLCG1 | PTPRC | ZDHHC17 |
| 53 | NCOA2 | POU2F2 | PPP2R5C | SP1 |
| 54 | ATP2B2 | JAK1 | JAK2 | ROCK1 |
| 55 | CAMK2G | CAMK4 | CD79A | PIK3R1 |
| 56 | CAMK4 | CASP8 | ITGAX | MAP2K4 |
| 57 | CASP4 | DAPP1 | MAP3K5 | ROCK1 |
| 58 | CASP8 | MAP3K3 | MAP4K4 | PAK2 |
| 59 | DAPP1 | GNAI3 | MAPK14 | SEMA4F |
| 60 | DAPP1 | HDAC4 | MAP3K3 | TNFSF10 |
| 61 | ITGAX | MAP3K7 | MAP4K4 | MAPK1 |
| 62 | JAK2 | PTPRC | SOS2 | ZAP70 |
| 63 | CAMK2G | IL1A | MAP3K3 | TAF11 |
| 64 | CD247 | EP300 | PIAS1 | TBK1 |
| 65 | DBT | PSMB7 | TNFSF10 | TRA |
| 66 | MKNK1 | POU2F2 | UBE3A | ZAP70 |
| 67 | ARPC5 | NCOA2 | SOS1 | UBE3A |
| 68 | CAMK2G | KAT2B | MAP3K7 | NFATC1 |
| 69 | CD247 | CD79A | FAS | PSMB7 |
| 70 | FAS | JAK1 | MAP4K4 | TLE4 |
| 71 | FCGR2C | ITGAX | PIK3R1 | SEMA4F |
| 72 | HDAC4 | MDH1 | PIK3R1 | PLCG1 |
| 73 | HLA-DMA | INPP5D | MAP2K4 | USP48 |
| 74 | MAP4K4 | PIK3R1 | PPP1R12A | TBK1 |
| 75 | PPP1R12A | PRKCB | TAF11 | TRA |
| 76 | CD247 | MAP3K7 | SEMA4F | TNFSF10 |
| 77 | PLCG1 | PTPRC | SEMA6B | SMAD4 |
| 78 | BMPR2 | CAMK2G | IL1A | MDH1 |
| 79 | BTK | CTNNB1 | GNAI3 | MAP4K4 |
| 80 | CD3E | FAS | MAP3K7 | PRKCB |
| 81 | DAPP1 | PIK3CA | TAF11 | TNFSF10 |
| 82 | HDAC4 | MAP4K1 | MAPK14 | SEMA4F |
| 83 | MAP3K1 | MDH1 | PIAS1 | USP48 |
| 84 | APAF1 | CD247 | PPP2R2A | TAF11 |
| 85 | APAF1 | EP300 | IL1A | TAF11 |
| 86 | DAPP1 | FYN | MAP3K3 | SEMA4F |
| 87 | GK | LAT2 | SOS1 | UBE3A |
| 88 | JAK1 | NFATC1 | PDPR | PTEN |
| 89 | ARPC5 | CASP2 | JAK1 | TLR2 |
| 90 | CAMK4 | IL1A | MAP4K1 | POU2F2 |
| 91 | CD3G | INPP5D | PPP1R12A | PPP2R5C |
| 92 | CD79A | CREB1 | FCGR2C | PPP1R12A |
| 93 | INPP5D | ITGAM | JAK1 | NCR3 |
| 94 | ITGAV | NFATC1 | PPP1R12A | USP48 |
| 95 | BTK | CD3G | NCOA2 | ZAP70 |
| 96 | CTNNB1 | MAP4K1 | PAK2 | PIK3C3 |
| 97 | ATP2B2 | CASP4 | FAS | TBK1 |
| 98 | PSMB7 | ROCK1 | SEMA4F | USP48 |
| 99 | ITGAV | MAP3K7 | PIK3C3 | ZDHHC17 |
| 100 | KAT2B | PDPR | SEMA6B | ZDHHC17 |
| 101 | CAMK2D | PIK3R1 | PPP2R5C | PRKCB |

Example 6

Phenotypes Based on Alternative Endotyping Models

An analysis was conducted to determine if alternative 4 gene models listed in Table 9 can also reproduce these three phenotypic features of endotypes A, B, and C after reclassification. Table 10 below provides the odds ratios for mortality and complicated course among patients allocated to endotype A. It can be assumed that the odds ratios for mortality and complicated course among patients allocated to endotype B are the inverse of that provided in Table 10. Each odds ratio reflects a multivariable logistic regression procedure that takes into account the confounding variables of age, baseline illness severity, and co-morbidity burden. Model #1, indicated in italics, reflects the primary model described in the preceding examples. The remaining models reflect the alternative four-gene models #2-8 from Table 9 previously generated via random selection of four gene sets.

TABLE 10

Odds ratios for mortality and complicated course among patients allocated to endotype A.

| MODEL # | Outcome | O.R. | 95% C.I. | P value |
|---|---|---|---|---|
| #1 | Mortality | 2.3 | 1.0 to 4.9 | 0.022 |
|  | Complicated Course | 2.1 | 1.3 to 3.6 | 0.004 |
| #2 | Mortality | 1.9 | 0.9 to 3.9 | 0.101 |
|  | Complicated Course | 2 | 1.2 to 3.3 | 0.013 |
| #3 | Mortality | 1.9 | 0.9 to 4.0 | 0.09 |
|  | Complicated Course | 2.4 | 1.4 to 4.0 | 0.001 |
| #4 | Mortality | 1.8 | 0.8 to 3.6 | 0.134 |
|  | Complicated Course | 1.4 | 0.8 to 2.4 | 0.18 |
| #5 | Mortality | 1.9 | 0.9 to 3.9 | 0.105 |
|  | Complicated Course | 2.1 | 1.1 to 3.9 | 0.021 |
| #6 | Mortality | 2.1 | 0.98 to 4.4 | 0.056 |
|  | Complicated Course | 2.6 | 1.5 to 4.4 | <0.001 |
| #7 | Mortality | 1.21 | 0.6 to 2.6 | 0.562 |
|  | Complicated Course | 2 | 1.2 to 3.5 | 0.007 |
| #8 | Mortality | 1.7 | 0.8 to 3.5 | 0.179 |
|  | Complicated Course | 1.8 | 1.1 to 3.0 | 0.032 |

Table 11 below provides the odds ratio for mortality in patients who receive corticosteroids, within each endotype. Each odds ratio reflects a multivariable logistic regression procedure that takes into account the confounding variables of age, baseline illness severity, and co-morbidity burden. Model #1, indicated in italics, reflects the primary model described in the preceding examples. The remaining models reflect alternative 4-gene models #2-8 from Table 9 previously generated via random selection of four-gene sets.

TABLE 11

Odds ratio for mortality in patents who receive corticosteroids.

| MODEL # | Endotype | O.R. | 95% C.I. | P value |
|---|---|---|---|---|
| #1 | A | 3.7 | 1.4 to 9.8 | 0.008 |
|  | B | 1.8 | 0.5 to 6.1 | 0.366 |
| #2 | A | 5.4 | 1.8 to 16.0 | 0.002 |
|  | B | 1.1 | 0.4 to 3.1 | 0.918 |
| #3 | A | 4.1 | 1.6 to 10.6 | 0.004 |
|  | B | 1.5 | 0.44 to 5.0 | 0.515 |
| #4 | A | 5.3 | 1.8 to 15.8 | 0.003 |
|  | B | 1.4 | 0.5 to 4.0 | 0.567 |
| #5 | A | 3.4 | 1.3 to 9.3 | 0.015 |
|  | B | 1.9 | 0.6 to 6.2 | 0.259 |
| #6 | A | 2.1 | 1.4 to 12.3 | 0.008 |
|  | B | 2.3 | 0.7 to 6.9 | 0.156 |
| #7 | A | 2.1 | 0.8 to 5.4 | 0.135 |
|  | B | 4.1 | 1.0 to 15.9 | 0.044 |
| #8 | A | 3.3 | 1.2 to 9.0 | 0.023 |
|  | B | 1.9 | 0.6 to 5.9 | 0.241 |

None of alternative models #2-8 was demonstrated to replicate the mortality phenotype. In other words, after reclassification, an independent association between allocation to endotype A and increased odds of mortality was not observed. This is a fundamental aspect of the previously described results. All of the alternative models listed in Tables 10-11, with the exception of model #4, were shown to replicate the complicated course phenotype. All of the alternative models listed in Tables 10-11, with the exception of model #7, were shown to replicate the corticosteroid phenotype. Thus, while close, none of the alternative four-gene models #2-8 has demonstrated the ability to fully replicate the phenotypes previously reported and confirmed by model #1.

Based on this, further testing of the alternative four-gene models listed in Table 9 was not performed. Such models would be expected to be even less able to fully replicate the previously reported phenotypes.

Model #1 therefore most closely approximates the endotyping procedure based on 100 genes, which is the reference criterion. Model #1 has the best statistical performance during derivation and validation, and also completely replicates the phenotypic features of the endotypes, when compared to the reference criterion.

Figure 4:
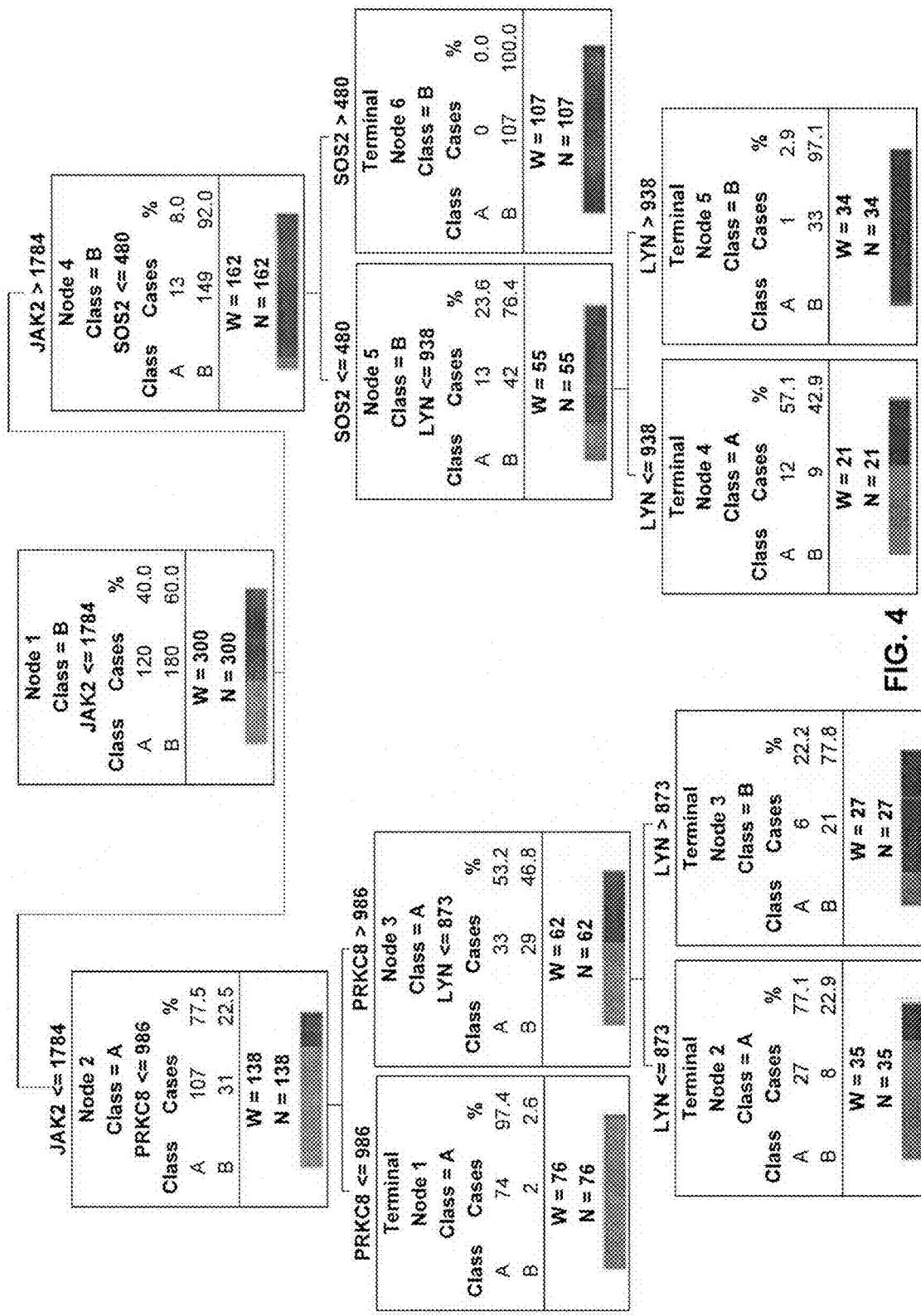
FIG. 4 depicts an alternative version of decision tree #1, which was derived from using the 25 unique genes that appear in models #1 through #8 as candidate predictor variables to determine which of the genes "best" differentiate between endotypes A and B.

In a subsequent analysis, the 25 unique genes that appear in models #1 through #8 were used as candidate predictor variables. This is the most objective approach to assessing which of the genes are the "best" for differentiating between endotype A and B. Notably, this procedure replicated model #1, as shown in FIG. 4, which depicts an alternative version of decision tree #1.

Example 7

Methods of Classifying and Treating Patients Based on 4-Gene Signature

The biomarkers described herein are used to classify a patient with septic shock as having high risk or low risk of adverse outcome. First, a sample from a pediatric patient with septic shock is analyzed to determine the expression levels of two or more biomarkers selected from the biomarkers listed in Table 1. For example, all of the biomarkers in model #1, namely JAK2, LYN, PRKCB, and SOS2, are analyzed, and decision tree #1, as described herein, is applied to the resulting biomarker levels. It is then determined whether the expression level(s) of the two or more biomarkers are elevated above a cut-off level, wherein the patient is classified as endotype A/high risk where there is a presence of a non-elevated level of the two or more biomarkers, and wherein the patient is classified as endotype B/low risk or endotype C/intermediate risk where there is an absence of an non-elevated level of the two or more biomarkers.

The patient is then administered a treatment based on the patient's classification as endotype A/high risk, endotype B/low risk, or endotype C/intermediate risk. A patient that is classified as endotype B/low risk or endotype C/intermediate risk is administered a treatment which includes one or more corticosteroid, whereas a patient that is classified as endotype A/high risk is administered a treatment which excludes one or more corticosteroid. A patient that is classified as endotype A/high risk is then optionally administered a high risk treatment or therapy. In this way, individualized treatment is provided, and clinical outcomes for septic shock patients are improved and morbidity reduced.

A second sample is then obtained, and the patient's classification is confirmed or updated. The treatment being administered is then maintained or revised as necessary. This allows for determination and monitoring of therapeutic efficacy.

Example 8

Methods—Determining Mortality Risk

The methods used in Examples 8-11 are summarized below:

Study Subjects and Data Collection.

Study subjects were from an observational cohort study ongoing at multiple pediatric intensive care units (PICUs) across the United States. The data collection protocol was approved by the local Institutional Review Boards of each participating institution and has been previously described in detail (8, 33). Briefly, children ≤10 years of age admitted to the PICU and meeting pediatric-specific consensus criteria for septic shock (34) were enrolled after informed consent, which was obtained from parents or legal guardians. Blood samples were obtained within 24 hours of a septic shock diagnosis for isolation of serum and RNA. Total RNA was isolated from whole blood using the PaxGene™ Blood RNA System (PreAnalytiX, Qiagen/Becton Dickson, Valencia, Calif.). Clinical and laboratory data were collected daily while in the PICU. Mortality was tracked for 28 days after enrollment. Organ failure was tracked over the first seven days after enrollment and defined using pediatric specific consensus criteria (34). Baseline illness severity was measured using Pediatric Risk of Mortality-III (PRISM-III) scores reflecting data from the first 24 hours of admission (9).

Potential subjects for the current study consisted of the group in which PERSEVERE was developed and validated (28-30), and another group of newly enrolled subjects. From among the 771 previously reported PERSEVERE subjects, there were 266 with an available corresponding RNA sample. The new group consisted of 118 subjects, generating a final cohort of 384 subjects with complete protein and mRNA data. From these, 307 subjects (80%) were randomly selected for deriving PERSEVEREXP, and the remaining 77 subjects were held back as an independent test cohort.

PERSEVERE Protein Biomarkers.

PERSEVERE includes C-C chemokine ligand 3 (CCL3), interleukin 8 (IL8), heat shock protein 70 kDa 1B (HSPA1B), granzyme B (GZMB), and matrix metallopeptidase 8 (MMP8) (28). Serum concentrations of these protein biomarkers were measured using a multi-plex magnetic bead platform (MILLIPLEX™ MAP) designed for this project by the EMO Millipore Corporation (Billerica, Mass.), and a Luminex® 100/200 System (Luminex Corporation, Austin, Tex.), according to the manufacturers' specifications. Assay performance data were previously published (28).

Multiplex mRNA Quantification.

Table 12 provides a list of the 68 previously unconsidered mortality risk assessment genes. Gene expression was measured using the NanoString nCounter™ and a custom-made codeset (NanoString Technologies, Seattle, Wash.). The technology is based on standard hybridization between the target gene, and target-specific capture and reporter probes to generate a digital readout of mRNA counts (11). All NanoString-based measurements were conducted at the University of Minnesota Genomics Center Core Facility. Four housekeeping genes were used to normalize the NanoString-derived expression data, as previously described (5): β-2-microglobulin (B2M), folylpolyglutamate synthase (FPGS), 2,4-dienoyl CoA reductase 1 (DECR1), and peptidylprolyl isomerase B (PPIB). Expression values were normalized to the geometric mean of the housekeeping genes.

Variable Reduction.

For deriving PERSEVERE-XP, it was planned a priori to reduce the number of genes considered by identifying biologically linked genes. The 68 mortality risk assessment genes were uploaded to the Ingenuity Pathway Analysis (IPA) discovery platform (Qiagen, Hilden, Germany) (12, 33, 35) to identify genes associated with any particular signaling pathways or gene networks. The network analysis was restricted to report only direct relationships between gene nodes. These genes are shown in Table 12.

TABLE 12

The 68 previously unconsidered mortality risk assessment genes, with the 18 genes selected after variable reduction indicated in italics.

| Gene Symbol | Description |
|---|---|
| ADGRE3 | adhesion G protein-coupled receptor E3 |
| *ANLN* | *anillin actin binding protein* |
| ANPEP | alanyl aminopeptidase, membrane |
| CASS4 | Cas scaffolding protein family member 4 |
| CCL3L1 | C-C motif chemokine ligand 3 like 1 |
| *CCNB1* | *cyclin B1* |
| CCNB2 | cyclin B2 |
| CD24 | CD24 molecule |
| CD302 | CD302 molecule |
| CD69 | CD69 molecule |
| CD86 | CD86 molecule |
| CDK1 | cyclin dependent kinase 1 |
| CEACAM8 | carcinoembryonic antigen related cell adhesion molecule 8 |
| *CEP55* | *centrosomal protein 55* |
| CKS2 | CDC28 protein kinase regulatory subunit 2 |
| CLEC5A | C-type lectin domain family 5 member A |
| *CLEC7A* | *C-type lectin domain family 7 member A* |
| CPVL | carboxypeptidase, vitellogenic like |
| CREB5 | cAMP responsive element binding protein 5 |
| CX3CR1 | C-X3-C motif chemokine receptor 1 |
| *DDIT4* | *DNA damage inducible transcript 4* |
| *DDX3Y* | *DEAD-box helicase 3, Y-linked* |
| DGAT2 | diacylglycerol 0-acyltransferase 2 |
| DNAJC3 | DnaJ heat shock protein family (Hsp40) member C3 |
| *F5* | *coagulation factor V* |
| FABP5 | fatty acid binding protein 5 |
| FAM157C | family with sequence similarity 157 member C |
| FGL2 | fibrinogen like 2 |
| FRY | FRY microtubule binding protein |
| FYB | FYN binding protein |
| GOS2 | G0/G1 switch 2 |
| GLIPRI | GLI pathogenesis related 1 |
| GPR171 | G protein-coupled receptor 171 |
| HAL | histidine ammonia-lyase |
| *HSPH1* | *heat shock protein family H (Hsp110) member 1* |
| KDM5D | lysine demethylase 5D |
| *KIF11* | *kinesin family member 11* |
| KREMEN1 | kringle containing transmembrane protein 1 |
| KRT23 | keratin 23 |
| MAFF | MAF bZIP transcription factor F |
| MANSC1 | MANSC domain containing 1 |
| *MME* | *membrane metallo-endopeptidase* |
| MT1M | metallothionein 1M |
| *NDC80* | *NDC80, kinetochore complex component* |
| NKG7 | natural killer cell granule protein 7 |
| *NUMB* | *NUMB, endocytic adaptor protein* |
| NUSAP1 | nucleolar and spindle associated protein 1 |
| ORM1 | orosomucoid 1 |
| PLXNC1 | plexin Cl |
| *PRC1* | *protein regulator of cytokinesis 1* |
| PRKAR1A | protein kinase cAMP-dependent type I regulatory subunit alpha |
| RGS1 | regulator of G-protein signaling 1 |
| RGS2 | regulator of G-protein signaling 2 |
| RNF182 | ring finger protein 182 |
| RNF24 | ring finger protein 24 |

TABLE 12-continued

The 68 previously unconsidered mortality risk assessment genes, with the 18 genes selected after variable reduction indicated in italics.

| Gene Symbol | Description |
| --- | --- |
| RPS4Y1 | ribosomal protein S4, Y-linked 1 |
| SLC39A8 | solute carrier family 39 member 8 |
| SLC8A1 | solute carrier family 8 member Al |
| SULF2 | sulfatase 2 |
| *TGFBI* | *transforming growth factor beta induced* |
| TLR6 | toll like receptor 6 |
| TNFRSF10C | TNF receptor superfamily member 10c |
| *TOP2A* | *topoisomerase (DNA) II alpha* |
| TTK | TTK protein kinase |
| TYMS | thymidylate synthetase |
| USP9Y | ubiquitin specific peptidase 9, Y-linked |
| WLS | wntless Wnt ligand secretion mediator |
| *ZWINT* | *ZW10 interacting kinetochore protein* |

Procedures for Deriving PERSEVERE-XP

Consistent with the previous approach to deriving PERSEVERE, Classification and Regression Tree (CART) methodology was used to derive PERSEVERE-XP (Salford Predictive Modeler v8.0, Salford Systems, San Diego, Calif.) (14, 15, 28, 30). The primary outcome variable for the modeling procedures was 28-day mortality. Predictor variables included the baseline 28-day mortality probability calculated using the previously validated PERSEVERE model (28), and the genes identified through variable reduction. Terminal nodes having <5% of the subjects in the root node were pruned, along with terminal nodes that did not improve classification. Weighting of cases and costs for misclassification were not used.

Other Statistical Analyses

Descriptive data are reported using medians, interquartile ranges, frequencies, and percentages. Comparisons between groups used the Mann-Whitney U-test, Chi-square, or Fisher's Exact tests, as appropriate. Descriptive statistics and comparisons used Sigma Stat Software (Systat Software, Inc., San Jose, Calif.). PERSEVERE-XP performance is reported using diagnostic test statistics with 95% confidence intervals computed using the score method as implemented by the VassarStats Website for Statistical Computation (see http<colon slash slash> vassarstats <dot> net). Areas under the receiver operating characteristic curves were compared using the method of Hanley and McNeil for non-independent samples (36).

Study Cohorts

Table 13 shows the demographic and clinical data for the two cohorts. There were no differences between the two cohorts. For both cohorts, non-survivors had higher baseline illness severity as measured by the PRISM-III score, and a higher PERSEVERE-based mortality probability, compared to the survivors. In the derivation cohort, no other differences were noted between the non-survivors and the survivors. In the test cohort, non-survivors had a higher rate of infection secondary to a gram-positive bacteria compared to the survivors. No other differences were noted.

TABLE 13

Clinical and demographic data for the derivation and test cohorts according to 28-day mortality.

| | Derivation Cohort | | Test Cohort | |
| --- | --- | --- | --- | --- |
| | Survivors | Non-survivors | Survivors | Non-survivors |
| N, (%) | 278 (91) | 29 (9) | 69 (90) | 8 (10) |
| Median age, yrs. (IQR) | 2.5 (1.0-6.5) | 1.4 (0.4-5.9) | 2.0 (0.6-5.5 | 0.9 (0.2-3.6) |
| Males, n (%) | 163 (59) | 29 (62) | 35 (51) | 4 (50) |
| Median PRISM, (IQR) | 11 (6-17) | 19 (13-29)$^a$ | 12 (8-17) | 19 (10-22)$^a$ |
| Mortality Probability (95% C.I.)$^b$ | 0.08 (0.06-0.10) | 0.28 (0.20-0.36)$^c$ | 0.05 (0.03-0.07) | 0.30 (0.18-0.42)$^c$ |
| Gram-positive bacteria, n (%) | 53 (19) | 7 (24) | 16 (23) | 5 (63)$^d$ |
| Gram-negative bacteria, n (%) | 62 (22) | 8 (28) | 18 (26) | 1 (13) |
| Other organism, n (%)$^e$ X | 36 (13) | 6 (21) | 10 (14) | 0 (0) |
| Culture negative, n (%) | 127 (46) | 8 (28) | 25 (36) | 2 (25) |
| Comorbidity, n (%) | 121 (44) | 13 (45) | 28 (41) | 1 (13) |
| Malignancy, n (%) | 18 (6) | 0 (0) | 6 (9) | 0 (0) |
| Immunosuppression, n (%) | 26 (9) | 3 (10) | 8 (12) | 0 (0) |
| Bone marrow transplantation, n (%) | 12 (4) | 0 (0) | 2 (3) | 0 (0) |

$^a$P < 0.05 vs. respective survivors, Chi Square test.
$^b$Based on PERSEVERE.
$^c$P < 0.05 vs. respective survivors, t-test.
$^d$P < 0.05 vs. respective survivors, Fisher Exact test.
$^e$Refers to viral, fungal, or mixed infections.

Example 9

TP53-Associated Gene Network

IPA analysis of the 68 mortality risk assessment genes revealed a gene network with tumor protein 53 (TP53, p.53) as a highly connected central node. Eighteen of the 68 mortality risk assessment genes are represented in this network (Table 14).

TABLE 14

List of genes in the network shown in FIG. 1, with genes corresponding to the 68 mortality risk assessment genes indicated in italics.

| Gene Symbol | Description |
| --- | --- |
| *ANLN* | *anillin actin binding protein* |
| BUB1B | BUB1 mitotic checkpoint serine/threonine kinase B |
| CENPC | centromere protein C |
| *CEP55* | *centrosomal protein 55* |
| CLEC7A | C-type lectin domain family 7 member A |

TABLE 14-continued

List of genes in the network shown in FIG. 1, with genes corresponding to the 68 mortality risk assessment genes indicated in italics.

| Gene Symbol | Description |
|---|---|
| *CCNB1* | *cyclin B1* |
| *CCNB2* | *cyclin B2* |
| *DDIT4* | *DNA damage inducible transcript 4* |
| *DDX3Y* | *DEAD-box helicase 3, Y-linked* |
| DSN1 | DSN1 homolog, MIS12 kinetochore complex component |
| EP300 | E1A binding protein p300 |
| *F5* | *coagulation factor V* |
| FEN1 | flap structure-specific endonuclease 1 |
| FOX01 | forkhead box 01 |
| *HAL* | *histidine ammonia-lyase* |
| HSPH1 | heat shock protein family H (Hsp110) member 1 |
| *KIF11* | *kinesin family member 11* |
| KMT5A | lysine methyltransferase 5A |
| MIS12 | MIS 12, kinetochore complex component |
| *MME* | *membrane metalloendopeptidase* |
| MSH2 | mutS homolog 2 |
| NCAPG | non-SMC condensin I complex subunit G |
| *NDC80* | *NDC80, kinetochore complex component* |
| NEK2 | NIMA related kinase 2 |
| NSL1 | NSL1, MIS12 kinetochore complex component |
| *NUMB* | *NUMB, endocytic adaptor protein* |
| PPARD | peroxisome proliferator activated receptor delta |
| *PRC1* | *protein regulator of cytokinesis 1* |
| SPC24 | SPC24, NDC80 kinetochore complex component |
| SPC25 | SPC25, NDC80 kinetochore complex component |
| *TGFBI* | *transforming growth factor beta induced* |
| TOP2A | topoisomerase (DNA) II alpha |
| TOP2B | topoisomerase (DNA) II beta |
| TP53 | tumor protein p53 |
| TRIB3 | tribbles pseudokinase 3 |
| *ZWINT* | *ZW10 interacting kinetochore protein* |

Figure 5:
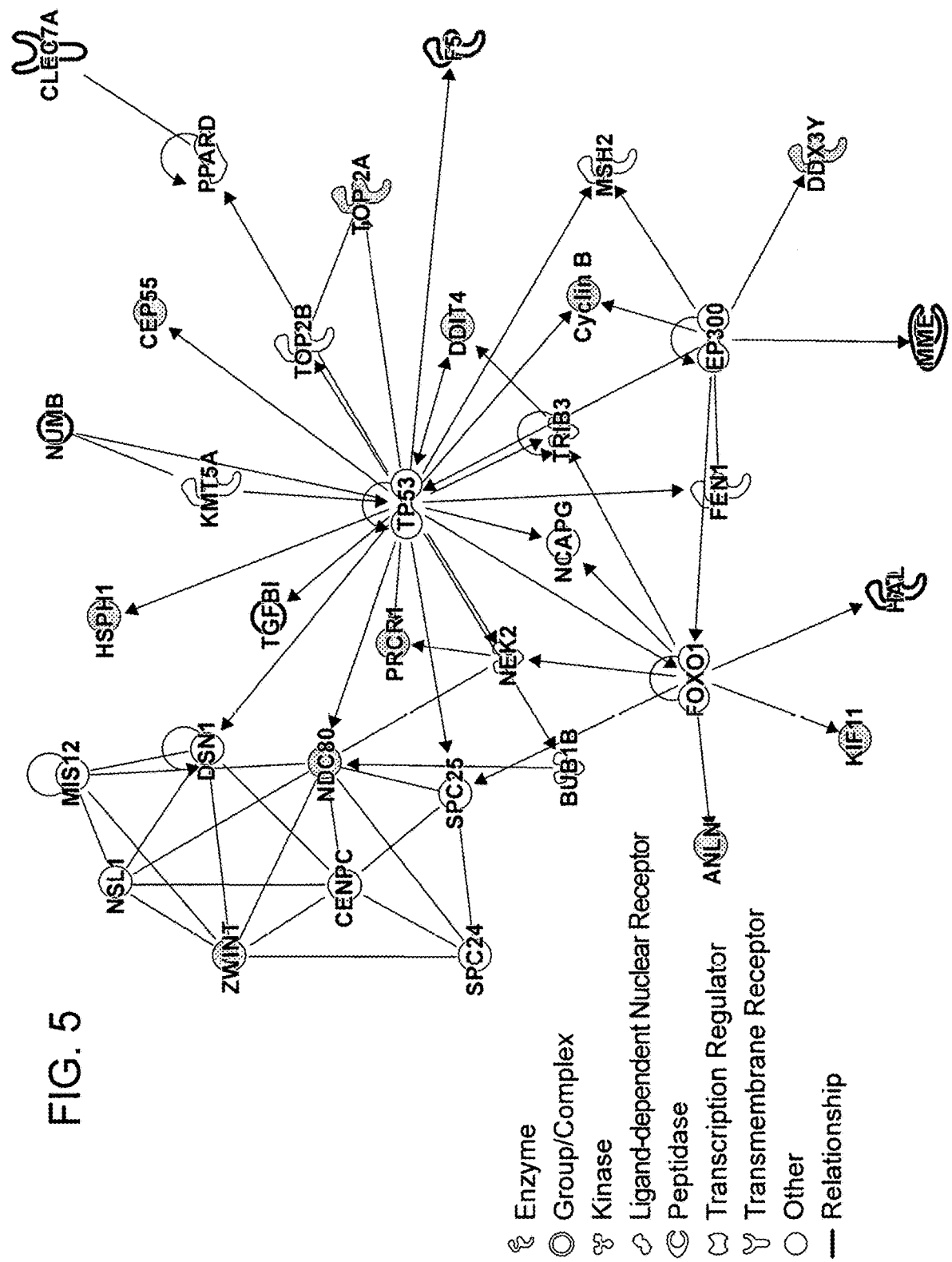
FIG. 5 depicts a gene network containing 18 of the 68 mortality risk assessment genes. The gene network was generated by uploading the 68 mortality risk assessment genes to the IPA discovery platform with the restriction of generating gene networks having direct relationships only. This was the highest scoring network resulting from the analysis (network score=30). The score reflects the probability of generating the network based on random input of 35 network eligible genes. The score is generated by the equation: −log(p value, Fisher's Exact Test), meaning that the p value=1E-30. The gene network is centered on a TP53 gene node (p53), which was not part of the 68 mortality risk assessment genes. The 18 genes are shown in Table 14. Shaded nodes depict increased gene expression in non-survivors relative to the survivors, whereas boldened nodes depict decreased gene expression in the non-survivors relative to the survivors. CCNB1 and CCNB2 are depicted as "cyclin B" in the network. Relationship lines with arrows indicate a direct modification (e.g. activation, transcription, phosphorylation, or cleavage). Relationship lines without arrows indicate a direct interaction (e.g. protein-protein, correlation, or RNA-RNA).

FIG. 5 shows the TP53-associated gene network, with the 18 gene nodes corresponding to the mortality risk assessment genes shown in shaded nodes to depict increased gene expression in the non-survivors relative to the survivors, or boldened nodes to depict decreased gene expression in the non-survivors relative to the survivors. Functionally, the gene network corresponds to cell cycle, cell cycle arrest, cellular assembly and organization, and DNA replication, recombination, and repair.

Example 8

PERSEVERE-XP Derivation

Figure 6:
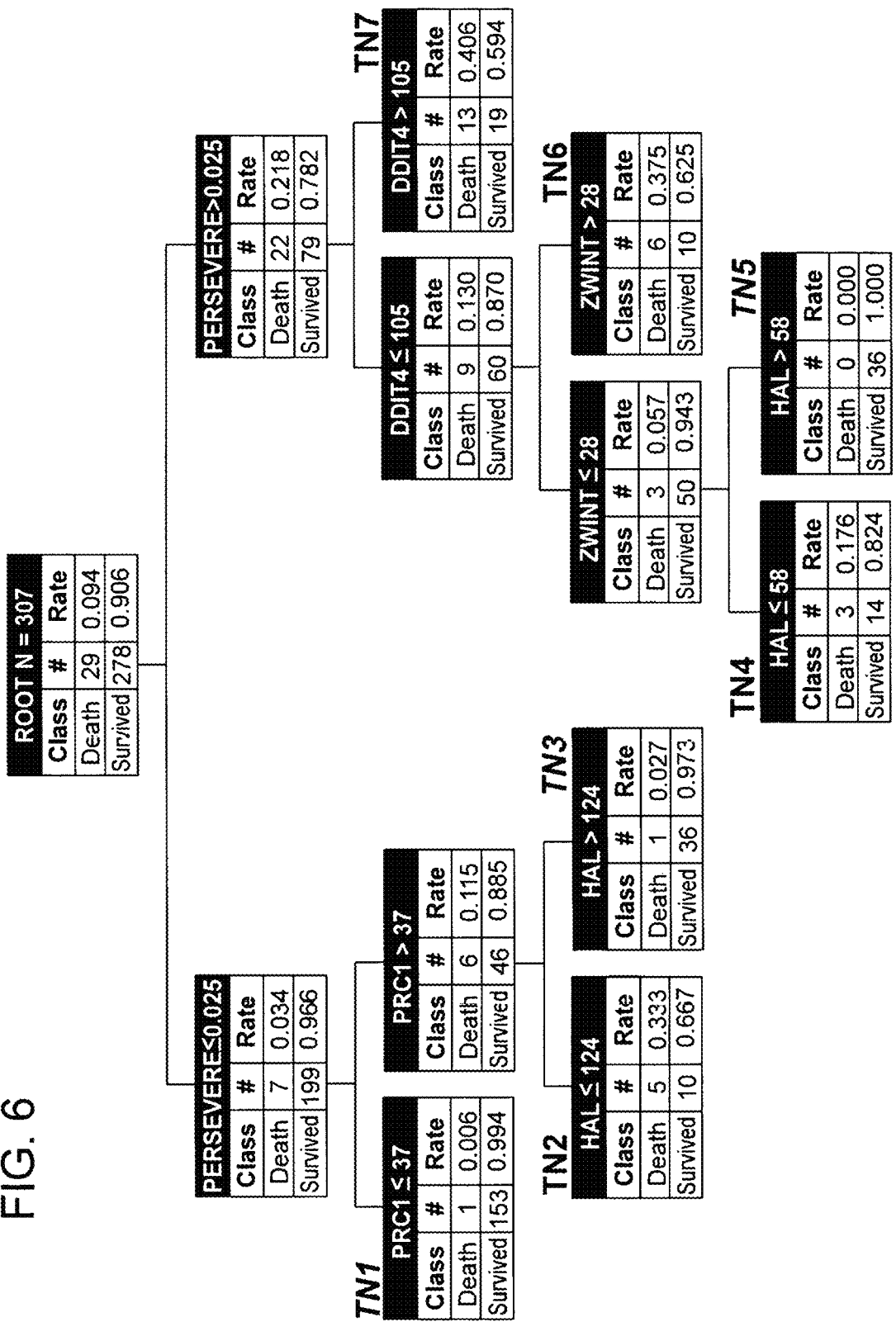
FIG. 6 depicts the derived PERSEVERE-XP decision tree. The decision tree contains the PERSEVERE-based mortality probability, protein regulator of cytokinesis 1 (PRC1), histidine ammonialyase (HAL), DNA damage inducible transcript 4 (DDIT4), and ZW10 interacting kinetochore protein (ZWINT). The gene expression values are provided in arbitrary units of mRNA counts, as generated by the NanoString nCounter platform and normalized to four housekeeping genes. The root node provides the total number of non-survivors and survivors in the derivation cohort, and the respective rates. Each daughter node provides the respective decision rule criterion based on either the PERSEVERE-based mortality probability or a gene expression level, and the number of non-survivors and survivors, with the respective rates. Terminal nodes (TN) TN1, TN3, and TN5 (highlighted by italics) contain subjects having a low risk/probability of mortality (0.000 to 0.027), whereas TN2, TN4, TN6, and TN7 (highlighted by bolding) contain subjects having a higher probability of mortality (0.176 to 0.406).

The 18 genes of Table 14 and the PERSEVERE-based mortality probability were used as predictor variables to derive a model estimating the risk of 28 day mortality, termed PERSEVERE-XP. FIG. 6 shows the derived PERSEVERE-XP decision tree, which had an area under the receiver operating characteristic curve of 0.90 (95% C.I.: 0.85 to 0.95) for differentiating between survivors and non-survivors. The PERSEVERE-based mortality probability occupied the first level decision rule. DDIT4, HAL, PRC1, and ZWINT contributed to the subsequent decision rules. None of the other mortality risk assessment genes in the network contributed to the decision tree. Subjects allocated to terminal nodes (TN) 1, 3, and 5 had a low probability of mortality (0.000 to 0.027), whereas subjects allocated to terminal nodes 2, 4, 6, and 7 had a higher probability of mortality (0.176 to 0.406). Among the 227 subjects allocated to the low risk terminal nodes, 2 (1%) died by 28 days. Conversely, among the 80 subjects allocated to the higher risk terminal nodes, 27 (34%) died by 28 days.

Figure 7:
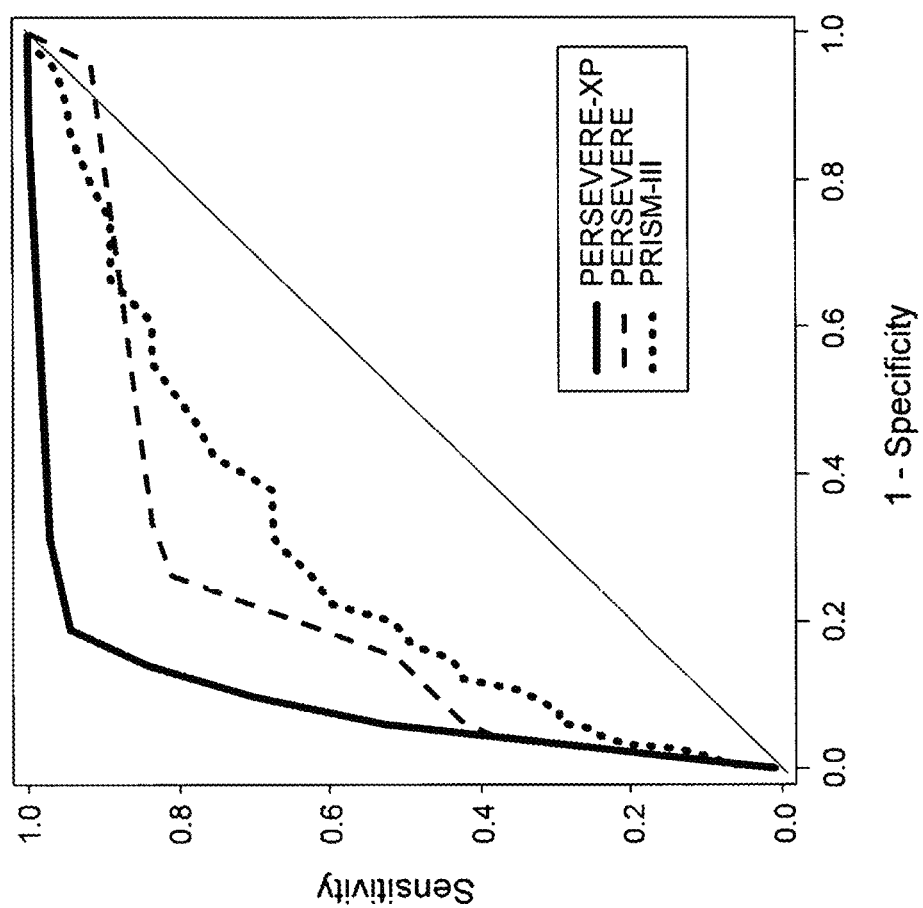
FIG. 7 depicts the classification of the test cohort subjects according to PERSEVERE-XP. The test cohort subjects (n=77) were classified according to PERSEVERE-XP without any modifications. The same conventions apply to the decision tree as described for FIG. 6.

FIG. 7 shows the classification of the test cohort subjects according to PERSEVERE-XP. This classification yielded an area under the receiver operating characteristic curve of 0.96 (95% C.I.: 0.91 to 1.0). Among the 56 test cohort subjects allocated to the low risk terminal nodes, none died by 28 days. Conversely, among the 21 test cohort subjects allocated to the higher risk terminal nodes, 8 (38%) died by 28 days.

PERSEVERE-XP can be accurately interpreted as a risk continuum, but the classifications are convertible to a binary format for calculating diagnostic test characteristics. Table 15 provides the diagnostic test characteristics for both the derivation and test cohorts when classifying subjects with a PERSEVERE-XP mortality probability ≤0.027 as survivors, and those with a PERSEVERE-XP mortality probability ≤0.176 as non-survivors.

TABLE 15

Diagnostic test characteristics of PERSEVERE-XP in the derivation and test cohorts.

| | Derivation Cohort | | Test Cohort | |
|---|---|---|---|---|
| Variable | Value | 95% C.I. | Value | 95% C.I. |
| True Positives, n | 27 | — | 8 | — |
| True Negatives, n | 225 | — | 56 | — |
| False Positives, n | 53 | — | 13 | — |
| False Negatives, n | 2 | — | 0 | — |
| Sensitivity | 93% | 76-99 | 100% | 60-100 |
| Specificity | 81% | 76-85 | 81% | 70-89 |
| Positive Predictive Value | 34% | 24-45 | 38% | 19-61 |
| Negative Predictive Value | 99% | 97-100 | 100% | 92-100 |
| (+) Likelihood Ratio | 4.9 | 3.8-6.3 | 5.3 | 3.3-8.7 |
| (−) Likelihood Ratio | 0.09 | 0.02-0.33 | — | — |

Example 10

PERSEVERE-XP Performance

Figure 8:
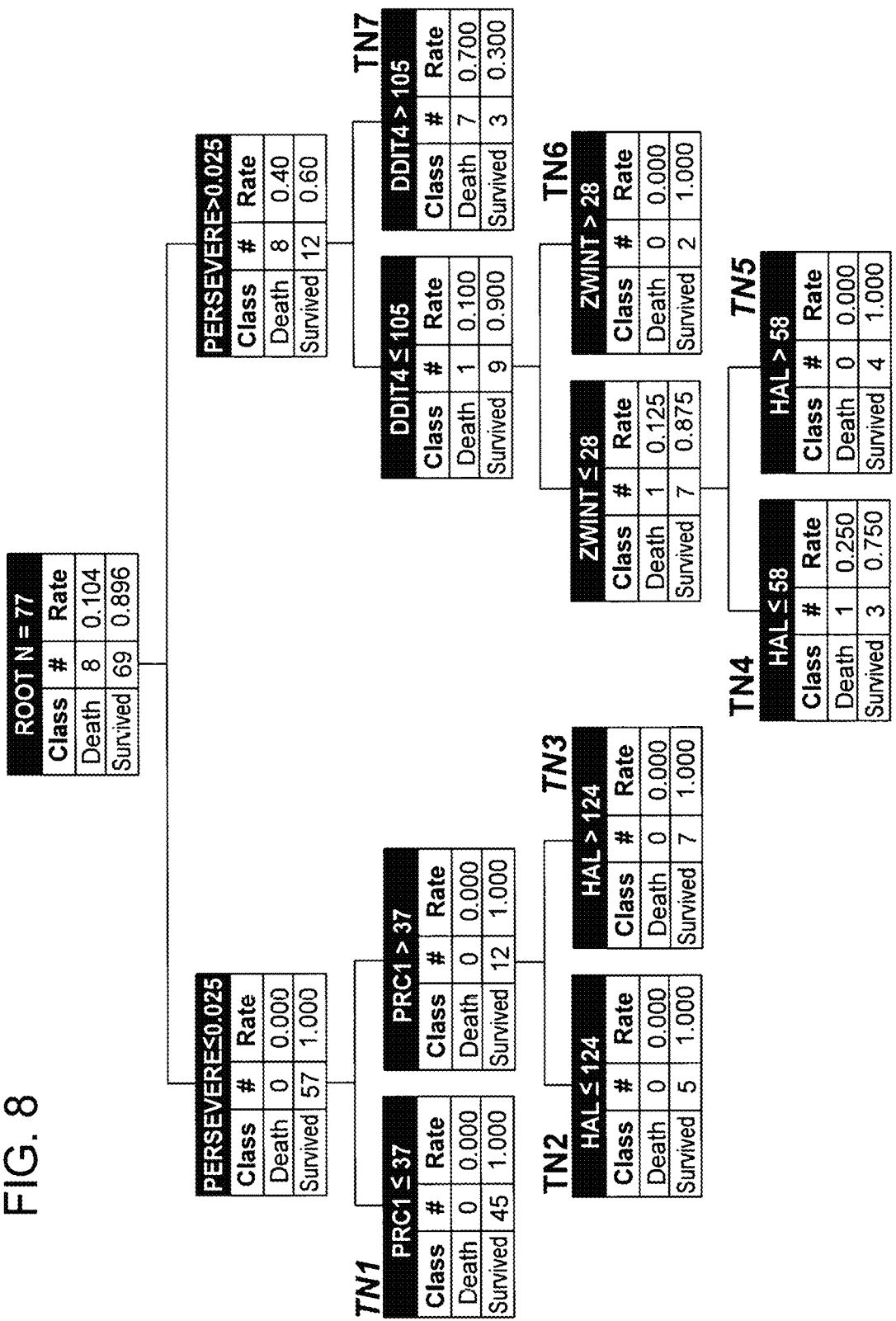
FIG. 8 depicts a comparison of the receiver operating characteristic curves for PERSEVERE-XP, PERSEVERE, and PRISM-III. The respective curves reflect the combined derivation and test cohorts (n=384). The area under the receiver operating characteristic curve of PERSEVERE-XP (0.91; 95% C.I.: 0.87 to 0.95) was found to be superior to that of PERSEVERE (0.78; 95% C.I. 0.68 to 0.87; p=0.002) and PRISM (0.72; 0.63 to 0.82; p<0.001).

Next the derivation and test cohorts (n=384) were combined, and the performance of PERSEVERE-XP was compared to that of PERSEVERE and PRISM-III for differentiating between survivors and non-survivors. FIG. 8 shows that the area under the receiver operating characteristic curve of PERSEVERE-XP (0.91; 95% C.I.: 0.87 to 0.95) was superior to that of PERSEVERE (0.78; 95% C.I.: 0.68 to 0.87; p=0.002) and PRISM-III (0.72; 0.63 to 0.82; p<0.001). Table 16 compares the diagnostic test characteristics of PERSEVERE-XP and PERSEVERE in the combined derivation and test cohorts based on a binary classification.

TABLE 16

Diagnostic test characteristics of PERSEVERE-XP and PERSEVERE in the combined derivation and test cohorts.

| | PEREVERE-XP | | PERSEVERE | |
|---|---|---|---|---|
| Variable | Value | 95% C.I. | Value | 95% C.I. |
| True Positives, n | 35 | — | 30 | — |
| True Negatives, n | 281 | — | 256 | — |
| False Positives, n | 66 | — | 91 | — |
| False Negatives, n | 2 | — | 7 | — |
| Sensitivity | 95% | 80-99 | 81% | 64-91 |
| Specificity | 81% | 76-85 | 74% | 69-78 |
| Positive Predictive Value | 35% | 26-45 | 25% | 18-34 |
| Negative Predictive Value | 99% | 97-100 | 97% | 94-99 |

TABLE 16-continued

Diagnostic test characteristics of PERSEVERE-XP and PERSEVERE in the combined derivation and test cohorts.

| Variable | PEREVERE-XP | | PERSEVERE | |
|---|---|---|---|---|
| | Value | 95% C.I. | Value | 95% C.I. |
| (+) Likelihood Ratio | 5 | 4.0-6.3 | 3.1 | 2.4-3.9 |
| (−) Likelihood Ratio | 0.07 | 0.02-0.36 | 0.3 | 0.1-0.5 |

To understand reasons for misclassification by PERSEVERE-XP, those predicted to be non-survivors but who survived (false positives) were compared to those who were predicted to survive and did so (true negatives). The 66 false positive subjects had a higher PRISM-III score, a greater number of days in the PICU, a greater maximum number of organ failures, and a greater proportion had persistent multiple organ failure at day seven of septic shock when compared with the 281 true negative subjects, shown in Table 17.

TABLE 17

Comparison of clinical characteristics reflecting illness severity, between the false positives and true negatives generated by PERSEVERE-XP in the combined derivation and test cohorts.

| | False Positives | True Negatives | P value |
|---|---|---|---|
| N | 66 | 281 | |
| Median PRISM Score (IQR) | 14 (9-22) | 11 (6-16) | <0.001 |
| Median PICU Days (IQR) | 11 (7-17) | 7 (3-13) | <0.001 |
| Median Maximum Number of Organ Failures (IQR) | 2 (2-3) | 2 (2-2) | <0.001 |
| Multiple Organ Failure at ICU Day 7, n (%) | 24 (36) | 40 (14) | <0.001 |

There were only two false negative subjects, and so a similar analysis was not performed to compare false negatives and true positives. One of the false negative subjects was previously healthy, but presented with idiopathic fulminant liver failure and developed septic shock secondary to *Pseudomonas aeruginosa*. The other false negative subject had aplastic anemia and developed septic shock in association with disseminated Cytomegalovirus.

Example 11

TP53 Expression

Figure 9:
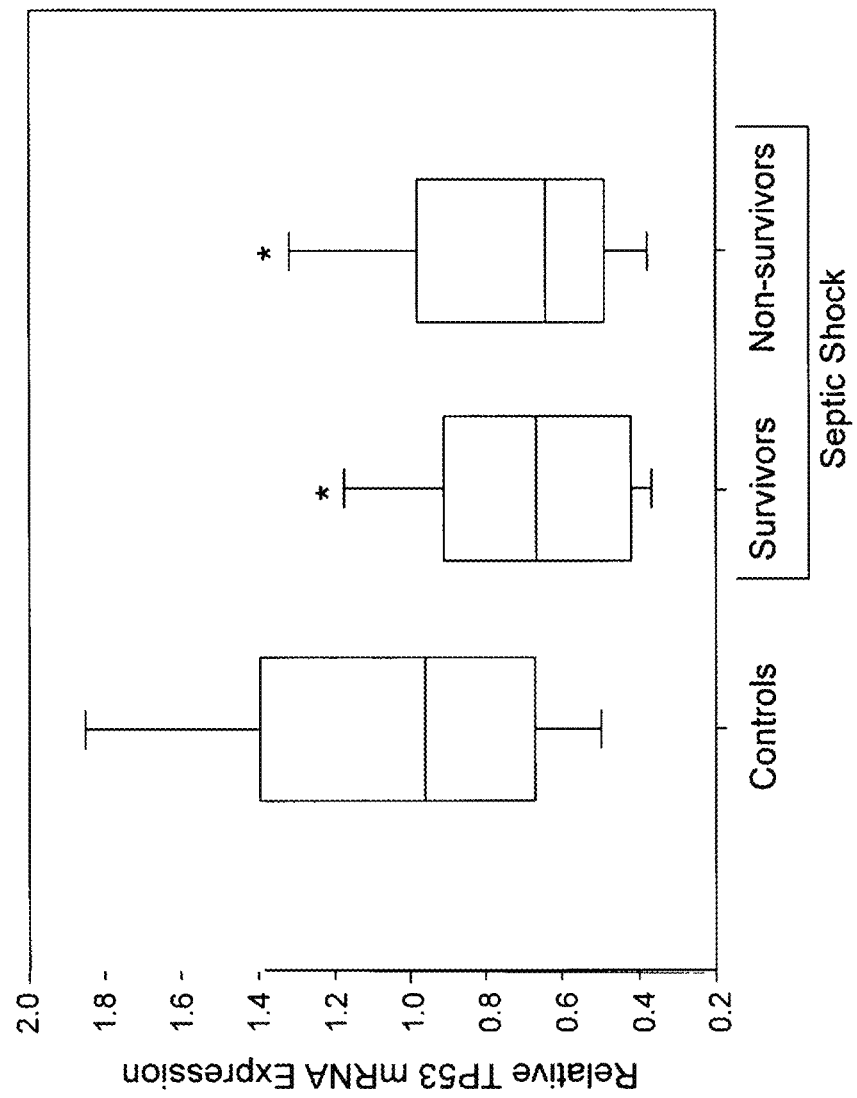
FIG. 9 depicts box-whisker plots comparing TP53 expression among healthy controls, septic shock survivors, and septic shock non-survivors. The data were obtained from the existing pediatric septic shock gene expression database, generated using microarray methodology (Gene Expression Omnibus Accession Number: GSE66099). *p<0.05 vs. healthy controls (n=52). TP 531 gene expression was not significantly different between septic shock survivors (n=151) and non-survivors (n=29).

Since the primary gene network identified during variable reduction contains TP53 as a highly connected node, it was next determined if TP53 is differentially regulated between pediatric septic shock survivors and non-survivors. Because TP53 was not specifically measured for this study, the existing, microarray-based gene expression database of pediatric septic shock (Gene Expression Omnibus Accession Number: GSE66099) was interrogated. As shown in FIG. 9, TP53 expression was significantly decreased in children with septic shock, relative to healthy controls (n=52), but was not significantly different when comparing survivors (n=151) and non-survivors (n=29).

Example 12

Combining Prognostic and Predictive Enrichment

The prognostic and predictive enrichment strategies have been combined to determine whether there exists an identifiable group of children with septic shock who are more likely to benefit from corticosteroids.

Study Subjects and Data Collection.

A secondary analysis of previously published data (5, 28) was conducted, involving 288 previously published pediatric subjects with septic shock. The protocol for collection and use of biological specimens and clinical data was approved by the institutional review boards of each of the 18 participating institutions. Children 10 years old or younger admitted to a PICU and meeting pediatric-specific consensus criteria for septic shock were eligible for enrollment (8). There were no exclusion criteria, other than the inability to obtain informed consent, which was obtained from parents or legal guardians. The consent allows for secondary analyses.

Blood samples were obtained within 24 hours of meeting criteria for septic shock. Clinical and laboratory data were collected daily while in the PICU. Organ failure data were tracked up to day 7 of septic shock using previously published criteria (8). Mortality was tracked for 28 days after enrollment. Illness severity was estimated using the Pediatric Risk of Mortality (PRISM) score (9).

PERSEVERE and Endotype Identification

Baseline mortality probability was estimated using PERSEVERE, which is calculated from the biomarkers C-C chemokine ligand 3, interleukin 8, heat shock protein 70kDa 1B, granzyme B, and matrix metallopeptidase 8 (28). Each study subject was classified as low, intermediate, or high risk. Because there were only 31 subjects in the high-risk group, this group was combined with the intermediate-risk group for analysis, thus generating an intermediate-high risk group (n=93). Endotypes were assessed from whole blood-derived RNA using a digital mRNA quantification platform (5). Gene expression data for each study subject was depicted using gene expression mosaics, and each subject was assigned to endotype A or B using computer-assisted image analysis and reference mosaics.

Data Analysis

The primary study endpoint was complicated course, defined as the persistence of two or more organ failures at day 7 of septic shock or 28-day mortality (5). 28-Day morality alone was not considered due to the low death rate in this cohort. Logistic regression was used to test for an association between corticosteroids and complicated course within endotype. Results were adjusted for PRISM score, risk category, and an interaction between risk category and exposure to corticosteroids was tested for. Since PRISM is based primarily on physiologic variables while PERSEVERE is based on biomarkers, and since the correlation coefficient between the two was low (r=0.292), both risk variables were included in the analysis. Since the primary study endpoint was not rare, the odds ratios generated by logistic regression were converted to relative risk using the method suggested by Zhang and Yu (62). Analyses used SPSS v 23.0 (IBM, Armonk, N.Y.).

Results

Among the 300 subjects (described in (5)) included in the derivation and validation of the septic shock endotypes, 288 (96%) had PERSEVERE data and were included in the analysis. Among the 112 endotype A subjects, 49 subjects (44%) had a complicated course. Among the 176 endotype B subjects, 37 subjects (21%) had a complicated course. Fifty-one endotype A subjects (46%) and 101 endotype B subjects (57%) were exposed to corticosteroids.

Table 18 shows the relative risks for complicated course derived from the logistic regression models. Among endotype A subjects, only the PERSEVERE risk category was associated with increased risk of complicated course, although there was a trend toward increased risk of complicated course with increased PRISM score. Among endotype B subjects, the PRISM and PERSEVERE risk categories were independently associated with increased risk of complicated course. Corticosteroid exposure was not associated with decreased risk of complicated course in endotype B subjects at low PERSEVERE risk, but in those at intermediate to high PERSEVERE risk, corticosteroids were associated with more than a 10-fold reduction in the risk of a complicated course.

TABLE 18

Results of logistic regression to test the association between corticosteroids and complicated course using prognostic and predictive enrichment strategies.

| Septic Shock Endotype | Variable | Relative Risk (95% CI) | p |
|---|---|---|---|
| Endotype A | PRISM | 1.03 (1.00-1.06) | 0.052 |
| | PERSEVERE | 2.05 (1.76-2.18) | <0.001 |
| | Corticosteroids | 1.35 (0.81-1.81) | 0.212 |
| | PERSEVERE × corticosteroids | 1.03 (0.24-1.95) | 0.957 |
| Endotype B | PRISM | 1.08 (1.04-1.12) | <0.001 |
| | PERSEVERE | 3.45 (2.40-4.15) | <0.001 |
| | Corticosteroids | 0.73 (0.32-1.51) | 0.431 |
| | PERSEVERE × corticosteroids | 0.09 (0.01-0.54) | 0.007 |

Among endotype B subjects at intermediate to high pediatric sepsis biomarker risk model-based risk of mortality, corticosteroids were independently associated with more than a 10-fold reduction in the risk of a complicated course (relative risk, 0.09; 95% CI, 0.01-0.54; p=0.007. These results demonstrate that a combination of prognostic and predictive strategies based on serum protein and messenger RNA biomarkers can identify a subgroup of children with septic shock who may be more likely to benefit from corticosteroids.

Example 13

Combining PERSEVERE-XP with Endotyping Strategy

As described in the preceding example, prognostic and predictive enrichment strategies can be combined to identify a patient population of children with septic shock who are more likely to benefit from corticosteroids.

The PERSEVERE-XP mortality probability/mortality risk stratification based on the PERSEVERE serum protein biomarkers and the TP53 mRNA biomarkers, as described herein, therefore can be used in combination with the patient endotyping strategy described herein involving two or more selected from the group consisting of JAK2, LYN, PRKCB, and SOS2. The combined results can identify which patients are more likely to benefit from corticosteroids.

The PERSEVERE-XP mortality probability/mortality risk is determined for a pediatric patient identified by the methods described herein to be endotype B. If the patient has a high mortality risk as determined by PERSEVERE-XP as defined herein, the risk of complicated course is reduced, and the patient is treated with corticosteroids. If the patient is identified by the methods described herein to be endotype A and has a high mortality risk as determined by PERSEVERE-XP as defined herein, the patient is treated with one or more therapy excluding corticosteroids.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

1. Cohen J, Vincent J L, Adhikari N K, Machado F R, Angus D C, Calandra T, Jaton K, Giulieri S, Delaloye J, Opal S et al.: Sepsis: a roadmap for future research. *The Lancet Infectious Diseases* 2015, 15(5):581-614.
2. Wong H R, Cvijanovich N, Lin R, Allen G L, Thomas N J, Willson D F, Freishtat R J, Anas N, Meyer K, Checchia P A et al.: Identification of pediatric septic shock subclasses based on genome-wide expression profiling. *BMC Medicine* 2009, 7:34.
3. Wong H R, Cvijanovich N Z, Allen G L, Thomas N J, Freishtat R J, Anas N, Meyer K, Checchia P A, Lin R, Shanley T P et al.: Validation of a gene expression-based subclassification strategy for pediatric septic shock. *Critical Care Medicine* 2011, 39(11):2511-2517.
4. Wong H R, Wheeler D S, Tegtmeyer K, Poynter S E, Kaplan J M, Chima R S, Stalets E, Basu R K, Doughty L A: Toward a clinically feasible gene expression-based subclassification strategy for septic shock: proof of concept. *Critical Care Medicine* 2010, 38(10):1955-1961,
5. Wong H R, Cvijanovich N Z, Anas N, Allen G L, Thomas N J, Bigham M T, Weiss S L, Fitzgerald J, Checchia P A, Meyer K et al.: Developing a clinically feasible personalized medicine approach to pediatric septic shock. *Am J Respir Crit Care Med* 2015, 191(3):309-315.
6. Wong H R, Atkinson S J, Cvijanovich N Z, Anas N, Allen G L, Thomas N J, Bigham M T, Weiss S L, Fitzgerald J C, Checchia P A et al.: Combining prognostic and predictive enrichment strategies to identify children with septic shock responsive to corticosteroids. *Critical Care Medicine* 2016.
7. Maslove D M, Wong H R: Gene expression profiling in sepsis: timing, tissue, and translational considerations. *Trends in Molecular Medicine* 2014, 20(4):204-213.
8. Wong H R, Shanley T P, Sakthivel B, Cvijanovich N, Lin R, Allen G L, Thomas N J, Doctor A, Kalyanaraman M, Tofil N M et al.: Genome-level expression profiles in pediatric septic shock indicate a role for altered zinc homeostasis in poor outcome. *Physiological Genomics* 2007, 30(2):146-155.
9. Pollack M M, Patel K M, Ruttimann U E: The Pediatric Risk of Mortality III-Acute Physiology Score (PRISM III-APS): a method of assessing physiologic instability for pediatric intensive care unit patients. *The Journal of Pediatrics* 1997, 131(4):575-581.
10. Atkinson S J, Cvijanovich N Z, Thomas N J, Allen G L, Anas N, Bigham M T, Hall M, Freishtat R J, Sen A, Meyer K et al.: Corticosteroids and pediatric septic shock outcomes: a risk stratified analysis. *PloS One* 2014, 9(11): e112702.
11. Geiss G K, Bumgarner R E, Birditt B, Dahl T, Dowidar N, Dunaway D L, Fell H P, Ferree S, George R D, Grogan T et al.: Direct multiplexed measurement of gene expression with color-coded probe pairs. *Nature Biotechnology* 2008, 26(3):317-325.
12. Wynn J L, Cvijanovich N Z, Allen G L, Thomas N J, Freishtat R J, Anas N, Meyer K, Checchia P A, Lin R, Shanley T P et al.: The influence of developmental age on the early transcriptomic response of children with septic shock. *Mol Med* 2011, 17(11-12):1146-1156.
13. Weiss S L, Cvijanovich N Z, Allen G L, Thomas N J, Freishtat R J, Anas N, Meyer K, Checchia P A, Shanley T P, Bigham M T et al.: Differential expression of the nuclear-encoded mitochondrial transcriptome in pediatric septic shock. *Crit Care* 2014, 18(6):623.
14. Che D, Liu Q, Rasheed K, Tao X: Decision tree and ensemble learning algorithms with their applications in bioinformatics. *Advances in Experimental Medicine and Biology* 2011, 696:191-199.
15. Muller R, Mockel M: Logistic regression and CART in the analysis of multimarker studies. *Clinica Chimica Acta; International Journal of Clinical Chemistry* 2008, 394(1-2):1-6.
16. Mathias B, Szpila B E, Moore F A, Efron P A, Moldawer L L: A Review of GM-CSF Therapy in Sepsis. *Medicine* 2015, 94(50):e2044.
17. Marlow N, Morris T, Brocklehurst P, Carr R, Cowan F, Patel N, Petrou S, Redshaw M, Modi N, Dore C J: A randomised trial of granulocyte-macrophage colony-stimulating factor for neonatal sepsis: childhood outcomes at 5 years. *Archives of Disease in Childhood Fetal and Neonatal Edition* 2015, 100(4):F320-326.
18. Hutchins N A, Unsinger J, Hotchkiss R S, Ayala A: The new normal: immunomodulatory agents against sepsis immune suppression. *Trends in Molecular Medicine* 2014, 20(4):224-233.
19. Sprung C L, Annane D, Keh D, Moreno R, Singer M, Freivogel K, Weiss Y G, Benbenishty J, Kalenka A, Forst H et al.: Hydrocortisone therapy for patients with septic shock. *The New England Journal of Medicine* 2008, 358(2):111-124.
20. Annane D, Sebille V, Charpentier C, Bollaert P E, Francois B, Korach J M, Capellier G, Cohen Y, Azoulay E, Troche G et al.: Effect of treatment with low doses of hydrocortisone and fludrocortisone on mortality in patients with septic shock. *Jama* 2002, 288(7):862-871.
21. Atkinson S J, Wong H R: Identifying critically ill patients who may benefit from adjunctive corticosteroids: not as easy as we thought. *Pediatric Critical Care Medicine: A Journal of the Society of Critical Care Medicine and the World Federation of Pediatric Intensive and Critical Care Societies* 2014, 15(8):769-771.
22. Manukyan M C, Weil B R, Wang Y, Abarbanell A M, Herrmann J L, Poynter J A, Meldrum D R: The phosphoinositide-3 kinase survival signaling mechanism in sepsis. *Shock* 2010, 34(5):442-449.
23. Sabio G, Davis R J: TNF and MAP kinase signalling pathways. *Seminars in Immunology* 2014, 26(3):237-245.
24. Fan H, Goodwin A J, Chang E, Zingarelli B, Borg K, Guan S, Halushka P V, Cook J A: Endothelial progenitor cells and a stromal cell-derived factor-lalpha analogue synergistically improve survival in sepsis. *Am J Respir Crit Care Med* 2014, 189(12):1509-1519.
25. Guo C, Goodwin A J, Buie J N, Cook J A, Halushka P V, Argraves K, Zingarelli B, Zhang X K, Wang L, Fan H: A Stromal Cell-derived Factor 1 alpha Analogue Improves Endothelial Cell Function in Lipopolysaccharide-induced Acute Respiratory Distress *Syndrome. Mol Med* 2016, 22:115-123.
26. Wong H R, Atkinson S J, Cvijanovich N Z, Anas N, Allen G L, Thomas N J, Bigham M T, Weiss S L, Fitzgerald J C, Checchia P A, et al. Combining prognostic and predictive enrichment strategies to identify children with septic shock responsive to corticosteroids. *Crit Care Med* 2016, 44:e1000-1003.
27. Prescott H C, Calfee C S, Thompson B T, Angus D C, Liu V X. Toward smarter lumping and smarter splitting: Rethinking strategies for sepsis and acute respiratory distress syndrome clinical trial design. *Am J Respir Crit Care Med* 2016, 194:147-155.
28. Wong H R, Salisbury S, Xiao Q, Cvijanovich N Z, Hall M, Allen G L, Thomas N J, Freishtat R J, Anas N, Meyer K, Checchia P A, Lin R, Shanley T P, Bigham M T, Sen A, Nowak J, Quasney M, Henricksen J W, Chopra A, Banschbach S, Beckman E, Harmon K, Lahni P, Lindsell C J. The pediatric sepsis biomarker risk model. *Crit Care* 2012, 16:R174.
29. Wong H R, Weiss S L, Giuliano J S, Jr., Wainwright M S, Cvijanovich N Z, Thomas N J, Allen G L, Anas N, Bigham M T, Hall M, Freishtat R J, Sen A, Meyer K, Checchia P A, Shanley T P, Nowak J, Quasney M, Chopra A, Fitzgerald J C, Gedeit R, Banschbach S, Beckman E, Lahni P, Hart K, Lindsell C J. Testing the prognostic accuracy of the updated pediatric sepsis biomarker risk model. *PLoS One* 2014, 9:e86242.
30. Wong H R, Cvijanovich N Z, Anas N, Allen G L, Thomas N J, Bigham M T, Weiss S L, Fitzgerald J, Checchia P A, Meyer K, Quasney M, Hall M, Gedeit R, Freishtat R J, Nowak J, Raj S S, Gertz S, Howard K, Harmon K, Lahni P, Frank E, Hart T C, Nguyen T C, Lindsell C J. Persevere II: Redefining the pediatric sepsis biomarker risk model with septic shock phenotype. *Crit Care Med* 2016, 44:2010-2017.
31. Alder M N, Lindsell C J, Wong H R. The pediatric sepsis biomarker risk model: Potential implications for sepsis therapy and biology. *Expert Rev Anti Infect Ther* 2014, 12:809-816.
32. Kaplan J M, Wong H R. Biomarker discovery and development in pediatric critical care medicine. *Pediatr Crit Care Med* 2011, 12:165-173.
33. Shanley T P, Cvijanovich N, Lin R, Allen G L, Thomas N J, Doctor A, Kalyanaraman M, Tofil N M, Penfil S, Monaco M, Odoms K, Barnes M, Sakthivel B, Aronow B J, Wong H R. Genome-level longitudinal expression of signaling pathways and gene networks in pediatric septic shock. *Mol Med* 2007, 13:495-508.
34. Goldstein B, Giroir B, Randolph A. International pediatric sepsis consensus conference: Definitions for sepsis and organ dysfunction in pediatrics. *Pediatr Crit Care Med* 2005, 6:2-8.
35. Laudanski K, Miller-Graziano C, Xiao W, Mindrinos M N, Richards D R, De A, Moldawer L L, Maier R V, Bankey P, Baker H V, Brownstein B H, Cobb J P, Calvano S E, Davis R W, Tompkins R G. Cell-specific expression and pathway analyses reveal alterations in trauma-related human t cell and monocyte pathways. *Proc Natl Acad Sci USA* 2006, 103:15564-15569.
36. Hanley J A, McNeil B J. A method of comparing the areas under receiver operating characteristic curves derived from the same cases. *Radiology* 1983, 148:839-843.
37. Cooks T, Harris C C, Oren M. Caught in the cross fire: P53 in inflammation. *Carcinogenesis* 2014, 35:1680-1690.
38. Johnson R F, Perkins N D. Nuclear factor-kappab, p53, and mitochondria: Regulation of cellular metabolism and the warburg effect. *Trends Biochm Sci* 2012, 37:317-324.
39. Maiuri M C, Galluzzi L, Morselli E, Kepp O, Malik S A, Kroemer G. Autophagy regulation by p53. *Curr Opin Cell Biol* 2010, 22:181-185.
40. Tan M, Li S, Swaroop M, Guan K, Oberley L W, Sun Y. Transcriptional activation of the human glutathione peroxidase promoter by p53. *J Biol Chem* 1999, 274:12061-12066.
41. Yoon K A, Nakamura Y, Arakawa H. Identification of aldh4 as a p53-inducible gene and its protective role in cellular stresses. *J Hum Genet* 2004, 49:134-140.
42. Hofseth L J, Saito S, Hussain S P, Espey M G, Miranda K M, Araki Y, Jhappan C, Higashimoto Y, He P, Linke S P, Quezado M M, Zurer I, Rotter V, Wink D A, Appella E, Harris C C. Nitric oxide-induced cellular stress and p53 activation in chronic inflammation. *Proc Natl Acad Sci USA* 2003, 100:143-148.
43. Murphy S H, Suzuki K, Downes M, Welch G L, De Jesus P, Miraglia L J, Orth A P, Chanda S K, Evans R M, Verma I M. Tumor suppressor protein (p)53, is a regulator of nf-kappab repression by the glucocorticoid receptor. *Proc Natl Acad Sci USA* 2011, 108:17117-17122.
44. Komarova E A, Krivokrysenko V, Wang K, Neznanov N, Chernov M V, Komarov P G, Brennan M L, Golovkina T V, Rokhlin O W, Kuprash D V, Nedospasov S A, Hazen S L, Feinstein E, Gudkov A V. P53 is a suppressor of inflammatory response in mice. *FASEB J* 2005, 19:1030-1032.
45. Hotchkiss R S, Tinsley K W, Hui J J, Chang K C, Swanson P E, Drewry A M, Buchman T G, Karl IE. P53-dependent and-independent pathways of apoptotic cell death in sepsis. *J Immunol* 2000, 164:3675-3680.

46. Liu G, Park Y J, Tsuruta Y, Lorne E, Abraham E. P53 attenuates lipopolysaccharide-induced nf-kappab activation and acute lung injury. *J Immunol* 2009, 182:5063-5071.
47. Sengupta S, Vonesch J L, Waltzinger C, Zheng H, Wasylyk B. Negative cross-talk between p53 and the glucocorticoid receptor and its role in neuroblastoma cells. *EMBO J* 2000, 19:6051-6064.
48. Shrestha S, Wilmeth L J, Eyer J, Shuster C B. Prc1 controls spindle polarization and recruitment of cytokinetic factors during monopolar cytokinesis. *Mol Biol Cell* 2012, 23:1196-1207.
49. Subramanian R, Wilson-Kubalek E M, Arthur C P, Bick M J, Campbell E A, Darst S A, Milligan R A, Kapoor T M. Insights into antiparallel microtubule crosslinking by prc1, a conserved nonmotor microtubule binding protein. *Cell* 2010, 142:433-443.
50. Li C, Lin M, Liu J. Identification of prc1 as the p53 target gene uncovers a novel function of p53 in the regulation of cytokinesis. *Oncogene* 2004, 23:9336-9347.
51. Jiang W, Jimenez G, Wells N J, Hope T J, Wahl G M, Hunter T, Fukunaga R. Prc1: A human mitotic spindle-associated cdk substrate protein required for cytokinesis. *Mol Cell* 1998, 2:877-885.
52. Kops G J, Kim Y, Weaver B A, Mao Y, McLeod I, Yates J R, 3rd, Tagaya M, Cleveland D W. Zwl 0 links mitotic checkpoint signaling to the structural kinetochore. *J Cell Biol* 2005, 169:49-60.
53. Kasuboski J M, Bader J R, Vaughan P S, Tauhata S B, Winding M, Morrissey M A, Joyce M V, Boggess W, Vos L, Chan G K, Hinchcliffe E H, Vaughan K T. Zwint-1 is a novel aurora b substrate required for the assembly of a dynein-binding platform on kinetochores. *Mol Biol Cell* 2011, 22:3318-3330.
54. Taylor R G, Levy H L, McInnes R R. Histidase and histidinemia. Clinical and molecular considerations. *Mol Biol Med* 1991, 8:101-116.
55. Mickiewicz B, Vogel H J, Wong H R, Winston B W. Metabolomics as a novel approach for early diagnosis of pediatric septic shock and its mortality. *Am J Respir Crit Care Med* 2013, 187:967-976.
56. Lipina C, Hundal H S. Is reddl a metabolic eminence grise? *Trends Endocrinol Metab* 2016, 27:868-880.
57. Gordon B S, Steiner J L, Williamson D L, Lang C H, Kimball S R. Emerging role for regulated in development and DNA damage 1 (reddl) in the regulation of skeletal muscle metabolism. *Am J Physiol Endocrinol Metab* 2016, 311:E157-174.
58. Steiner J L, Crowell K T, Kimball S R, Lang C H. Disruption of redd1 gene ameliorates sepsis-induced decrease in mtorcl signaling but has divergent effects on proteolytic signaling in skeletal muscle. *Am J Physiol Endocrinol Metab* 2015, 309:E981-994.
59. Britto F A, Begue G, Rossano B, Docquier A, Vernus B, Sar C, Ferry A, Bonnieu A, 01 lendorff V, Favier F B. Redd1 deletion prevents dexamethasone-induced skeletal muscle atrophy. *Am J Physiol Endocrinol Metab* 2014, 307:E983-993.
60. Patel G P, Balk R A. Systemic steroids in severe sepsis and septic shock. *Am J Respir Crit Care Med* 2012, 185:133-139.
61. Simon R: Clinical trial designs for evaluating the medical utility of prognostic and predictive biomarkers in oncology. *Per Med* 2010; 7:33-47.
62. Zhang J, Yu K F: What's the relative risk? A method of correcting the odds ratio in cohort studies of common outcomes. *JAMA* 1998; 280:1690-1691.
63. Wong H R, Cvijanovich N Z, Allen G L, et al: Corticosteroids are associated with repression of adaptive immunity gene programs in pediatric septic shock. *Am J Respir Crit Care Med* 2014; 189:940-946.

What is claimed is:

1. A method of treating a pediatric patient having septic shock, the method comprising:
    analyzing a blood sample from a pediatric patient having septic shock to determine mRNA expression levels of JAK2, LYN, PRKCB, and SOS2 biomarkers;
    determining whether the mRNA expression levels of each of the biomarkers are greater than a respective cut-off mRNA expression level; and
    classifying the patient as endotype A/high risk of adverse outcome, or other than endotype A/high risk of adverse outcome, based on the determination of whether the mRNA expression levels of each of the biomarkers are greater than the respective cut-off mRNA expression level, wherein a classification of endotype A/high risk of adverse outcome comprises:
    a) a non-elevated level of JAK2 and a non-elevated level of PRKCB; or b) a non-elevated level of JAK2, an elevated level of PRKCB, and a non-elevated level of LYN;
    and wherein a classification other than endotype A/high risk of adverse outcome comprises:
    c) a non-elevated level of JAK2, an elevated level of PRKCB, and an elevated level of LYN; or
    d) an elevated level of JAK2, a non-elevated level of SOS2, and a highly elevated level of LYN; or
    e) elevated levels of JAK2 and SOS2; or
    f) an elevated level of JAK2, a non-elevated level of SOS2, and a non-highly elevated level of LYN;
    wherein the method further comprises administering a treatment comprising one or more corticosteroids to the patient if classified as other than endotype A/high risk of adverse outcome, or administering a treatment comprising one or more high risk therapies comprising at least one selected from the group consisting of immune enhancing therapy, extracorporeal membrane oxygenation/life support, plasmapheresis, pulmonary artery catheterization, and/or high volume continuous hemofiltration to the patient if classified as endotype A/high risk of adverse outcome, to provide a method of treating a pediatric patient having septic shock.

2. The method of claim 1, wherein the biomarker mRNA expression levels are determined by mRNA quantification, by normalized mRNA counts, and/or by cycle threshold (CT) values.

3. The method of claim 1, wherein the biomarker mRNA levels are determined by normalized mRNA counts, and wherein:
    a) an elevated level of JAK2 corresponds to a JAK2 mRNA count greater than 1780;
    b) an elevated level of PRKCB corresponds to a PRKCB mRNA count greater than 990;
    c) an elevated level of SOS2 corresponds to a SOS2 mRNA count greater than 480;
    d) an elevated level of LYN corresponds to a LYN mRNA count greater than 870; and
    e) a highly elevated level of LYN corresponds to a LYN mRNA count greater than 940.

4. The method of claim 1, wherein the biomarker mRNA levels are determined by normalized mRNA counts, and wherein:
    a) an elevated level of JAK2 corresponds to a JAK2 mRNA count greater than 1784;

b) an elevated level of PRKCB corresponds to a PRKCB mRNA count greater than 986;
c) an elevated level of SOS2 corresponds to a SOS2 mRNA count greater than 480;
d) an elevated level of LYN corresponds to a LYN mRNA count greater than 873; and
e) a highly elevated level of LYN corresponds to a LYN mRNA count greater than 938.

5. The method of claim 1, wherein the determination of whether the mRNA levels of the biomarkers are non-elevated above a cut-off level comprises applying the biomarker expression level data to a decision tree comprising the biomarkers.

6. The method of claim 1, wherein a classification other than endotype A/high risk of adverse outcome comprises a classification of endotype B/low risk of adverse outcome or endotype C/moderate risk of adverse outcome.

7. The method of claim 1, wherein the determination of whether the mRNA levels of the biomarkers are non-elevated is combined with one or more patient demographic data and/or clinical characteristics and/or results from other tests or indicia of septic shock.

8. The method of claim 7, wherein the patient demographic data and/or clinical characteristics and/or results from other tests or indicia of septic shock comprise at least one selected from the group consisting of the septic shock causative organism, the presence or absence or chronic disease, and/or the age, gender, race, and/or co-morbidities of the patient.

9. The method of claim 1, wherein the determination of whether the mRNA levels of the biomarkers are non-elevated above a cut-off level is combined with one or more additional population-based risk scores.

10. The method of claim 9, wherein the one or more population-based risk scores comprises at least one selected from the group consisting of Pediatric Sepsis Biomarker Risk Model (PERSEVERE), Pediatric Risk of Mortality (PRISM), Pediatric Index of Mortality (PIM), and/or Pediatric Logistic Organ Dysfunction (PELOD).

11. The method of claim 1, wherein the sample is obtained within the first hour of presentation with septic shock.

12. The method of claim 1, wherein the sample is obtained within the first 48 hours of presentation with septic shock.

13. The method of claim 1, further comprising:
obtaining an additional blood sample from the patient at a later time point, analyzing the subsequent sample to determine subsequent expression levels of each of the JAK2, LYN, PRKCB, and SOS2 biomarkers, and determining whether the subsequent expression levels of the biomarkers are greater than the respective cut-off mRNA levels, thereby determining if the patient's endotype classification has changed; and
maintaining the treatment being administered if the patient's endotype classification has not changed, or changing the treatment being administered if the patient's endotype classification has changed.

* * * * *